US006767703B2

(12) United States Patent
Schumm et al.

(10) Patent No.: US 6,767,703 B2
(45) Date of Patent: Jul. 27, 2004

(54) MATERIALS AND METHODS FOR IDENTIFYING AND ANALYZING INTERMEDIATE TANDEM REPEAT DNA MARKERS

(75) Inventors: James W. Schumm, Madison, WI (US); Jeffery W. Bacher, Madison, WI (US)

(73) Assignee: Promega Corporation, Madison, WI (US)

( * ) Notice: Subject to any disclaimer, the term of this patent is extended or adjusted under 35 U.S.C. 154(b) by 154 days.

(21) Appl. No.: 09/784,423

(22) Filed: Feb. 15, 2001

(65) Prior Publication Data

US 2002/0012924 A1 Jan. 31, 2002

Related U.S. Application Data

(62) Division of application No. 09/018,584, filed on Feb. 4, 1998, now Pat. No. 6,238,863.

(51) Int. Cl.$^7$ .............................................. C12Q 1/68
(52) U.S. Cl. ........................................ 435/6; 536/24.3
(58) Field of Search ................... 435/6, 91.2; 536/22.1, 536/24.3

(56) References Cited

U.S. PATENT DOCUMENTS

| 4,683,202 | A | 7/1987 | Mullis ....................... 435/91.2 |
| 4,963,663 | A | 10/1990 | White et al. .............. 536/24.31 |
| 5,075,217 | A | 12/1991 | Weber ........................... 435/6 |
| 5,175,082 | A | 12/1992 | Jeffreys ........................ 435/6 |
| 5,364,759 | A | 11/1994 | Caskey et al. ................. 435/6 |
| 5,411,859 | A | 5/1995 | White et al. ................... 435/6 |
| 5,413,908 | A | 5/1995 | Jeffreys ........................ 435/6 |
| 5,582,979 | A | 12/1996 | Weber ........................... 435/6 |
| 5,599,666 | A | 2/1997 | Schumm et al. ................ 435/6 |
| 5,686,272 | A | 11/1997 | Marshall et al. ........... 435/91.2 |

FOREIGN PATENT DOCUMENTS

DE 3834636 C2 4/1980

OTHER PUBLICATIONS

Adamson, D., et al. "A Collection of Ordered Tetranucleotide–Repeat Markers from the Human Genome," (1995) *Am. J. Hum. Genet.* 57: 619–628.
Edwards et al. "DNA Typing and Genetic Mapping with Trimeric and Tetrameric Tandem Repeats," (1991) *Am. J. Hum. Genet.* 49: 746–756.
Nakamura, Y., et al. "Variable Number of Tandem Repeat (VNTR) Markers for Human Gene Mapping," (1987) *Science* 235: 1616–1622.
Jeffreys, A. J., et al. "Hypervariable 'minisatellite' regions in human DNA," (1985) *Nature* 314: 67–73.
Weber, J. L., et al. "Abundant Class of Human DNA Polymorphisms Which Can Be Typed Using the Polymerase Chain Reaction," (1989) *Am. J. Hum. Genet.* 44:388–396.

Edwards, A., et al. "Genetic Variation at Five Trimeric and Tetrameric Tandem Repeat Loci in Four Human Population Groups," (1992) *Genomics* 12: 241–253.
Hammond, H. A., et al. "Evaluation of 13 Short Tandem Repeat Loci for Use in Personal Identification Applications," (1994) *Am J. Hum. Genet.* 55: 175–189.
Walker, G. T., et al. "Isothermal in vitro amplification of DNA by a restriction enzyme/DNA polymerase system," (1992) *Proc. Natl. Acad. Sci., U.S.A,* 89: 392–396.
Frégeau, C. J., et al. "DNA Typing with Fluorescently Tagged Short Tandem Repeats: A Sensitive and Accurate Approach to Human Identification," (1993) *BioTechniques*, vol. 15, No. 1, pp. 100–119.
Schumm, J. W., et al., "Development of Nonisotopic Multiplex Amplification Sets for Analysis of Polymorphic STR Loci," (1993) *Fourth International Symposium on Human Identification*, pp. 177–187.
Schlötterer, C., et al., "Slippage synthesis of simple sequence DNA," (1992) *Nucleic Acids Research*, vol. 20, No. 2, pp. 211–215.
Levinson, G., et al., "Slipped–Strand Mispairing: A Major Mechanism for DNA Sequence Evolution," (1987) *Mol. Biol. Evol.* 4(3):203–221.
Armour, J., et al., "Isolation of human simple repeat loci by hybridization selection," (1994) *Human Molecular Genetics*, vol. 3, No. 4, pp. 599–605.
Comings, D. E., et al., "Sequence of Human Tryptophan 2,3–Dioxygenase (TDO2): Presence of a Glucocorticoid Response–like Element Composed of a GTT Repeat and in Intronic CCCCT Repeat," (1995), *Genomics* 29, pp. 390–396.
Chen, H., et al., "A Novel Zinc Finger cDNA with a Polymorphic Pentanucleotide Repeat (ATTTT)$_n$ Maps on Human Chromosome 19p," (1993) *Genomics* 15, pp. 621–625.
Edwards, M. C., et al., "Pentanucleotide repeat length polymorphism at the human CD4 locus," (1991) *Nucleic Acids Research*, vol. 19, No. 17 p. 4791.
Jurka, J., et al., "Simple Repetitive DNA Sequences from Primates: Compilation and Analysis," (1995) *J. Mol. Evol.*, 40:120–126.
Tautz, D., "Hypervariability of simple sequences as a general source for polymorphic DNA markers," (1989) *Nucleic Acids Research*, vol. 17, No. 16, pp. 6463–6471.

(List continued on next page.)

*Primary Examiner*—James Martinell
(74) *Attorney, Agent, or Firm*—Michael Best & Friedrich LLP; Grady J. Frenchick

(57) ABSTRACT

The present invention is directed to materials and methods for the identification and analysis of intermediate tandem repeat sequences in DNA, wherein an intermediate tandem repeat (ITR) sequence is a region of a DNA sequence containing at least one five to seven base repeat unit appearing in tandem at least two times. DNA markers to highly polymorphic ITR loci in the human genome are identified and analyzed, using particularly preferred embodiments of the materials and methods of the present invention.

11 Claims, 8 Drawing Sheets

OTHER PUBLICATIONS

Litt, M., et al., "A Hypervariable Microsatellite Revealed by In Vitro Amplification of a Dinucleotide Repeat within the Cadiac Muscle Actin Gene," (1989) *Am. J. Hum. Genet.* 44:397–401.

Southern, E. M., "Detection of Specific Sequences Among DNA Fragments Separated by Gel Electrophoresis," (1975) *J. Mol. Biol.* 98, pp. 503–517.

Schumm, J. W., et al., "Identification of More than 500 RFLP's by Screening Random Genomic Clones," (1988) *Am. J. Hum. Genet.* 42:143–159.

Wyman, A. R., et al., "A highly polymorphic locus in human DNA," (1980) *Proc. Natl. Acad. Sci. USA*, vol. 77, No. 11 pp. 6754–6758.

Jeffreys, A. J., et al., "Individual–specific 'fingerprints' of human DNA," (1985) *Nature*, vol. 316, pp. 76–79.

Kasai, K., et al., "Amplification of a Variable Number of Tandem Repeats (VNTR) Locus (pMCT118) by the Polymerase Chain Reaction (PCR) and Its Application to Forensic Science," (1990) *Journal of Forensic Sciences*, JFSCA, vol. 35, No. 5, pp. 1196–1200.

Decorte, R., et al., "Rapid Detection of Hypervariable Regions by the Polymerase Chain Reaction Technique," *DNA and Cell Biology*, vol. 9, No. 6, pp. 461–469.

Ponce, M. R., et al., "PCR amplification of long DNA fragments," (1992) *Nucleid Acids Research*, vol. 20, No. 3, p. 623.

Kievits, T., et al., "NASBA™ isothermal enzymatic in vitro nucleic acid amplification optimized for the diagnosis of HIV–1 infection," (1991) *Journal of Virological Methods* 35, 273–286.

Volloch, V., et al., "Ligation–mediated amplification of RNA from murine erythroid cells reveals a novel class of β globin mRNA with an extended 5'–untranslated region," (1994) *Nucleic Acids Research* vol. 22, No. 13, pp. 2507–2511.

Reyes, G. R., et al., "Sequence–independent, single–primer amplification (SISPA) of complex DNA populations," (1991) *Molecular and Cellular Probes* 5, pp. 473–481.

Current Protocols in Human Genetics, Chapter 2: Development of Genetic Markers, "Construction of Small–Insert Libraries from Genomic DNA," (1994) pp. 2.0.1–2.7.15.

Schuler G. D., et al., "A Gene Map of the Human Genome," *Science* (1996) vol. 274, pp. 540–546.

Maciver, I., Editorial, (1998) *Profiles in DNA*, vol. 1, No. 3, pp. cover page, 1–2.

Tautz, D., et al., "Simple sequences are ubiquitous repetitive components of eukaryotic genomes," (1984) *Nucleic Acids Research*, vol. 12, No. 10, pp. 4127–4138.

Puers, C., et al., "Allelic Ladder Characterization of the Short Tandem Repeat Polymorphism Located in the 5' Flanking Region to the Human Coagulation Factor XIII A Subunit Gene," (1994) *Genomics*, 23, pp. 260–264.

Waye, J. S., et al., "Sensitive and Specific Quantification of Human Genomic Deoxyribonucleic Acid (DNA) in Forensic Science Specimens: Casework Examples," (1991) *Journal of Forensic Sciences*, JFSCA, vol. 36, No. 4, pp. 1198–1203.

Borštnik, B., et al. "Tandemly repeated pentanucleotides in DNA sequences of eucaryotes," (1994) *Nucleic Acids Research*, vol. 22, No. 16, pp. 3412–3417.

Altschul, S. F., et al. "Basic Local Alignment Search Tool," (1990) *J. Mol. Biol.*, 215 pp. 403–410.

Harada, S., et al., "Polymorphism of pentanucleotide repeats in the 5' flanking region of glutathione S–transferase (GST) n gene," (1994) *Hum. Genet.* 93: 223–224.

Lander, E. S., et al., "Construction of multilocus genetic linkage maps in humans," (1987) *Proc. Natl. Acad. Sci. USA*, vol. 84, pp. 2363–2367.

Volloch, V., et al., "Identification of negative–strand complements to cytochrome oxidase subunit III RNA in *Trypanosome brucei*," (1991) *Proc. Natl. Acad. Sci., USA*, vol. 88, pp. 10671–10675.

Weber, J. L., "Informativeness of Human $(dC-dA)_n \cdot (dG-dT)_n$ Polymorphisms," (1990) *Genomics* 7, pp. 524–530.

Demers, D. B., et al., "Multiplex STR Analysis by Capillary Electrophoresis," (1998) *Profiles in DNA*, vol. 1, No. 3, pp. cover page, 1, 3–5.

Promega Bulletin ™TM227, "LIGHTSMITH™ II Luminescence Engineering System for Oligonucleotides," (1995) pp. 1–30.

Anderson, J. L .M., "Hybridization strategy", in Gene Probe 2: A Practical Approach, Hames et al. (ed.), published 1995 by IRL Press, Oxford, UK, pp. 1–29.

Moore, S. S. et al., "The Conversation of Dinucleotide Microsatellites among Mammalian Genomes Allows the Use of Heterologous PCR Primer Pairs in Closely Related Species", *Genomics*, Jul. 1991, vol. 10, No. 3, pp. 654–660.

Weissenbach, J. et al., "A second–generation linkage map of the human genome", *Nature*, Oct. 20, 1992, vol. 359, pp. 794–801.

S159 POLYMORPHIC PENTANUCLEOTIDE REPEAT

G210 POLYMORPHIC PENTANUCLEOTIDE REPEAT

SEQUENCE LISTING (1) GENERAL INFORMATION:

(iii) NUMBER OF SEQUENCES: 147

(2) INFORMATION FOR SEQ ID NO: 1

(i) SEQUENCE CHARACTERISTICS:
        (A) LENGTH: 445 bp
        (B) TYPE: Nucleic Acid
        (C) STRANDEDNESS: Double
        (D) TOPOLOGY: Circular (ii) MOLECULE TYPE: Genomic DNA (iii) HYPOTHETICAL: no (vii) IMMEDIATE SOURCE:
        (A) LIBRARY: plasmid, pGem3Zf(+)
        (B) CLONE: C074

(viii) POSITION IN GENOME:
        (A) CHROMOSOME/SEGMENT: 1

(xi) SEQUENCE DESCRIPTION: SEQ ID NO: 1:

| | |
|---|---:|
| GATCCTTTGC ACCCAGANAG AAGTAATTAT TTCAACACAG TTGGAACAGT | 50 |
| TAAAAAGATT TAAAATTTTC AAAAAAACAA TCATTTTCTC TTTTCTTTCT | 100 |
| GGCTCAGACA CCTCATTGCT TTCTGACTGA CCAAGGCGCA GCGCANTTTG | 150 |
| CAGCAGCCAT GGGGGTTCCA GAGATTCCTG GANAAAAACT GGTGACAGAN | 200 |
| AGAAACAAAA AGCGCCTGGA AAAAGATAAG CATGAAAAAG GTGCTCAGAA | 250 |
| AACAGATTGT CAAAAGTAAG TCTTACCTGT GGCTCGCATT ATTTGGGAGT | 300 |
| TATTAAAATA TGAAAGTTTG GCAAATACCC GGTTATCTAC AGTCCTTTNG | 350 |
| TTTNGTTTTG GTTTTGTTTA GTTTGGTTTT GTTTNGTTTN GTTTGACACG | 400 |
| GAATCTCTCT CTGTTGCCCA AACTGGGAAT ACAGTGGTGC CGATC | 445 |

(2) INFORMATION FOR SEQ ID NO: 2

(i) SEQUENCE CHARACTERISTICS:
        (A) LENGTH: 411bp
        (B) TYPE: Nucleic Acid
        (C) STRANDEDNESS: Double
        (D) TOPOLOGY: Circular (ii) MOLECULE TYPE: Genomic DNA (iii) HYPOTHETICAL: no (vii) IMMEDIATE SOURCE:
        (A) LIBRARY: plasmid, pGem3Zf(+)
        (B) CLONE: C221

(viii) POSITION IN GENOME:
        (A) CHROMOSOME/SEGMENT: 9p (xi) SEQUENCE DESCRIPTION: SEQ ID NO: 2:

| | |
|---|---:|
| GATCACTTGC CATCCCTGCC ACACAGTTTC CTCCTCTGGA AACTGGGGGT | 50 |
| GATGACCCCT GCCCTACCCA CTTGTCATGG CATTGGGGAC ATGAACACAC | 100 |
| TTTGCACCTG TCAGGCAAGG CTTAAACAGG GATATGCACT GGTAATAGAA | 150 |
| AAGAGGGACT AAGTTTTGTT TTGTTTTGTT TTGTTTTGTT TTGTTTTGTT | 200 |
| TTGTTTTGTT TTGTTTTGTT TTGTTTTTCT GAAGAAGTCC CTAGAAGCGC | 250 |

| | |
|---|---|
| TCAGTGTTGG AATGCTCTCT TGTAGCAGTG GCGGCTGCTG CTGGTTCCGG | 300 |
| GTCAGATGCC GGAATTGGGG GTGCGCTTGG GTGCAGCTGC ATTTCATCTG | 350 |
| GTCCTGGGCC TCGGTCCTGG CTTGGAGAGG TGCAGCTCAC AGCCACTTCA | 400 |
| TGGCTGGGAT C | 411 |

(2) INFORMATION FOR SEQ ID NO: 3

(i) SEQUENCE CHARACTERISTICS:
        (A) LENGTH: 353 bp
        (B) TYPE: Nucleic Acid
        (C) STRANDEDNESS: Double
        (D) TOPOLOGY: Circular (ii) MOLECULE TYPE: Genomic DNA (iii) HYPOTHETICAL: no (vii) IMMEDIATE SOURCE:
        (A) LIBRARY: plasmid, pGem3Zf(+)
        (B) CLONE: C240

(xi) SEQUENCE DESCRIPTION: SEQ ID NO: 3:

| | |
|---|---|
| GATCANCATG GGTTCTATCT GCCTGGCCCT TCACCCCCTA CTCAGGGCAG | 50 |
| CTCTGAATTG TCTNCCCCGC TTCAAAGTTC CCAGTTCAAC TTCTCCCTCT | 100 |
| GCCCAATCCT GTTTCCTTCT CTTCCACAGG TATTAATTTG GCCAGNTGCA | 150 |
| GTGGCTCATG CCTGTAATCT CAACTTTGGG AGGCCAAGGT GGGAGGATTG | 200 |
| CTTGANCCCA GAATTTTGAA ACCANCCTCT GAAACATANT GANACCCCTG | 250 |
| TCTCAAAACA AAACAAAACA AAACAAAACA AAACAAAAAC TANCCAGGCA | 300 |
| TGATGGTGTG TGCCTGTGGT CCCANCTATT CAGGAGGCTG AAATGGGAGG | 350 |
| ATC | 353 |

(2) INFORMATION FOR SEQ ID NO: 4

(i) SEQUENCE CHARACTERISTICS:
        (A) LENGTH: 317 bp
        (B) TYPE: Nucleic Acid
        (C) STRANDEDNESS: Double
        (D) TOPOLOGY: Circular (ii) MOLECULE TYPE: Genomic DNA (iii) HYPOTHETICAL: no (vii) IMMEDIATE SOURCE:
        (A) LIBRARY: plasmid, pGem3Zf(+)
        (B) CLONE: C331

(xi) SEQUENCE DESCRIPTION: SEQ ID NO: 4:

| | |
|---|---|
| GACCGTGGAA NCCAAAAGTC TGCCTACCGC ATCTTAGTCC AGAGTTCCTG | 50 |
| TTTTTACTTC TTTTTGAAGG TCTGTGGATT CTTTATTTTC ATGGCACCTT | 100 |
| AGCAATACAT TTTAAAAGCT TGTTTTATTT TATTCAGCAT TTTGGTTATT | 150 |
| TCCATTGGAA NANTCATTCA GGGCGTTTAG TCTGCCACAG TGCTGGAAAC | 200 |
| TAAAGCTAGG ATTACATGTT TTGTTTTGTT TTGTTTTGTT TTGTTTTGTT | 250 |
| TTGTTTTGTT TTGTTTTGTG ACAGGGTCTT GCTCTATTGC CTTAGGCTGG | 300 |
| GGTGCAGTGT TGTGATC | 317 |

(2) INFORMATION FOR SEQ ID NO: 5

(i) SEQUENCE CHARACTERISTICS:
    (A) LENGTH: 387 bp
    (B) TYPE: Nucleic Acid
    (C) STRANDEDNESS: Double
    (D) TOPOLOGY: Circular (ii) MOLECULE TYPE: Genomic DNA (iii) HYPOTHETICAL: no (vii) IMMEDIATE SOURCE:
    (A) LIBRARY: plasmid, pGem3Zf(+)
    (B) CLONE: C362

(viii) POSITION IN GENOME:
    (A) CHROMOSOME/SEGMENT: 4

(xi) SEQUENCE DESCRIPTION: SEQ ID NO: 5:

| | |
|---|---|
| GATCTGGAGT GGAGAGCATT CCAGGCAGAA TGAAGAGCCA GGACCAAGAC | 50 |
| CACNAGGTGG AAACAGACTA ACAGAAAGAA AGCCANACCA CGAGGCAGAA | 100 |
| ACAGACTAAC AGAAAGAANA TCAGGTCGAC TTGCCTAAAA AGAGTGAGCT | 150 |
| AGGGAAAAGC ATGGCGGAAG AAACAANGTT GCTGAAAGCA ACTCTTATTT | 200 |
| TCTTGGCTTA GAAACCANNA AAATGCNTTT GGGTTTTATC TTAGCATAAT | 250 |
| GAAAAGACAT GTNANACTTC TGAACACGAA ATCTGACATG TTTTACAGAC | 300 |
| NTGTTTTACA TGGTTTTGTT TTGTTTNGTT TTGTTTTGGG ATGGAGTCTC | 350 |
| GCTCTGTTGC CANGCTGGGA GTGCAATGGT TGCGATC | 387 |

(2) INFORMATION FOR SEQ ID NO: 6

(i) SEQUENCE CHARACTERISTICS:
        (A) LENGTH: 471bp
        (B) TYPE: Nucleic Acid
        (C) STRANDEDNESS: Double
        (D) TOPOLOGY: Circular (ii) MOLECULE TYPE: Genomic DNA (iii) HYPOTHETICAL: no (vii) IMMEDIATE SOURCE:
        (A) LIBRARY: plasmid, pGem3Zf(+)
        (B) CLONE: C390

(xi) SEQUENCE DESCRIPTION: SEQ ID NO: 6:

| | |
|---|---|
| GATCACGAGG TCAGGAGATG GAGACCATCC TGGCTAACAT GGTGAAACCC | 50 |
| CGTCTCTACT AAAAATACCA AAAAATTAGC CGGGCATGGT GGCGGGCGCC | 100 |
| TGTAGTCCCA GCTACTCAGG AGGCTGAGGC AGGAGAATGG CGTGAACCCG | 150 |
| GGAGGCGGAG CTTGCAGTGA GCCGAGATTG CGCCACTGCG CTCCAGCCTG | 200 |
| GGTGACAGCG AGAATCTGTC TCAAAACATA CAAAACAAA ACAAAACAAA | 250 |
| ACAAAACAAA ACAAAAAAGA TTTGGAATTA TGTAGGCAAA GTGGGAGAAA | 300 |
| GAGANGGACG AGGACTNAGG TAAAGATAAT ATGCAAAATA GAAAGAGCAN | 350 |
| GAAGGGGCAT GGATATGTGT AAATTCAAAG AAAGGCAAAG TGGCTGGTGC | 400 |
| ACAAAGAGTG AGGAGAGCAA NGNGTGAAAA TGACTTTAGT GAGACAAGGC | 450 |
| AAGGGACAAA TCATGAAAAA T | 471 |

(2) INFORMATION FOR SEQ ID NO: 7

(i) SEQUENCE CHARACTERISTICS:
        (A) LENGTH: 367 bp

```
            (B) TYPE: Nucleic Acid
            (C) STRANDEDNESS: Double
            (D) TOPOLOGY: Circular (ii) MOLECULE TYPE: Genomic DNA (iii) HYPOTHETICAL: no (vii) IMMEDIATE SOURCE:
            (A) LIBRARY: plasmid,  pGem3Zf(+)
            (B) CLONE: G022

(viii) POSITION IN GENOME:
            (A) CHROMOSOME/SEGMENT: 2p (xi) SEQUENCE DESCRIPTION: SEQ ID NO: 7:

GATCGCACCA CTGCACTCCA GCCTTGGTGA CAGAGCAAAA CTCNTTCTCC              50

AAAGAAAAGA AAAGAAAAGA AAAGAAAAGA AAAGAAAAAA AAAATCCATG             100

GTGAAAGTGA CGACAGTNGA GTAGGGGATG AGCTCAAAGC AAATGCATGC             150

ATGTNCCCCA CCCTCAACAC AAACACACAC ACACACACAC ACACACACAC             200

ACACACACAC ACATACTT  CTTTAGAGAT ATTTAGGTGT ATATATGCTA              250

ACTTAGGAAA CTTTAGAAAA CCTTGTTATG ATATTATTAG TCAAAAAATA             300

TTTAAGCCAC AGTTTCGCAA TTTTAAGATT GTACTACTGG TATCTGGAGT             350

ATCTGAATCT CTGGATC                                                 367

(2) INFORMATION FOR SEQ ID NO: 8

(i) SEQUENCE CHARACTERISTICS:
            (A) LENGTH: 295 bp
            (B) TYPE: Nucleic Acid
            (C) STRANDEDNESS: Double
            (D) TOPOLOGY: Circular (ii) MOLECULE TYPE: Genomic DNA (iii) HYPOTHETICAL: no (vii) IMMEDIATE SOURCE:
            (A) LIBRARY: plasmid,  pGem3Zf(+)
            (B) CLONE: G023

(viii) POSITION IN GENOME:
            (A) CHROMOSOME/SEGMENT: 16q (xi) SEQUENCE DESCRIPTION: SEQ ID NO: 8:

GATCACAGCA CTGCACTGCA GCCTGGGCAA GAGAGCAAGA CCCTCTCTCT              50

CAGGGAAGAA AAGAAAAGAA AAGAAAAGAA AAGAAAAGAA AAGAAAAGAA             100

AAGAAAAGAA AGGAAGGAAA GAGAGAGGAA GGAAGGAAGG AAGGTAAGAA             150

GGAAGGAAGG AAAGAAAGAA GGAAGGAAGG TAGGGTGGTT TTGGGATGTG             200

AAATGCTGTC AGTCAACAAA GAGCTATGAC CACAGGTGTC ACTGAGTAGC             250

AGGGGCAGCC CATCCTGCTC CCTAGCTGCA CTCACCCTGA AGATC                  295

(2) INFORMATION FOR SEQ ID NO: 9

(i) SEQUENCE CHARACTERISTICS:
            (A) LENGTH: 361 bp
            (B) TYPE: Nucleic Acid
            (C) STRANDEDNESS: Double
            (D) TOPOLOGY: Circular (ii) MOLECULE TYPE: Genomic DNA (iii) HYPOTHETICAL: no
```

```
    (vii) IMMEDIATE SOURCE:
          (A) LIBRARY: plasmid, pGem3Zf(+)
          (B) CLONE: G025

(viii) POSITION IN GENOME:
          (A) CHROMOSOME/SEGMENT: 1

(xi) SEQUENCE DESCRIPTION: SEQ ID NO: 9:

GATCTGATGG TTTCATAAGT GTCTGGCATT TCCCCTGCTT GTACTTCTCT           50

CCCCGGCTAC CGTGTGAAAA AGGTCCTTGC TTCCCCTTTG CCTTCCACCA          100

TGATTGTGAG CTTCCTGAGG CCTCCACAGA CATGTGGAAC TGTGAGTCAA          150

TTAAACTTCT TTCCTTTATA AATTACCCAG TCTCAGGAAG TTCTTTGTAG          200

CAGTGTGAGA ATGGAGGAAG AAAGAAAAAG AAAAAAAAGG AAAAGAAAAG          250

AAAAGAAAAG AAAAGAAAAG AAAGGAAGA AGAAAGAAAG AAAGAAAGAA           300

AGAAAGAAAG AAAGAAAGAA AGAAAGAAAG AAAGAGAGAG AAGTGGTTAG          350

CAAATGTGAT C                                                   361

(2) INFORMATION FOR SEQ ID NO: 10

(i) SEQUENCE CHARACTERISTICS:
          (A) LENGTH: 318 bp
          (B) TYPE: Nucleic Acid
          (C) STRANDEDNESS: Double
          (D) TOPOLOGY: Circular (ii) MOLECULE TYPE: Genomic DNA (iii) HYPOTHETICAL: no (vii) IMMEDIATE SOURCE:
          (A) LIBRARY: plasmid, pGem3Zf(+)
          (B) CLONE: G047

(viii) POSITION IN GENOME:
          (A) CHROMOSOME/SEGMENT: 2p (xi) SEQUENCE DESCRIPTION: SEQ ID NO: 10:

GATCACTTGA GGCCAGGGGT TCGAGGCCAG CCTGGGCAAC ATATCAAGAC           50

CCCCATCTCT ACATAAAAAG AAGAAGAAAC GAAAAGAAAA GAAAAGAAAA         100

GAAAAGAAAA GAAAAGAAAA GAAAAGAGTG GAAGAGTGCA GGAGCCGAGA         150

GGGAGAGAAA ATGTAGTGGT GAGGGGCAGC TTCTGGAAAG GCCCATACTA         200

CAGAGGGAGG AATCCTAATT CCTCACTATC TCTCTAACAT CAGGTAAGCA         250

TCTCATGATG CAGTTAGAAA GCACATTTCC TTCTTCAGTT TCCCCTCTGG         300

CTGTGTTGAC CCAGCCCA                                            318

(2) INFORMATION FOR SEQ ID NO: 11

(i) SEQUENCE CHARACTERISTICS:
          (A) LENGTH: 362 bp
          (B) TYPE: Nucleic Acid
          (C) STRANDEDNESS: Double
          (D) TOPOLOGY: Circular (ii) MOLECULE TYPE: Genomic DNA (iii) HYPOTHETICAL: no (vii) IMMEDIATE SOURCE:
          (A) LIBRARY: plasmid, pGem3Zf(+)
          (B) CLONE: G065
```

```
       (viii) POSITION IN GENOME:
             (A) CHROMOSOME/SEGMENT: 1q (xi) SEQUENCE DESCRIPTION: SEQ ID NO: 11:

GATCACATTT GCTAACCACT TCTCTCTCTN TCTTTCTTTC TTTCTTTCTT            50

TCTTTCTTTC TNTCTTNCTT TCTTTCTTTC TATCTTCCTT TCTTTACTTT           100

NCTTTNCTNT TCTNTTCTAT TCCTTTANAT TTCTTTTTCT TTCTTTCTCC           150

ATTCTCACNC TGCTANAAAG AACTTCCTGA GACTGGGTAA TTTATANAGG           200

AAAGAAGTTT AATTGACTCA CAGTTCCACA TGTTTGTGGA GGCCTCAGGA           250

AACTTACAAT CNTGGTGGAA NGCAAAGGGG AANCAAGGAC CTTTTTCACA           300

CGGTAGCCGG GGAAATAATT ACAANCAGGG GAAATGCCAN ACACTTATGA           350

AACCATCAGA TC                                                   362

(2) INFORMATION FOR SEQ ID NO: 12

(i) SEQUENCE CHARACTERISTICS:
             (A) LENGTH: 329 bp
             (B) TYPE: Nucleic Acid
             (C) STRANDEDNESS: Double
             (D) TOPOLOGY: Circular (ii) MOLECULE TYPE: Genomic DNA (iii) HYPOTHETICAL: no (vii) IMMEDIATE SOURCE:
             (A) LIBRARY: plasmid,  pGem3Zf(+)
             (B) CLONE: G085

(viii) POSITION IN GENOME:
             (A) CHROMOSOME/SEGMENT: 10q (xi) SEQUENCE DESCRIPTION: SEQ ID NO: 12:

GATCATGTCA TTGCACTCCA GCCTGGGTGA TACAGCAAGC CTCATCGAAA            50

GAAAAGAAAA GAAAAGAAAA GAAAAGAAAA GAAAAGAAAA GAAAAGAAAA           100

GAAAGGAAGA AAAGAAAACA AANAGATAGA AAGCAANCNN GTGGCNTGAG           150

AANTNAAATT CTTATAGGTA ACCTGGAGGA CTTTTATCTT TCCAGGAGTC           200

TCTCTCAATG CATTTAGACT CAACAANGAT TTCCTTTTCT CTTGTCTCTA           250

NAAANAAATG CATTTCCTCA AAANANTGGA GGTCANATTA TGTTANAGAT           300

GGGAGAATGC ACTGAGTTNC GCTGAANGA                                 329

(2) INFORMATION FOR SEQ ID NO: 13

(i) SEQUENCE CHARACTERISTICS:
             (A) LENGTH: 372 bp
             (B) TYPE: Nucleic Acid
             (C) STRANDEDNESS: Double
             (D) TOPOLOGY: Circular (ii) MOLECULE TYPE: Genomic DNA (iii) HYPOTHETICAL: no (vii) IMMEDIATE SOURCE:
             (A) LIBRARY: plasmid,  pGem3Zf(+)
             (B) CLONE: G132

(viii) POSITION IN GENOME:
             (A) CHROMOSOME/SEGMENT: 4 qter (xi) SEQUENCE DESCRIPTION: SEQ ID NO: 13:
```

```
GATCTACCAT TCTTGGGTCT GGAGAACAGT GGCCCTTGTT TCTTTTCTTT          50

TCTTTTCTTT TCTTTTCTTT TCTTTTCTTT TCTTTTCTTT CCTTTTCTTT         100

TCCTTTCCTT TCCTTTTCTT CTCTCTCTCC TTCTCTCTCT CTCTCTCTCT         150

CTCTCTCTCT CTCTCTCTCT CTCCCTCTCC CTTCCCTTCC CTTCCTTTCC         200

CTTCCTTTCC TTTCCTTTCA TTTTTTTTGA CATGGAGTTT CACTCTTGTC         250

ATCCAGGCTG GAGTACAGTA NTGTGATTTT GGCTCACTGC AACCTCTGCC         300

TCNTGGGTTC AAGAGATTCT CCTGCCTCAG CTTCCTGANT AGCTGGGATT         350

ACAGGTGCCT GCCACCATGC TT                                       372
```

(2) INFORMATION FOR SEQ ID NO: 14

(i) SEQUENCE CHARACTERISTICS:
        (A) LENGTH: 350 bp
        (B) TYPE: Nucleic Acid
        (C) STRANDEDNESS: Double
        (D) TOPOLOGY: Circular (ii) MOLECULE TYPE: Genomic DNA (iii) HYPOTHETICAL: no (vii) IMMEDIATE SOURCE:
        (A) LIBRARY: plasmid, pGem3Zf(+)
        (B) CLONE: G145.1

(xi) SEQUENCE DESCRIPTION: SEQ ID NO: 14:

```
GATCTCTTGA AGCCTCGCAN ATAAAGGCTC CAGTGGGGTA TGATTGCACC          50

ANTGCACTCC ANCCTGNGAN ACGGNAGAGA GATTCTGTCT CAAAAGAAAA         100

CAAAATAAAA GAAAANAAAA NAAAANAAAA TAAAANAAAA TANAAGAAAA         150

GAAAAGGATG CTTTAAAAAT NTGGCAAAAT GTNCCCTTTA TTGACTACTG         200

CCTTGTTTTA ATTTNCTCTA TTTNTCTATT TATTTTCTCA GTGTACTTTC         250

CCATNTNNCT TTNTCTCTTC CTTCTTTGAA AGTAATTCTT GGCCAGGCAT         300

GGTGGTTCAT GCCTATAATC TCANCACTTN AGGGGGCTNA AGCNGGAAGA         350
```

(2) INFORMATION FOR SEQ ID NO: 15

(i) SEQUENCE CHARACTERISTICS:
        (A) LENGTH: 372 bp
        (B) TYPE: Nucleic Acid
        (C) STRANDEDNESS: Double
        (D) TOPOLOGY: Circular (ii) MOLECULE TYPE: Genomic DNA (iii) HYPOTHETICAL: no (vii) IMMEDIATE SOURCE:
        (A) LIBRARY: plasmid, pGem3Zf(+)
        (B) CLONE: G152

(viii) POSITION IN GENOME:
        (A) CHROMOSOME/SEGMENT: 8 qter (xi) SEQUENCE DESCRIPTION: SEQ ID NO: 15:

```
GACCACCTGA GGTCATGAGT TCCAGACCAG CCTGGCCAAC ATGGCAAAAC          50

CCCGTCTCTA CTAAAAATAC AAAAAATAGC CGGTGTGATG GTGGGTGCCT         100

GTAATCCCAG CTACTCAGGA GGCATGAGAA TCGCTTGAAC CTGGGAGGCG         150

GAGGTTGTAG TGAGCTGAGA TTGCGCCTCT GCACTCCAGC CTGAGTGATA         200
```

| | |
|---|---:|
| GAGTGAGACC CCATCTTGAA AGAAAAGAAA AGAAAAGAAA AGAAAAGAAA | 250 |
| AAGAAATTCA TCATTGGGAA ACATCATGGA NGGCCGCNAC CAGTCAGGGG | 300 |
| AACATTTCCG AAAGCNANTT NTTCTTCCAA TGCCCTATGT TNCTTCCCCN | 350 |
| AAGCTTGCCA TTTTNAACCC TT | 372 |

(2) INFORMATION FOR SEQ ID NO: 16

(i) SEQUENCE CHARACTERISTICS:
        (A) LENGTH: 361 bp
        (B) TYPE: Nucleic Acid
        (C) STRANDEDNESS: Double
        (D) TOPOLOGY: Circular (ii) MOLECULE TYPE: Genomic DNA (iii) HYPOTHETICAL: no (vii) IMMEDIATE SOURCE:
        (A) LIBRARY: plasmid, pGem3Zf(+)
        (B) CLONE: G153

(viii) POSITION IN GENOME:
        (A) CHROMOSOME/SEGMENT: 8 qter (xi) SEQUENCE DESCRIPTION: SEQ ID NO: 16:

| | |
|---|---:|
| GACCACCTGA GGTCATGAGT TCCAGACCAG CCTGGCCAAC ATGGCAAAAC | 50 |
| CCCGTCTCTA CTAAAAATAC AAAAAATAGC CGGTGTGATG GTGGGTGCCT | 100 |
| GTAATCCCAG CTACTCAGGA GGCATGAGAA TCGCTTGAAC CTGGGAGGCG | 150 |
| GAGGTTGTAN TGAGCTGAGA TTGCGCCTCT GCACTCCAGC CTGAGTGATA | 200 |
| GAGTGAGACC CCATCTTGAA AGAAAAGAAA AGAAAAGAAA AGAAAAGAAA | 250 |
| AGAANTTCNT CATTGGGAAA CATCATGGAG GCCGCAGCAN TCAGGGGAAC | 300 |
| ATTTCCGAAA GCNAGTTGTC NTTCCAATGC CCTATGTTNC TTCCCCNAAG | 350 |
| CNTGCCATTT T | 361 |

(2) INFORMATION FOR SEQ ID NO: 17

(i) SEQUENCE CHARACTERISTICS:
        (A) LENGTH: 447 bp
        (B) TYPE: Nucleic Acid
        (C) STRANDEDNESS: Double
        (D) TOPOLOGY: Circular (ii) MOLECULE TYPE: Genomic DNA (iii) HYPOTHETICAL: no (vii) IMMEDIATE SOURCE:
        (A) LIBRARY: plasmid, pGem3Zf(+)
        (B) CLONE: G158

(viii) POSITION IN GENOME:
        (A) CHROMOSOME/SEGMENT: 5q (xi) SEQUENCE DESCRIPTION: SEQ ID NO: 17:

| | |
|---|---:|
| GATCGCCTGG GTACAGCAGG AAAGAAGGGG GCGGCCACGG CAAGGCAGCC | 50 |
| TCCGACTGCC CGGCGGGGGA NGCCGGCGGC GGCCCCTTCT CGCCCTCTCC | 100 |
| TATAAGCAGT TTTATAAGCT TCCTGAGACT ANAAAAGGAA AAGAAAGAA | 150 |
| AAGAAAAGAA AAGAAAAATC AGTCTCTATT TTATATGCGT ATAATTTTTT | 200 |
| TTATATGCGT ATAATTTTTT TTTTAACCAA AAACTCNTTA TGGACAAAAC | 250 |
| AAACTACCAT CCCACTCCAA ATTATCTCTG CATCATGCTC ACAACCTCAG | 300 |

```
CNCAAATTTC AATANAANTT TTATTGGGAT ATGTTTGGCT TCCATCAATT          350

GAAATTTCCC CTAATGAATA AAATTTCCTC CCGTTTTTTT GGTAAACATT          400

TCCCCTTGNA AGGCCCACCT AAAAATCNCC NGGNCTTTTT CCAAAGG            447
```

(2) INFORMATION FOR SEQ ID NO: 18

(i) SEQUENCE CHARACTERISTICS:
        (A) LENGTH: 415 bp
        (B) TYPE: Nucleic Acid
        (C) STRANDEDNESS: Double
        (D) TOPOLOGY: Circular (ii) MOLECULE TYPE: Genomic DNA (iii) HYPOTHETICAL: no (vii) IMMEDIATE SOURCE:
        (A) LIBRARY: plasmid, pGem3Zf(+)
        (B) CLONE: G181

(viii) POSITION IN GENOME:
        (A) CHROMOSOME/SEGMENT: <Unknown>
        (B) MAP POSITION: <Unknown>
        (C) UNITS: <Unknown>

(xi) SEQUENCE DESCRIPTION: SEQ ID NO: 18:

```
GATCCCAAGC TTCCCGGGTA CCGCGATCAC CTGAGGTCAG GAGTTCAAGA          50

CCAGCCTTCT CAACATGGCA AAACCTCATT TCTACTAAAA ATACAAAAAA         100

TTAGCTGGGC ATGGTCTTGG GTGCCTGTAA TCCCAGCTAC TCAGGAGGCT         150

GAGGCAGGAG AATGTCTTGA ACCCAGGAGG CGGTGGCTGC AGTGAGGCAA         200

NATTTTGCCA GTGTNCTCCA GCCTGGGTGA CAANANTGAA ACTCCGTCTG         250

AAAGAAAGAA AGAAAAAGAA AGAAAGGAAG GAAGGAAGGA AGGAAAGGGA         300

AGGAAAGAAA AGAAAAGAAA AGAAAAGAAA AGAAAAGAAA AGAAAAGAAA         350

AGAAAAGAAA AGAAAAGAAA AGAAAAGAAA TNAGATGGGG GAGCTCTACC        400

GAACTGATTC CGATC                                              415
```

(2) INFORMATION FOR SEQ ID NO: 19

(i) SEQUENCE CHARACTERISTICS:
        (A) LENGTH: 444 bp
        (B) TYPE: Nucleic Acid
        (C) STRANDEDNESS: Double
        (D) TOPOLOGY: Circular (ii) MOLECULE TYPE: Genomic DNA (iii) HYPOTHETICAL: no (vii) IMMEDIATE SOURCE:
        (A) LIBRARY: plasmid, pGem3Zf(+)
        (B) CLONE: G210

(viii) POSITION IN GENOME:
        (A) CHROMOSOME/SEGMENT: 8p (xi) SEQUENCE DESCRIPTION: SEQ ID NO: 19

```
GATCCTATCC TGACAAACTC AAGCAAATTC ACAAATACAA CCCTCTAGCC          50

GGCCCATGGC CTCCCTATTT GGGAGGAAAA AACTCAGTAT GATACTGTGA         100

CATATTTCAT TCATTATCTG TTAAGGTGAG CGTGGCAAAC CTGGCCGAAG         150

TGGCAGAATA TTGGGGCTCA TCACTTGGGG GAATGATTCA GGAGTGGCAT         200
```

-continued

| | |
|---|---|
| CCTTCTGTGA CCTGTGACAG CCACTTAAGG TTGTGGGATG ACTACTACAA | 250 |
| AATCCCAAAT AAAGTATATC CTAAAGGCTT TCTTTTCTTT TCTTTTCTTT | 300 |
| TCTTTTCTTT TCTCTTCTCA TCTCTTGTCT TCTCTTCTTT TCTCCTCTCC | 350 |
| CCTCCCCTCC CATCCCCTCT CCTCTCCTCT CCTTTCCTTG TTTTAAAAAC | 400 |
| AATGTCTTGC TCTGTTGACC AGGCTGGAAT GCAGTTCTGT GATC | 444 |

(2) INFORMATION FOR SEQ ID NO: 20

(i) SEQUENCE CHARACTERISTICS:
        (A) LENGTH: 321 bp
        (B) TYPE: Nucleic Acid
        (C) STRANDEDNESS: Double
        (D) TOPOLOGY: Circular (ii) MOLECULE TYPE: Genomic DNA (iii) HYPOTHETICAL: no (vii) IMMEDIATE SOURCE:
        (A) LIBRARY: plasmid, pGem3Zf(+)
        (B) CLONE: G212

(xi) SEQUENCE DESCRIPTION: SEQ ID NO: 20

| | |
|---|---|
| GATCTCCTTC AGTGTACTCA GTGCATTCTC CATCTCTTAC ATAATCTGAC | 50 |
| CTCCACTCTT CCTGGAAATG CATTTCTTTT TAGAGACAAG AGAAAGGAA | 100 |
| ATCCTTGTTG AGTCTAAATG CATTGAGANA NACTCCTGGA AAGATAAAAG | 150 |
| TCCTCCAGGT TACCTTTAAN ACTTTCATTT CTCCTGCCAC CTGCTTGCTT | 200 |
| TCTCTCTCTT TCTTTTCTTT TCTTCCTTTC TTTTCTTTTC TTTTCTTTTC | 250 |
| TTTTCTTTTC TTTTCTTTTC TTTTCTTTCG ATGAGGCTTG CTGTATCACC | 300 |
| CAGGCTGGAG TGCAATGACA T | 321 |

(2) INFORMATION FOR SEQ ID NO: 21

(i) SEQUENCE CHARACTERISTICS:
        (A) LENGTH: 329 bp
        (B) TYPE: Nucleic Acid
        (C) STRANDEDNESS: Double
        (D) TOPOLOGY: Circular (ii) MOLECULE TYPE: Genomic DNA (iii) HYPOTHETICAL: no (vii) IMMEDIATE SOURCE:
        (A) LIBRARY: plasmid, pGem3Zf(+)
        (B) CLONE: G233

(viii) POSITION IN GENOME:
        (A) CHROMOSOME/SEGMENT: 10q (xi) SEQUENCE DESCRIPTION: SEQ ID NO: 21

| | |
|---|---|
| GATCGCTTGA GCCTTGGAGA TTGAGGCTAC GGTGAGCTAT GATTGCACCA | 50 |
| CTGCACTCCA GCCTGGGTGA CAGAGTGAGA CCCTGGGAGA AAAAAAGAAA | 100 |
| GAAAAGAAAA GAAAAGAAAA GAAAAGAAAA GAAAAGAAAA GTCNTGACCT | 150 |
| TGGAAAAAAC CANAATTTCT GATGTTGTAC AACTCCTGAA TTCTGACTGC | 200 |
| TCTCTCCNCN GAAAGANGGA ATNNNTGNTC CTTGGAGGAT TCNTACTAAT | 250 |
| ATTCTTCGGT CNANACAAAA ACNTGACCTC NAGCCNAGAA AACAANATTN | 300 |
| NNCCNTTCCA TAGAAAAGTT CAGGGGACA | 329 |

-continued (2) INFORMATION FOR SEQ ID NO: 22

(i) SEQUENCE CHARACTERISTICS:
        (A) LENGTH: 412 bp
        (B) TYPE: Nucleic Acid
        (C) STRANDEDNESS: Double
        (D) TOPOLOGY: Circular (ii) MOLECULE TYPE: Genomic DNA (iii) HYPOTHETICAL: no (vii) IMMEDIATE SOURCE:
        (A) LIBRARY: plasmid, pGem3Zf(+)
        (B) CLONE: G234

(viii) POSITION IN GENOME:
        (A) CHROMOSOME/SEGMENT: 16 qter (xi) SEQUENCE DESCRIPTION: SEQ ID NO: 22

```
GGATCACGCC ATTGCACTCC ACTCTGGGCA ACAAGAGCAA AACTCCATCT         50

CAGAAAAAAA GAAAGAAAGA AAGAAAGAAA GAGAGAAAAG AAAACAGAAA        100

AGAAAAGAAA AGAAAAGAAA AGAAAAGAAA AGAAAAGAAA AGAAAAGAAC        150

CCNNCAGAAA GCCAAGGCAA TGGGAACAAG CTGGGGCAAG TGCCTGGAGG        200

TGTTGCTGGA AAGGCAGATA GGGCAGAGAG CACCTGGACT CTTCCAAAAC        250

ATATTAGCAT CATGGTAAAG CCCTCAGCCC AAGTCCCCCA GAACATAGCC        300

GTAGTCAACC AAGTTGAGAT TGATTACTAG CTTCCTGTNA CAAGGGAGAT        350

TATNCNCACA CAAGTGCCAT CTGCCTCTCC CTTCACCCAG CTTGAGTTTC        400

GCTTGTAGCA CT                                                 412
```

(2) INFORMATION FOR SEQ ID NO: 23

(i) SEQUENCE CHARACTERISTICS:
        (A) LENGTH: 359 bp
        (B) TYPE: Nucleic Acid
        (C) STRANDEDNESS: Double
        (D) TOPOLOGY: Circular (ii) MOLECULE TYPE: Genomic DNA (iii) HYPOTHETICAL: no (vii) IMMEDIATE SOURCE:
        (A) LIBRARY: plasmid, pGem3Zf(+)
        (B) CLONE: G235

(viii) POSITION IN GENOME:
        (A) CHROMOSOME/SEGMENT: 2p (xi) SEQUENCE DESCRIPTION: SEQ ID NO: 23

```
GATCACCAGG CCCCTGAGGA AGCAGCACAG AAAAACACAA ATAATATCAA         50

TATCAGGCAG CCACAGGGGA AACAATGGGG CATTTCTCCG TGCTACATGC        100

ATGCTGCTAT TGTTTCAAGG GCTGGGGAAT TAATTCCACT TATTTATTTA        150

AGGCGTGTCA ACTCACTGCC TAAACCTGTT TCAGTGTCAA AATGGATAAA        200

ACTTTTATGG CTCATAAAAT ANANCCATTC ATCTCAATGT TCTTTGTGGT        250

GGGTTTTCTT TTCTTTTCTT TTCTTTTCTT TTCTTTTTTC TTTTTTTTTC        300

TGGCATACTG AGCTAAACCT CTGCTCTGAA ACGGTTACAT CTGAACCCAT        350

TGCTGCTAT                                                    359
```

(2) INFORMATION FOR SEQ ID NO: 24

(i) SEQUENCE CHARACTERISTICS:
        (A) LENGTH: 516 bp
        (B) TYPE: Nucleic Acid
        (C) STRANDEDNESS: Double
        (D) TOPOLOGY: Circular (ii) MOLECULE TYPE: Genomic DNA (iii) HYPOTHETICAL: no (vii) IMMEDIATE SOURCE:
        (A) LIBRARY: plasmid, pGem3Zf(+)
        (B) CLONE: G331

(xi) SEQUENCE DESCRIPTION: SEQ ID NO: 24

```
GACTTTCCCA CCTTCTGATG TGGGCATTTA GTGCTATAAA TTTCCCTCTA         50

AACACTGCTT TAGCTGTGTC CCANAGATTC TGGTATGTTG TGTCTTTGTT        100

CTCATTGGTT TCAAAGAACT TATTTATTTC TGCCTTAATT TTGTTATTTA        150

CCCAGTAGTC ATTCAGGAGA AGGTAGTTCA GTTTCCATGT AGTTGTGAAG        200

TTTTGAGTGA GTTTCTTTCC TTTTCTTTTC TTTTCTTTTC TTTTCTTTTC        250

CTTTCTTTCT TTCTTTCTTT CTTTCTTTCT TTCTTTCTTT CTTTCTTTCT        300

TTCTTTTGTT TGAGATGGAG TCTTACTCTG TCGCCAGTCT GGAGTGCAGT        350

GGTGTCATCT CAGCTCGCTG CAACCTCCGC CTCCTGGGTT CAANAAATTC        400

CTCTGCCTCA GCCTCCCAAG TAGCTGGGTT TACAGGCACA CACCACCACG        450

CCCAGCTAAT TTTTTGTATT TTANTAAAGA CAGGGTTTCA CCATGTTGAC        500

NAAAATGGTC TCGATC                                             516
```

(2) INFORMATION FOR SEQ ID NO: 25

(i) SEQUENCE CHARACTERISTICS:
        (A) LENGTH: 556 bp
        (B) TYPE: Nucleic Acid
        (C) STRANDEDNESS: Double
        (D) TOPOLOGY: Circular (ii) MOLECULE TYPE: Genomic DNA (iii) HYPOTHETICAL: no (vii) IMMEDIATE SOURCE:
        (A) LIBRARY: plasmid, pGem3Zf(+)
        (B) CLONE: G405

(xi) SEQUENCE DESCRIPTION: SEQ ID NO: 25

```
GATCTCACAT TCTTCCTCAG AATTCTTCTT GTTACCTCTG CAAAATTTCA         50

TCCTTCAAAC TCAAAGCTCA TTATCTTTGG ACTCTGTGAC ACTCTTCTGA        100

TTCTCATATC ACTTCTTGAT TTTCCTGCAT TTCCTCACTA ACTCTCAGCT        150

CATAATCATA TAAAATCACT AAGACTCTTT TTATATTGTC ATGAAGCTCA        200

GGTATTTTCA CAGATTGAAC CATTTCCCTG TAGACAGCAA TGCTCAACAT        250

GAACCATTCA CATCCTTCTT CCAAAGCACA GACTCTTCTT GCCATCTGCG        300

TCATGCCCAT GCTCATGTGC ATGGAGCCTG GTTCATTATC TTCCAAAATC        350

AAGCTTCCCC CACTTGATTT CTCTTTTCTT TTCTTTCCTT TCCTTTCCTC        400

TTTTCCTTTT CCCTTTCCCT TTCCTTACCT TTCCTTTCCT TTCCTTTCCT        450

CTCCTCTTTT CTCTTTTCTT TTCTTTTCTT TTCTTTTCTT TTCCTTTCCT        500
```

-continued

```
TTCNTTTCTT TTATTTGCAC CTCACTCTTG CCAAGGCTGG GATGGCAGTA         550

ANCACG                                                        556
```

(2) INFORMATION FOR SEQ ID NO: 26

(i) SEQUENCE CHARACTERISTICS:
        (A) LENGTH: 335bp
        (B) TYPE: Nucleic Acid
        (C) STRANDEDNESS: Double
        (D) TOPOLOGY: Circular (ii) MOLECULE TYPE: Genomic DNA (iii) HYPOTHETICAL: no (vii) IMMEDIATE SOURCE:
        (A) LIBRARY: plasmid, pGem3Zf(+)
        (B) CLONE: G475

(viii) POSITION IN GENOME:
        (A) CHROMOSOME/SEGMENT: 15q22.3

(xi) SEQUENCE DESCRIPTION: SEQ ID NO: 26

```
GATCACGCCA TTGCACTCCA GCCTGGGCGA CTGAGCAAGA CTCAGTCTCA          50

AAGAAAAGAA AAGAAAAGAA AAGAAAAGAA AAGAAAAGAA AAGAAAAGAA         100

AAGAAAAGAA AATTGTAAGG AGTTTTCTCA ATTAATAACC CAAATAAGAG         150

AATTCTTTCC ATGTATCAAT CATGATACTA AGCACTTTAC ACACATGTAT         200

GTTATGTAAT CATTATATCA TGCATGCAAG GTAATGAGTA TTATTTTCCT         250

CATTTTATAA AAGAGGAAAC TGATGTTTGA GGCTACTTTG CTTAAGACCG         300

CAGAACTAGC AAAGGAAAAG AGAAGTGAAT GTATC                         335
```

(2) INFORMATION FOR SEQ ID NO: 27

(i) SEQUENCE CHARACTERISTICS:
        (A) LENGTH: 333 bp
        (B) TYPE: Nucleic Acid
        (C) STRANDEDNESS: Double
        (D) TOPOLOGY: Circular (ii) MOLECULE TYPE: Genomic DNA (iii) HYPOTHETICAL: no (vii) IMMEDIATE SOURCE:
        (A) LIBRARY: plasmid, pGem3Zf(+)
        (B) CLONE: G539

(viii) POSITION IN GENOME:
        (A) CHROMOSOME/SEGMENT: 15q26.2

(xi) SEQUENCE DESCRIPTION: SEQ ID NO: 27

```
GATCGTGCCA CTGCACTCCA GCCTGGGCAA CAGAGTAAGA CTCAGTCTCC          50

AAAAAAAAAA AAAGAAAGAA AGAAAAGAA AGAAAGAAAG AAAGAAAGAA          100

AAGAAAAGAA AAGAAAAGAA AAGAAAAGAA AAGAAAAGAA AAGAAAAGAA         150

AAGAAAAGAA AAAGAAAAAG AAAAAATAAA GAGGTGAACG GTACTGAACA         200

GAAACTAAGA AGGCTGAGAG CCAACTCTGA GGTAACAGCT AGGAGCTGAA         250

GCAGGAAAGC TAAAATCTGC CCCAGTCCCA TTGCTGATAG ACTCACCATT         300

TACTAACAGA GAAACCATTC CTCCTTTTAG ATC                           333
```

(2) INFORMATION FOR SEQ ID NO: 28

(i) SEQUENCE CHARACTERISTICS:
        (A) LENGTH: 1011 bp
        (B) TYPE: Nucleic Acid
        (C) STRANDEDNESS: Double
        (D) TOPOLOGY: Circular (ii) MOLECULE TYPE: Genomic DNA (iii) HYPOTHETICAL: no (vii) IMMEDIATE SOURCE:
        (A) LIBRARY: plasmid,  pGem3Zf(+)
        (B) CLONE: S023

(xi) SEQUENCE DESCRIPTION: SEQ ID NO: 28

| | |
|---|---:|
| CTGTACTGAA TTACAGCCCC AAATCTGGGT CAACTGGGGA GAGACGACGA | 50 |
| GGATTAGGGT TCCAAGGTGA AACTGTGCCA TTGCGCTCCA GCCTGGGCAA | 100 |
| CAAGAATGAA ACTCTCTTAA AATAAAATAA AATAAAATAA AATAAAATAG | 150 |
| CCTAAGGATG CATTTCTCAG AACTTATCCC TGTTGTTCAA TGATGTGTGT | 200 |
| CTATACAGTG GGGCCATAAC TAAGACGTAT GTTGCCCAAG CTGGCAAGAT | 250 |
| AGCTCTGACC TTCTCTTGGG CCCCTCATTT CCCCCAAACA CAGGTTGTCT | 300 |
| GCAGTCTTGA CCAATGGCTG CCAGGGCATG GACTCCGCTG CAGGGGCCAG | 350 |
| TGGGAGGCCC CAGCTCAGGC AAAAGCACAG GCAGATATTT CAGGAGTCTG | 400 |
| CTAGGGCTGG CACTGAGGGC AGAGACAGAG GGGTCTCCCT GTCCTTTGGA | 450 |
| GAACCTCACG CTGCAGAAAT TCCAGACTGA ACCTTGATAC CGAGTAGGGG | 500 |
| AGGAGCTGTC TGCGGGTTTG AGCCTGCAGC AGGAGGAAGG ACGTGAACAT | 550 |
| TTTATCAGCT TCTGGTATGG CCTTGAGCTG GTAGTTATAA TCTTGGCCCT | 600 |
| GGTGGCCCAG GGCTACAGTC ATCCTAGCAG TCCCCGCTGA AGTGGAGCAG | 650 |
| GTACAGTCAC AGCTGTGGGG ACAGCAATGC TGGCCAAGGG TCTTCCCCCA | 700 |
| CGCTCAGTCC TGGTCAAAGG CTGCCAGACC TTTCTGAGTG CCCCCAGGGA | 750 |
| GGGGCTGGGG CGTCTCAGGG TGCCCACTGG CGAGGGAGCT GGCATCTCCA | 800 |
| CCCGCAGTCC TCGCCCCTTC AATGAGATCC CCTCTCCTGG TGACAATGGC | 850 |
| TGGCTAAACC TGTACCATTT CTGGAGGGAG ACGGGCACAC ACAAAGTCCA | 900 |
| CCTTCACCAT GTCCAGAATT TCCAGAAGTA TGGCCCGATT TACAGGTAAG | 950 |
| CCTGGCAGAG GGTGGGAGCC GAAGGACAGG GAGGAGGAGG GGACTGGGTA | 1000 |
| GCCCTGCTGT A | 1011 |

(2) INFORMATION FOR SEQ ID NO: 29

(i) SEQUENCE CHARACTERISTICS:
        (A) LENGTH: 1011 bp
        (B) TYPE: Nucleic Acid
        (C) STRANDEDNESS: Double
        (D) TOPOLOGY: Circular (ii) MOLECULE TYPE: Genomic DNA (iii) HYPOTHETICAL: no (vii) IMMEDIATE SOURCE:
        (B) CLONE: S071

(viii) POSITION IN GENOME:
        (A) CHROMOSOME/SEGMENT: 6q26-27

(xi) SEQUENCE DESCRIPTION: SEQ ID NO: 29

| | |
|---|---|
| CTGTACTGAA TTACAGCCCC AAATCTGGGT CAACTGGGGA GAGACGACGA | 50 |
| GGATTAGGGT TCCAAGGTGA AACTGTGCCA TTGCGCTCCA GCCTGGGCAA | 100 |
| CAAGAATGAA ACTCTCTTAA AATAAAATAA AATAAAATAA AATAAAATAG | 150 |
| CCTAAGGATG CATTTCTCAG AACTTATCCC TGTTGTTCAA TGATGTGTGT | 200 |
| CTATACAGTG GGGCCATAAC TAAGACGTAT GTTGCCCAAG CTGGCAAGAT | 250 |
| AGCTCTGACC TTCTCTTGGG CCCCTCATTT CCCCCAAACA CAGGTTGTCT | 300 |
| GCAGTCTTGA CCAATGGCTG CCAGGGCATG GACTCCGCTG CAGGGGCCAG | 350 |
| TGGGAGGCCC CAGCTCAGGC AAAAGCACAG GCAGATATTT CAGGAGTCTG | 400 |
| CTAGGGCTGG CACTGAGGGC AGAGACAGAG GGGTCTCCCT GTCCTTTGGA | 450 |
| GAACCTCACG CTGCAGAAAT TCCAGACTGA ACCTTGATAC CGAGTAGGGG | 500 |
| AGGAGCTGTC TGCGGGTTTG AGCCTGCAGC AGGAGGAAGG ACGTGAACAT | 550 |
| TTTATCAGCT TCTGGTATGG CCTTGAGCTG GTAGTTATAA TCTTGGCCCT | 600 |
| GGTGGCCCAG GGCTACAGTC ATCCTAGCAG TCCCCGCTGA AGTGGAGCAG | 650 |
| GTACAGTCAC AGCTGTGGGG ACAGCAATGC TGGCCAAGGG TCTTCCCCCA | 700 |
| CGCTCAGTCC TGGTCAAAGG CTGCCAGACC TTTCTGAGTG CCCCCAGGGA | 750 |
| GGGGCTGGGG CGTCTCAGGG TGCCCACTGG CGAGGGAGCT GGCATCTCCA | 800 |
| CCCGCAGTCC TCGCCCCTTC AATGAGATCC CCTCTCCTGG TGACAATGGC | 850 |
| TGGCTAAACC TGTACCATTT CTGGAGGGAG ACGGGCACAC ACAAAGTCCA | 900 |
| CCTTCACCAT GTCCAGAATT TCCAGAAGTA TGGCCCGATT TACAGGTAAG | 950 |
| CCTGGCAGAG GGTGGGAGCC GAAGGACAGG GAGGAGGAGG GGACTGGGTA | 1000 |
| GCCCTGCTGT A | 1011 |

(2) INFORMATION FOR SEQ ID NO: 30

(i) SEQUENCE CHARACTERISTICS:
        (A) LENGTH: 1000 bp
        (B) TYPE: Nucleic Acid
        (C) STRANDEDNESS: Double
        (D) TOPOLOGY: Circular (ii) MOLECULE TYPE: Genomic DNA (iii) HYPOTHETICAL: no (vii) IMMEDIATE SOURCE:
        (B) CLONE: S085

(viii) POSITION IN GENOME:
        (A) CHROMOSOME/SEGMENT: 22q11

(xi) SEQUENCE DESCRIPTION: SEQ ID NO: 30

| | |
|---|---|
| AGTCAAATGA CGGTCATAGT TTGGGTGATG GTCACGGCTC AGGTTCTTTT | 50 |
| TTACACGTGC TTGCTTTGGT TGTTGTTGTT GTTCTTTGTT TTCTTGAGGC | 100 |
| AGTATCTGGC TGTGTCTCCC AGGCTGGCGT GCAATGGCAG GATCATAGCT | 150 |
| CACTGCAACC TCAAACTCCT GGCTGAAGCA ATCTTTGTGC CCTAGCCTCC | 200 |
| CAAGTTGTTG GGATTACAGT CGTGCCCCAC CATGCCTGGC TAAGTTGTTT | 250 |
| TTTGTTTTTT GTTTTTTTTT TTTTTTCGA GACAGAGTTT TGCTCTTGTT | 300 |
| GCCCAGGCCG GAGTGCAGTG GTGTGATCTT GGCTCTCTGC AACCTCCGG | 350 |
| GTTCAAGCGA TTCTCCTGCC TCAGCCTCCC AAAGTGATGG GATTACAGGC | 400 |

```
CTGAGCCACT GTGCCTGGCC ACATGTGCTT TCCCATTCGG TCCTTGCAGC         450

AGATCTTTGA GAGAGCTCAT TTGACACTCA GGAGATGCTT CTCTAACCTG         500

CTCAGAATCA GGGCCCTGGG TATTCAGGGA GGTAGAGGGA GCAGACTGCA         550

AAGCCAGTCG TGCTCCCATC GCTCCCACTT CTCTCTCCCT CTCCATGTTT         600

TCTGTCTCCC CCACCCAGCC TAGGGCATTC CTCCCCCACA GTCCAGCCTG         650

CATCTGGCAC AGTGTCACTG CTCAGCCCAG GGATACTCAC AGCCTGGGTG         700

CCTGGCTCCT TTTTTCAGCT CATCAAACCA GGTAAAGGGA GGTTCAGATT         750

CTGCCAACCA TTGACTCAAT TCATCCAAAT CTTCAATCAC TGGAATCCTG         800

GGAGTGGCTG GATTTGAACC AGGACCTCTG AGTACTATTG CTAAGTAACT         850

GGGGGTCTCA GTGAAAGAGA GAAAAGAGCT GATAGGCCTC TTCCTGTGTT         900

ATCATGTCAG GCCATCTTTT GAAACTCTTT TCTGCAATGC TACTGAAGTA         950

TTTATGCACG TGACCTGTGC TCTTCTGTCA GTCTAGGGGT GCTGGCTGAG        1000
```

(2) INFORMATION FOR SEQ ID NO: 31

(i) SEQUENCE CHARACTERISTICS:
        (A) LENGTH: 1000 bp
        (B) TYPE: Nucleic Acid
        (C) STRANDEDNESS: Double
        (D) TOPOLOGY: Circular (ii) MOLECULE TYPE: Genomic DNA (iii) HYPOTHETICAL: no (vii) IMMEDIATE SOURCE:
        (A) LIBRARY: <Unknown>
        (B) CLONE: S125

(viii) POSITION IN GENOME:
        (A) CHROMOSOME/SEGMENT: 22q11.2-qter (xi) SEQUENCE DESCRIPTION: SEQ ID NO: 31

```
AGTCAAATGA CGGTCATAGT TTGGGTGATG GTCACGGCTC AGGTTCTTTT          50

TTACACGTGC TTGCTTTGGT TGTTGTTGTT GTTCTTTGTT TTCTTGAGGC         100

AGTATCTGGC TGTGTCTCCC AGGCTGGCGT GCAATGGCAG GATCATAGCT         150

CACTGCAACC TCAAACTCCT GGCTGAAGCA ATCTTTGTGC CCTAGCCTCC         200

CAAGTTGTTG GGATTACAGT CGTGCCCCAC CATGCCTGGC TAAGTTGTTT         250

TTTGTTTTTT GTTTTTTTTT TTTTTTTCGA GACAGAGTTT TGCTCTTGTT         300

GCCCAGGCCG GAGTGCAGTG GTGTGATCTT GGCTCTCTGC AACCTCCGG          350

GTTCAAGCGA TTCTCCTGCC TCAGCCTCCC AAAGTGATGG GATTACAGGC         400

CTGAGCCACT GTGCCTGGCC ACATGTGCTT TCCCATTCGG TCCTTGCAGC         450

AGATCTTTGA GAGAGCTCAT TTGACACTCA GGAGATGCTT CTCTAACCTG         500

CTCAGAATCA GGGCCCTGGG TATTCAGGGA GGTAGAGGGA GCAGACTGCA         550

AAGCCAGTCG TGCTCCCATC GCTCCCACTT CTCTCTCCCT CTCCATGTTT         600

TCTGTCTCCC CCACCCAGCC TAGGGCATTC CTCCCCCACA GTCCAGCCTG         650

CATCTGGCAC AGTGTCACTG CTCAGCCCAG GGATACTCAC AGCCTGGGTG         700

CCTGGCTCCT TTTTTCAGCT CATCAAACCA GGTAAAGGGA GGTTCAGATT         750

CTGCCAACCA TTGACTCAAT TCATCCAAAT CTTCAATCAC TGGAATCCTG         800

GGAGTGGCTG GATTTGAACC AGGACCTCTG AGTACTATTG CTAAGTAACT         850
```

```
GGGGGTCTCA GTGAAAGAGA GAAAAGAGCT GATAGGCCTC TTCCTGTGTT        900

ATCATGTCAG GCCATCTTTT GAAACTCTTT TCTGCAATGC TACTGAAGTA        950

TTTATGCACG TGACCTGTGC TCTTCTGTCA GTCTAGGGGT GCTGGCTGAG       1000
```

(2) INFORMATION FOR SEQ ID NO: 32

(i) SEQUENCE CHARACTERISTICS:
        (A) LENGTH: 1000 bp
        (B) TYPE: Nucleic Acid
        (C) STRANDEDNESS: Double
        (D) TOPOLOGY: Circular (ii) MOLECULE TYPE: Genomic DNA (iii) HYPOTHETICAL: no (vii) IMMEDIATE SOURCE:
        (B) CLONE: S132

(viii) POSITION IN GENOME:
        (A) CHROMOSOME/SEGMENT: 22

(xi) SEQUENCE DESCRIPTION: SEQ ID NO: 32

```
GGTGTGACCT TATCCTCTCT GAACCTCAGT TTCCTCATCC GTAAAATGAA         50

AAGCTGCTAG ATTGTTGTAA AAAAATTAAA TGGAATAGGC TAGGCGCGGT        100

GGCTCACGCC TGTAATCCCA GCACTTTAGA AGGTCGAAGA GGGTGGATCA        150

CTTGAGGTCA GGAGTTTTGA GACCAGCCTG GCCAACACGG TGAAACCCCA        200

TCTCTACTAA AAATAAAAAA TTAGCTNGGG TGCGGTGGCT CACACCTGTA        250

ATCCCAGCAC TTTGGGAGGC TGAGACGGGT GGATCACCTG AAGTCAGGAG        300

TTCAAGGCCA GCCTGGGCAA CATGGTGAAA CCACGTCTCT ACTAAAAATA        350

CAAAAATTAG CCAGGTGTGG TGGCACACGC CTGTAGTCCC AGCTACTTGG        400

GAGGCTGAGG CGGAAGAATC GCTTGAACCC AGTAGGCAGA GGTTGCAGTG        450

AGCCGAGATA AGAGTCACTG CACTCCAGCC TGGGTGACAG AGCAAGACTC        500

CCTCTCAGAA AATAAAATAA AATAAAATAA AATAAAATAA AATAAAATAA        550

AATAAAATTC TAAAAGGGCT GGCATTTGCC TAGCACTTAT ATGCCCAATA        600

AGTAATAGCT ATCAATATCC CCACCCCTAC CACTGTGCTG AAATTTAGTT        650

TCTTTTTGTC ACCCCCCATT AGACTTAAGG CAGAATTCTC ACCGTACTCC        700

TCTGTAAATT TCTGGTTCCT GGCACATAGT TGGGTCTCAG TGAAACATGG        750

TGAGTGAATG AGCAAATGCA AGGAATCTCC AGGCCATCTG GGAGCCCTCC        800

CAGGCGGGTG AGTTCGGGAA ACTCATAGTC TGTCCTCAAT GGCCCACTGA        850

AAGGTAGAGA GTTCTGGGTC CCACCTCCGC ACCCCCATCT CCTGACTCAC        900

TGCTGAAAAA TAAATAAATA AATAAAATAA CACTTATCCG GAGCCTCCCA        950

CATGCCTTGC CAGGACTGCA AGGAGCCCAG CAGAATGATG ACCGGCGTGC       1000
```

(2) INFORMATION FOR SEQ ID NO: 33

(i) SEQUENCE CHARACTERISTICS:
        (A) LENGTH: 1000 bp
        (B) TYPE: Nucleic Acid
        (C) STRANDEDNESS: Double
        (D) TOPOLOGY: Circular (ii) MOLECULE TYPE: Genomic DNA (iii) HYPOTHETICAL: no (vii) IMMEDIATE SOURCE:
          (B) CLONE: S136

(viii) POSITION IN GENOME:
           (A) CHROMOSOME/SEGMENT: 22q12-qter (xi) SEQUENCE DESCRIPTION: SEQ ID NO: 33

| | | | | |
|---|---|---|---|---|
| CCACTACATA | TCCCATACAG | GCTAATCAAC | ATGTCAAAGT | TCACACAGTT | 50 |
| ATTGTGTACC | CCTGGGCTCA | ATCTCAAGTG | TTCTGGTTGG | TCGTCCAAGG | 100 |
| TTACTTTTTT | TTTTTTTTTT | TTTTTTTTGA | GATGGAGTCT | TGCTCTGTTG | 150 |
| CCCAAGCTGG | AGTGCAATGG | CATGATCTTG | GCTCACTGCA | ACCTCCGCCT | 200 |
| CCTGGGTTCA | AGGGATTCTC | CTGCCTCAGC | CTCCTGAGTA | GTTGGGATTA | 250 |
| CAGGCATGCA | CTACCATGCC | TGGCTAATTT | TTGTATTTTT | AGTAGAGGTG | 300 |
| GAGTTTCTCC | ATGTTGTTCA | GGCTGGTCTT | GAACTCCCAA | CCTCAGGCAA | 350 |
| TCCACCTCGG | CCTCCCAAAG | TACTGGGGTT | ACAGGCATGA | GCCACTGCGC | 400 |
| CTGGCCCAAG | GTTACTTTTC | ACTACATCTT | CCTACCTGTA | TCACTTACTG | 450 |
| CCGTGTGTAT | AACTTCCACA | TTTTCTTTCT | TTTCTTTTCT | TTTCTTTTCT | 500 |
| TTTCTTTTCT | TTCTTTTCTT | TCTTTCTTTC | TTTCTCTCTC | TTTCTCTCTC | 550 |
| TCTTTCTCTC | TGTCCCCTCC | TTCCTTCTCC | TTCCTTCTTC | CTTCCTTCCT | 600 |
| TCCTTTCCTT | CCTTCCTTCC | TTCTTTCAAC | ACAGAGTCTC | ACTCTGTCAC | 650 |
| CTAGGCAGGA | GTGCAGTGGC | CCAGTCTCAG | CTCACTGCAA | CCTCCGCCTC | 700 |
| CTGGGCTCAA | GCAATTCTCT | CACCTCAGCC | TCCCGAGTAG | CTGGGATTAC | 750 |
| AGGCATGTGC | CACCATACCC | AGCTAATTTT | TGTATTTTTA | GTAGAGACGG | 800 |
| GATTTCACCA | TATTTTCCAA | GCTGGTCTCG | AACTCCTGAC | CTCAAGGGAT | 850 |
| CTGCCCGACT | CAGCCTCCCA | AACTGCTGGG | ATCATAGGTG | TGAGCCATCA | 900 |
| TGCTTGGCCC | ACACTTTCTA | TGTTAATCTA | ATTTAGATGA | TTTAATCTAT | 950 |
| ATACAGTTTC | TATATTAATC | TAATTTAGAT | GACTTAATCT | ATATACAACT | 1000 |

(2) INFORMATION FOR SEQ ID NO: 34

(i) SEQUENCE CHARACTERISTICS:
        (A) LENGTH: 1000
        (B) TYPE: Nucleic Acid
        (C) STRANDEDNESS: Double
        (D) TOPOLOGY: Circular (ii) MOLECULE TYPE: Genomic DNA (iii) HYPOTHETICAL: no (vii) IMMEDIATE SOURCE:
          (B) CLONE: S159

(viii) POSITION IN GENOME:
           (A) CHROMOSOME/SEGMENT: 21q22-qter (xi) SEQUENCE DESCRIPTION: SEQ ID NO: 34

| | | | | |
|---|---|---|---|---|
| AAACCCCGTC | TCTACTAAAA | ATACAAAAGT | TAGTTGAGCA | TGGTGGCACG | 50 |
| GGCCTGTAAT | CCCACCTATA | ATCCCACCTA | CTCGGGAGGC | TGAGGCAGGA | 100 |
| GAATCGCTTG | AACCCAGGAT | GGGGCGATTG | CAGTGAGCCG | AGATCGTGCC | 150 |
| ACTGCACTCC | AGCCTGGGTG | ACAGAGCGAG | ACTCCATCTC | AAAAAAAAAA | 200 |

| | |
|---|---|
| AAAAAAAACA GAATCATAGG CCAGGCACAG TGGCTAATTG TACCTTGGGA | 250 |
| GGCTGAGACG GGAGGATCGA GACCATCCTG GGCACCATAG TGAGACCCCA | 300 |
| TCTCTACAAA AAAAAAAAAA AATTTTTTTT AAATAGCCAG GCATGGTGAG | 350 |
| GCTGAAGTAG GATCACTTGA GCCTGGAAGG TCGAAGCTGA AGTGAGCCAT | 400 |
| GATCACACCA CTACACTCCA GCCTAGGTGA CAGAGCAAGA CACCATCTCA | 450 |
| AGAAAGAAAA AAAAGAAAGA AAGAAAAGA AAGAAAAGA AAAGAAAAGA | 500 |
| AAAGAAAAGA AAAACGAAG GGGAAAAAAA GAGAATCATA AACATAAATG | 550 |
| TAAAATTTCT CAAAAAAATC GTTATGACCA TAGGTTAGGC AAATATTTCT | 600 |
| TAGATATCAC AAAATCATGA CCTATTAAAA AATAATAATA AAGTAAGTTT | 650 |
| CATCAAAACT TAAAAGTTCT ACTCTTCAAA AGATACCTTA TAAAGAAAGT | 700 |
| AAAAAGACAC GCCACAGGCT AAGAGAAAGT ACTTCTAATC ACATATCTAA | 750 |
| AAAAGGACTT GTGTCCAGAT TAAAGAATTC TTACACATCA ATAAGACAAC | 800 |
| CCAATTAAAA ATCGGCAAAA GATTTGAAGA GATATTTAAC CAAAGAAAAC | 850 |
| ATATAAATGT GTCCGGGCGC GATGGTAATC CCAGCACTTT GAGAGGCCGA | 900 |
| GGCAGGCGGA TCACTTGAGG TCAGGAGTTT AGGACCAGTC TGGCCAACAT | 950 |
| GGTGAAACCC TGTCTCTAAT AAAAATACAA AAATTAGCTG GGTGTGGTGG | 1000 |

(2) INFORMATION FOR SEQ ID NO: 35

(i) SEQUENCE CHARACTERISTICS:
        (A) LENGTH: 1400 bp
        (B) TYPE: Nucleic Acid
        (C) STRANDEDNESS: Double
        (D) TOPOLOGY: Circular (ii) MOLECULE TYPE: Genomic DNA (iii) HYPOTHETICAL: no (vii) IMMEDIATE SOURCE:
        (B) CLONE: S176

(viii) POSITION IN GENOME:
        (A) CHROMOSOME/SEGMENT: 7q21-7q22

(xi) SEQUENCE DESCRIPTION: SEQ ID NO: 35

| | |
|---|---|
| CCATATGTTT GTTTCCTCTA CTACTGCTCC TCCCTGACCC TTAAGAAACA | 50 |
| CTGCCATAGA GCCCTACAGC TTGATGGGAG AAGTCCTATC CCTTAGGCAT | 100 |
| GGAAAGCTAT TAAGAATGTG AGAACTGTGT ATGAGGAAAC TAATTTAATA | 150 |
| ATTCCTTAGA ATGGAACCAG TTGAAAATTT CCAGCTCCAC AAACTGAAGT | 200 |
| GAAATCATTT TTTCTCCACT CCTTACTAGT AAATTTACTG TTCTATGTTA | 250 |
| AAAGAAAAAA AAAATCAACC AGCATTTAAA TTATGGCAAC CTAAAATGTG | 300 |
| TCCAGTATCT TAGAATAATT TCCCCACTGA CCTATTCCTC TGTAATAGTA | 350 |
| AAACATATAC ACAAATGTTT ATAGCTACAT TAGTCATAAT AGCCGAAAGG | 400 |
| TAAAAACAAC CCAAATGCCC ATCAACTAGA TAAATGTATT TAAAAAATAT | 450 |
| GACCCAGGCG AGGTGGCTCA GGCCTGTAAT CCCAGCACTT TAGGAGGCTG | 500 |
| AGGTGGGTGG ATGACCCAGG AGTTCAAGGC CAACCTGGTG AACATAGTGA | 550 |
| GACCCCATCT CTACAAAACT AAAAATAAAA AATTAGCCAG ATGTTGTGGT | 600 |
| GTACACCTGT AGTCCAAGCT ACTCAGGACG GTGAGGAAGG AAGATCACTT | 650 |

-continued

| | |
|---|---|
| GAGCCCGGGA GTTTGAGGCT GCAGTGAGCT ATGATCACAC CATGGCACTC | 700 |
| CAGCCTGGGC AAGAAAGTGA GACCAAATTA TTAAAAAAAA AAAAAAAAAA | 750 |
| AAAAAAAAAA AAAAAACAGA AGAAGAAGCA CTGATGCATA GGCCATGAAT | 800 |
| AAACTTTGTA AATATTATGC TAAGTAAAAG AAGCCAGAGA TGAAAATCAC | 850 |
| ATATTGTAAT TGTATGACTC CATGTGTTTT TTTAAAAAGG TCCACACAGA | 900 |
| AAAGCTATTA GTAGTTGCTC ACAGCTGGAA GGCAAGGAGG GCACGTAAGT | 950 |
| GGGTGATAGC TATAGGACAC AAGGATTATT TCTGAAATGA TGAAAATGTT | 1000 |
| CTAAAACCGT GGTAATGGTT TTACAACCCT GTGAATATAC TAAAAACTAC | 1050 |
| TGAATTGTAT ACTTAAAATG GGTGAATTAG ACGGCATATG AATTATATAT | 1100 |
| CAATAAAGGT ATTACCCAAG AAAAAGAATA CAGTATCTTC ATATTCTATA | 1150 |
| TTCTCCTCTC TTAGCTTTAC TCAGATTTCA CCTCTGTCCA GTCACCTTTC | 1200 |
| CACATTAACT CCAGGCAACT CCAAAAGTTA TTCTTCCTGC TTCATTCATC | 1250 |
| CCCCAAATAA ATTACATTCA CTACTGCGAA GATAACTGGC CAGAAACTCA | 1300 |
| ATTCCTGAAG TTCTGGCAAA TGGTTCCTAG ACTCCAAATG GAGCAGAATA | 1350 |
| ATTTGCAACT GGGCTTAAAC ACGATTGTCT TTTTTAAGGC ATCCTCAGTT | 1400 |

(2) INFORMATION FOR SEQ ID NO: 36

(i) SEQUENCE CHARACTERISTICS:
  (A) LENGTH: 1250 bp
  (B) TYPE: Nucleic Acid
  (C) STRANDEDNESS: Double
  (D) TOPOLOGY: Circular (ii) MOLECULE TYPE: Genomic DNA (iii) HYPOTHETICAL: no (vii) IMMEDIATE SOURCE:
  (B) CLONE: S189

(viii) POSITION IN GENOME:
  (A) CHROMOSOME/SEGMENT: 22q11.2-qter (xi) SEQUENCE DESCRIPTION: SEQ ID NO: 36

| | |
|---|---|
| GTTGCTCTGG CGATTCGCAA CTCGAAAATG ACACTTACTA TTCAGCTAGA | 50 |
| GATTAGAATC TCAAGCAGTA GGGCATTTTT TAATAAAAAA TTAAATTAAA | 100 |
| AATAGATTTG CCATTGTCTG CTTAATAAAA CTAGTAGCTC TGCTGGCTTA | 150 |
| GAGGGGAAAT AACATATTTC TTCGGATTTT TATATATTCA TCTGAGCAGT | 200 |
| GCTAAAAAAT AAAACAAAGT TACTAATATT CATATCTTGA GCAATTGTAC | 250 |
| ATTGCTTCTA ACTATACATT CAATCTCTCT GGCACATCCA CTGTGGCCCT | 300 |
| GAGCAGCCAG TACAGGCTCT TCTACCAAAA CGAAGCAAGC CACTCCAAAA | 350 |
| CCTGACGCGT GCAGGTGTCA CGAAACACCA GGTGCAGCTT GACAGATGTG | 400 |
| AGCCAAATAA GGAAACATTC AGCCCAGCAC TGCCCAACAG TCATGATGTA | 450 |
| TATTTTCTAC ATCTGTGCTC TAAAATATGG TGGCCACTAG CTGCAGGTGG | 500 |
| CTATTGAGAC TAAGGAACTG TATTTTTAAT TTTATTTCAT TTCAACTCAT | 550 |
| TTAAAGTAGC CACATGCCGC TAATGGCTAC TGATCTAGAG GGCAGCTGGG | 600 |
| ATGTTACTCT TGAGAATGTC TCCAGCATTT TACCTGTTGC TCTCTCTCAC | 650 |
| TCACATTTCC CATTCTAGCA CAAACAAAAC AAAACAAAAC AAAACAAAAC | 700 |

| | |
|---|---|
| AAAACAAAAC AAAACAAAAA AACCACAACA CCTACAGTTC TCCAAACAGG | 750 |
| GCATCTGTTT TGTTCCTCTG GGGGGGTCCT GTCTATGTTG TTCACGTGGC | 800 |
| CCTGGATTTC CATACTCCTA GCCTTCCTGG AAGACATCCT TTTCATCCTC | 850 |
| ACAACCCAAC CCAGGCTTTA TCTCTTCTGT GAAGCTGTCC TTGATTTTCC | 900 |
| GTTCTATCTT CCCTGCTTGT GAATGGGTCA GCTCTCCTTC CCCACCGCCC | 950 |
| TGTGCGTGTG AACATCTTTG TTCAGTATAC TGCAGTGGGT CGGGAGTATG | 1000 |
| TCCCTTCCAG ACTGGAAGGC AGAGAGGGTG GCTGTAAGGA TTGGCACTTT | 1050 |
| GGGCCAGGCA CAGTGCTCAT GCCTGTAATC CCAGCACTTT GGGAGGCTGA | 1100 |
| GGCAGGAGAA TCGCCCGACC CCAGGAGACA GAGTTTGCAG TGAGACGAGA | 1150 |
| TTGCACCACT GCACTCTAGC CTGAGGGATA GAGCAAGACT CCCTCTCAAA | 1200 |
| AAAATAAATA AATAAATAAA TAAATAAATA AAAATAAAAA ATTAAAGAGG | 1250 |

(2) INFORMATION FOR SEQ ID NO: 37

(i) SEQUENCE CHARACTERISTICS:
        (A) LENGTH: 1200 bp
        (B) TYPE: Nucleic Acid
        (C) STRANDEDNESS: Double
        (D) TOPOLOGY: Circular (ii) MOLECULE TYPE: Genomic DNA (iii) HYPOTHETICAL: no (vii) IMMEDIATE SOURCE:
        (B) CLONE: S199

(viii) POSITION IN GENOME:
        (A) CHROMOSOME/SEGMENT: 6q21

(xi) SEQUENCE DESCRIPTION: SEQ ID NO: 37

| | |
|---|---|
| TTTCATGTTC ACAGATTGGA TTAATATTGT TAAACTGTCC ATACTACCCA | 50 |
| AAGCAATCCA TAGATTCAAT GCAACCCTGA TATAGTTTGA ATGTATGTAG | 100 |
| GCACCAAAAT CTCATGTTGA ACTTTAATCC CCAGTGTTGG AGGTGGAGCC | 150 |
| TGGTGTAAGA TGTTTAGATT ATGAAGGTGA ATCCCTCATG AACGGCTTGG | 200 |
| GCCATCTGCT TGGTGATAAG TGAGCTCTTG TTCTGAGTTC ACATGAGATA | 250 |
| CAGTCATTTA AAAGCCTGTG GTACCCAAAC TCTCTCTTGC TCTTGCTTCT | 300 |
| GTTCACGCCA TGTGATATAC CTGCTATCCT TTGCCTTTGC CTTCTGCCAT | 350 |
| GATTGGAAGC TTCCTGAGTC CTCCCCAGAA ACAGATGTAA CTATGCTTCC | 400 |
| TGTACAGCCT GCAGAACCAA GAACAAACTG AAACTCTTTT GTTATAAATT | 450 |
| GCCCAGGATT AGGTGGGTGT TTTGTTTTGT TTTGTTTTGT TTTGTTTTGT | 500 |
| TTTTTGAGAT GGAGTCTCGC TCTGTCTCCC AGGCTGGAGT GCAATGATAC | 550 |
| AATCTCGGCT CACTGCAACC TCCACCTCCC CGTTCAAGCA ATTCTCCTGC | 600 |
| CTCAGCCTCC TGAGTAGCTG GGATTACAGG CGCACGCCAT CATGCCCGGC | 650 |
| TAATTTTTGT ATTTTTAGTA GAGACGGGGT TTCACCACAT TGGTCAGGCT | 700 |
| GGTCTCGAAC TCCTGACCTC ATGATCCACC CGCCTTGGCC TCCCAAAGTG | 750 |
| CTGGGATTAC AGGCGTAAGC CACCATGCCC AGCCAGGTGG TTTTTTATAG | 800 |
| TAGTGCAAGA ATGGCCGAAT ACAAACCCCT ATCAAAATAC CAATGACATT | 850 |
| TGTCAGGGAC ATTTTTAAAA ATTCTGAAAT TTATATGGAA CCACAAAAGA | 900 |

-continued

| | |
|---|---|
| CCCAGAATAG CCAAAACTAA CCTGAGCAAA AGAACAAAC CTGGAAGAAT | 950 |
| CACATTACCT GACTTCAAAG TGTACTACAG AGCTCTTATA ATCAAAACAT | 1000 |
| CATGGTACTA GCATAACAAC AGACACATAG ACCAATGGAA CACAATAGAG | 1050 |
| AACCCAGAAA CAAATCCATA CACCTACTGT GAACTCATTT TTGACAAAGG | 1100 |
| TGCCAAGAAC ATACATGGGA GAAAGGACAG TATCTCCAAA TAAATGGTGC | 1150 |
| TGAGAAAAGT GGATATACAT ATGCATAAGA ATGTAACTAG ACCCCTATCT | 1200 |

(2) INFORMATION FOR SEQ ID NO: 38

(i) SEQUENCE CHARACTERISTICS:
        (A) LENGTH: 1000 bp
        (B) TYPE: Nucleic Acid
        (C) STRANDEDNESS: Double
        (D) TOPOLOGY: Circular (ii) MOLECULE TYPE: Genomic DNA (iii) HYPOTHETICAL: no (vii) IMMEDIATE SOURCE:
        (B) CLONE: S040

(xi) SEQUENCE DESCRIPTION: SEQ ID NO: 38

| | |
|---|---|
| GCTGCAATAA ACACGGGAGT GTAGGTATCT TTAAAAGAAG GTGGTGATTT | 50 |
| CATCTCTTCT GGGTATGTAT CCAAAATAGG GTCACTGTTG GGTTATAAGG | 100 |
| TGGTTAGGTT TTGAATTTCT TTAGGAACCT CCATACTGTT TTCCATAATG | 150 |
| GGTGCACCAA TCATCATTCC CACCAACAAT GTACAAGTGT TTTATTTTCT | 200 |
| TCACACCCTC ATCAATATTT ATCTCTTGTC TTTTTTATAA TAGCCATCCT | 250 |
| AAAGACTGTA AGGCGTTTTA TTTCTAATCT CAGATTTCAC TGTAGAAACA | 300 |
| GTGATGACAC AGTCTCCAGC TTCCCTGTCT TTGTCTCTGG AGAAAAAAGC | 350 |
| CACCCTGACT TGCAGGGCCA GTCAGTGTTA GCAGCTACTA AGCCTGGTAC | 400 |
| CAGAAGAAAC CTGAGCGGGT TCCCAGGCTC CTCATCTATG GTACAGCCCT | 450 |
| GATTTGTGAT AGTGGGTCGG GGACAGGGCT TACTCTCACC ATCGGCAGCC | 500 |
| TGGAGCCTGG AGCCTGGAGA TTTGCACTTC ATCACTGTTA TCAGCATAGT | 550 |
| AGTTGGTGTC CCATACTGAT TCGACATGCA ACAAAAACCT CCAGGAGACC | 600 |
| TAAGGTGTTT ATTTGATTAT ACTACCTGCT TCCTTTTTAG TCATCTGATG | 650 |
| TGGTGCTGCT CAGTTTTAGC ATCTCTGCTT TGATTGGAAA TTCTGAGGTT | 700 |
| CTCAAAAGTA ATTCCTTATA ATATTTATAG TTTCACTCAT GGATTTTTTT | 750 |
| CTCAGACCCA AATGTACAGC CAGGTTCAGG CACAATTTCA TGGTCAAGGC | 800 |
| CATTGGATCA GACTCACATG AGTGGACGCC TCTAAAGGTC CTGGCCAGTG | 850 |
| CGATAAAGTA GCAGCGACAA TGATAAAGAA GAAGAATTAG AAAGGCAGAA | 900 |
| TTAAAGGTAT AACAATTCAC TGATGAAAGG ACTGTGTGGG GGAGAAATTT | 950 |
| CTAATTGTCT ACACAGAAAT TATTAGAATT AATGAGATAC ATAGCAAATT | 1000 |

(2) INFORMATION FOR SEQ ID NO: 39

(i) SEQUENCE CHARACTERISTICS:
        (A) LENGTH: 1050 bp
        (B) TYPE: Nucleic Acid
        (C) STRANDEDNESS: Double
        (D) TOPOLOGY: Circular (ii) MOLECULE TYPE: Genomic DNA (iii) HYPOTHETICAL: no (vii) IMMEDIATE SOURCE:
    (A) LIBRARY: <Unknown>
    (B) CLONE: S066

(xi) SEQUENCE DESCRIPTION: SEQ ID NO: 39

| | | | | | |
|---|---|---|---|---|---|
| GGGGCCTAGC | CCAGTTGGAG | GGACAAGAGC | TGGAAACTGG | GTTCCTTAGG | 50 |
| GTGGTGCCAG | AGTGGGCAGA | GACCTCTGGG | CAGCCCACGT | CCAAGTCCAG | 100 |
| AGCAAGGGGA | GGCTCATCCT | AGAAAAGAGG | CCAGAGGAGC | CATAACCACC | 150 |
| ATTGTTCCTT | GGGTTAAGGA | GTCCTTTTTT | AAAACCATCA | AAACTAAGAA | 200 |
| TCCAGTGCAT | TATGAATCCA | AGGGGTGAGG | CTCAGTGTGC | CAATGCCCCA | 250 |
| GAACAGTCTA | AGAAAGCTCC | TTTTCCCTTT | CCAGGCAGCT | CGAGCTTTAC | 300 |
| CTTCCCAAAT | TCTCCATTGA | GGGCTCCTAT | CAGCTGGAGA | AAGTCCTCCC | 350 |
| CAGTCTGGGG | ATCAGTAACG | TCTTCACCTC | CCATGCTGAT | CTGTCCGGCA | 400 |
| TCAGCAACCA | CTCAAATATC | CAGGTGTCTG | AGGTGGGTTC | AGAAGCTCCT | 450 |
| ATGCATCTGC | TTCCCAAGAT | CTATTCTGTT | CTATTCTTTC | TATTCTACTC | 500 |
| TACCCCATTT | CATTCCATTC | CATTCCACTC | AACTCCACTC | CACTCCACTC | 550 |
| CACTCCAGTT | CACTCTATTC | AATTCCACTC | CACTCCAGTT | CACTCTATTC | 600 |
| AATTCCACTC | CACTCCACTC | CAGTTCACTC | TATTCAGTTC | CACTCCACTC | 650 |
| CACTCCACTC | CACTCCAGTT | CACTCTATTC | CATTCCACTC | CATTCCACTC | 700 |
| CTCCACTCCT | CTCATCCACT | CCACTCTACT | CCTCCACTCC | ACATCTCCAC | 750 |
| TCCACTCCTC | CACTCCACTC | CTCCACTCCA | CTCATCCACT | CCACTCCTCC | 800 |
| ACTCCACTCC | TCCACTCCAC | TCCTCCACTC | CACTCCACTC | ATCCACTCCA | 850 |
| CTCTTCCATT | CCACTCCATT | CCACTCCTCC | ACTCCACTCT | TCCACTCCAC | 900 |
| TCCATTCCAC | TCCTCCACTC | CACTCCACTC | TATTCTATTC | TATTCCATTC | 950 |
| CATTCTACTC | TATTCTATTC | CATTCCATTG | CAGTCAACTC | CACTCCACTC | 1000 |
| TCTACTATTC | TATTCCACTC | CTCTCCCCTC | CACTCCATTC | CATTGCAGTC | 1050 |

(2) INFORMATION FOR SEQ ID NO: 40

(i) SEQUENCE CHARACTERISTICS:
        (A) LENGTH: 1000 bp
        (B) TYPE: Nucleic Acid
        (C) STRANDEDNESS: Double
        (D) TOPOLOGY: Circular (ii) MOLECULE TYPE: Genomic DNA (iii) HYPOTHETICAL: no (vii) IMMEDIATE SOURCE:
        (A) LIBRARY: <Unknown>
        (B) CLONE: S077

(xi) SEQUENCE DESCRIPTION: SEQ ID NO: 40

| | | | | | |
|---|---|---|---|---|---|
| GGATCCCAAT | TCATTCCGGG | CTGACACGCT | CACTGGCAGG | CGTCGGGCAT | 50 |
| CACCTAGCGG | TCACTGTTAC | TCTGAAAACG | GAGGCCTCAC | AGAGGAAGGG | 100 |
| AGCACCAGGC | CGCCTGCGCA | CAGCCTGGGG | CAACTGTGTC | TTCTCCACCG | 150 |
| CCCCCGCCCC | CACCTCCAAG | TTCCTCCCTC | CCTTGTTGCC | TAGGAAATCG | 200 |

| | |
|---|---|
| CCACTTTGAC GACCGGGTCT GATTGACCTT TGATCAGGCA AAAACGAACA | 250 |
| AACAGATAAA TAAATAAAAT AACACAAAAG TAACTAACTA AATAAAATAA | 300 |
| GTCAATACAA CCCATTACAA TACAATAAGA TACGATACGA TAGGATGCGA | 350 |
| TAGGATACGA TAGGATACAA TACAATAGGA TACGATACAA TACAATACAA | 400 |
| TACAATACAA TACAATACAA TACAATACAA TACAATACAA TACAATACGC | 450 |
| CGGGCGCGGT GGCTCATGCC TGTCATCCCG TCACTTTGGG ATGCCGAGGT | 500 |
| GGACGCATCA CCTGAAGTCG GGAGTTGGAG ACAAGCCCGA CCAACATGGA | 550 |
| GAAATCCCGT CTCAATTGAA AATACAAAAC TAGCCGGGCG CGGTGGCACA | 600 |
| TGCCTATAAT CCCAGCTGCT AGGAAGGCTG AGGCAGGAGA ATCGCTTGAA | 650 |
| CCTGGGAAGC GGAGGTTGCA GTGAGCCGAG ATTGCGCCAT CGCACTCCAG | 700 |
| TCTGAGCAAC AAGAGCGAAA CTCCGTCTCA AAAATAAATA CATAAATAAA | 750 |
| TACATACATA CATACATACA TACATACATA CATACATACA TAAATTAAAA | 800 |
| TAAATAAATA AAATAAAATA AATAAATGGG CCCTGCGCGG TGGCTCAAGC | 850 |
| CTGTCATCCC CTCACTTTGG GAGGCCAAGG CCGGTGGATC AAGAGGCGGT | 900 |
| CAGACCAACA GGGCCAGTAT GGTGAAACCC CGTCTCTACT CACAATACAC | 950 |
| AACATTAGCC GGGCGCTGTG CTGTGCTGTA CTGTCTGTAA TCCCAGCTAC | 1000 |

(2) INFORMATION FOR SEQ ID NO: 41

(i) SEQUENCE CHARACTERISTICS:
        (A) LENGTH: 1000 bp
        (B) TYPE: Nucleic Acid
        (C) STRANDEDNESS: Double
        (D) TOPOLOGY: Circular (ii) MOLECULE TYPE: Genomic DNA (iii) HYPOTHETICAL: no (vii) IMMEDIATE SOURCE:
        (A) LIBRARY: <Unknown>
        (B) CLONE: S097

(xi) SEQUENCE DESCRIPTION: SEQ ID NO: 41

| | |
|---|---|
| GGACATGAGG CTTCCCAGCC AACTGCAGGT GCACAACATA AATGTATCTG | 50 |
| CAAACAGACT GAGAGTAAAG CTGGGGGCAC AAACCTCAGC ACTGCCAGGA | 100 |
| CACACACCCT TCTCGTGGAT TCTGACTTTA TCTGACCCGG CCCACTGTCC | 150 |
| AGATCTTGTT GTGGGATTGG GACAAGGGAG GTCATAAAGC CTGTCCCCAG | 200 |
| GGCACTCTGT GTGAGCACAC GAGACCTCCC CACCCCCCCA CCGTTAGGTC | 250 |
| TCCACACATA GATCTGACCA TTAGGCATTG TGAGGAGGAC TCTAGCGCGG | 300 |
| GCTCAGGGAT CACACCAGAG AATCAGGTAC AGAGAGGAAG ACGGGGCTCG | 350 |
| AGGAGCTGAT GGATGACACA GAGCAGGGTT CCTGCAGTCC ACAGGTCCAG | 400 |
| CTCACCCTGG TGTAGGTGCC CCATCCCCCT GATCCAGGCA TCCCTGACAC | 450 |
| AGCTCCCTCC CGGAGCCTCC TCCCAGGTGA CACATCAGGG TCCCTCACTC | 500 |
| AAGCTGTCCA GAGAGGGCAG CACCTTGGAC AGCGCCCACC CCACTTCACT | 550 |
| CTTCCTCCCT CACAGGGCTC AGGGCTCAGG GCTCAAGTCT CAGAACAAAT | 600 |
| GGCAGAGGCC AGTGAGCCCA GAGATGGTGA CAGGGCAATG ATCCAGGGGC | 650 |
| AGCTGCCTGA AACGGGAGCA GGTGAAGCCA CAGATGGGAG AAGATGGTTC | 700 |

```
AGGAAGAAAA ATCCAGGAAT GGGCAGGAGA GGAGAGGAGG ACACAGGCTC            750

TGTGGGGCTG CAGCCCAGGA TGGGACTAAG TGTGAAGACA TCTCAGCAGG            800

TGAGGCCAGG TCCCATGAAC AGAGAAGCAG CTCCCACCTC CCCTGATGCA            850

CGGACACACA GAGTGTGTGG TGCTGTGCCC CCAGAGTCGG GCTCTCCTGT            900

TCTGGTCCCC AGGGAGTGAG AAGTGAGGTT GACTTGTCCC TGCTCCTCTC            950

TGCTACCCCA ACATTCACCT TCTCCTCATG CCCCTCTCTC TCAAATATGA           1000
```

(2) INFORMATION FOR SEQ ID NO: 42

(i) SEQUENCE CHARACTERISTICS:
        (A) LENGTH: 994 bp
        (B) TYPE: Nucleic Acid
        (C) STRANDEDNESS: Double
        (D) TOPOLOGY: Circular (ii) MOLECULE TYPE: Genomic DNA (iii) HYPOTHETICAL: no (vii) IMMEDIATE SOURCE:
        (B) CLONE: S103

(xi) SEQUENCE DESCRIPTION: SEQ ID NO: 42

```
CTCTGACTCT CCGCGGTGGT TGTTGGGGCT TCTTGGCTTT GTTTTGTTGT             50

TTGTTTGTAT TTTATTTTTT TCTCTCTGAC ACCTATTTTA GACAAATCTA            100

AGGGAAAAAG CCTTGACAAT AGAACATTGA TTGCTGTGTC CAACTCCAGT            150

ACCTGGAGCT TCTCTTTAAC TCAGGACTCC AGCCCATTGG TAGACGTGTG            200

TTTCTAGAGC CTGCTGGATC TCCCAGGGCT ACTCACTCAA GTTCAAGGAC            250

CAACAAGGGC AGTGGAGGTG CTGCATTGCC TGCGGTCAAG GCCAGCAAGG            300

TGGAGTGGAT GCCTCAGAAC GGACGAGATA ATGTGAACTA GCTGGAATTT            350

TTTATTCTTG TGAATATGTA CATAGGCAGC ACTAGCGACA TTGCAGTCTG            400

CTTCTGCACC TTATCTTAAA GCACTTACAG ATAGGCCTTC TTGTGATCTT            450

GCTCTATCTC ACAGCACACT CAGCACCCCC TTCTCTGCCC ATTCCCCAGC            500

CTCTCTTCCT ATCCCATCCC ATCCCATCCC ATCCCATCCC ATCCCATCCC            550

GCTCTTTTCC TACTTTTCCT TCCCTCAAAG CTTCCATTCC ACATCCGGAG            600

GAGAAGAAGG AAATGAATTT CTCTACAGAT GTCCCATTTT CAGACTGCTT            650

TAAAAAAAAT CCTTCTAATC TGCTATGCTT GAATGCCACG CGGTACAAAG            700

GAAAAGTAT CATGGAAATA TTATGCAAAT TCCCAGATTT GAAGACAAAA             750

ATACTCTAAT TCTAACCAGA GCAAGCTTTT TTATTTTTTA TACAGGGGAA            800

TATTTTATTC AAGGTAAAAT TCTAAATAAA ATATAATTGT TTTTTATCTT            850

TTCTACAGCA AATTTATAAT TTTAAGATTC CTTTTCTTGT TTATCAGCAG            900

TTGTTATTAC ATCCTTGTGG CACATTTTTT TTTAATTTTG TAAAGGTGAA            950

AAAAGCTTTT ATGAGCTCAT CTAGCAATCA GATTTTCCTG TGGA                  994
```

(2) INFORMATION FOR SEQ ID NO: 43

(i) SEQUENCE CHARACTERISTICS:
        (A) LENGTH: 1366 bp
        (B) TYPE: Nucleic Acid
        (C) STRANDEDNESS: Double
        (D) TOPOLOGY: Circular (ii) MOLECULE TYPE: Genomic DNA (iii) HYPOTHETICAL: no (vii) IMMEDIATE SOURCE:
    (B) CLONE: S110

(xi) SEQUENCE DESCRIPTION: SEQ ID NO: 43

| | | |
|---|---|---|
| GGAATTCAAT GGAATATAAC GAAATGGATA GGATCAGAAC GGAACAGAGC | 50 |
| GGAGTGGAGT TGAGTGGAGT GGATCGGAGT GCAGTGGAAA GGAATGGAAT | 100 |
| AGAATGGAAT GGAATGCAGT GGAGTGGAAT GGAATGAAGT GGAATGGAGT | 150 |
| TGAGTGGAGT GGATCGGAGT GCAGTGGAAA GGAATGGAAG AGAATGGAAT | 200 |
| GGAATGGAAT GCAGTGGACT GGAATGGAAT GGAGTGGAGT GGAGTGCAGT | 250 |
| GGGAATCGAG TGGAGTGGAG TGGAATGGAC TGGAATGGAA TGGATTGGAG | 300 |
| TGGAGTGCAG TGGAATCGAG TGGAGTGGAG TGGAATGGAG TAGAATGGAA | 350 |
| TGGAGTGGAG TGTAGTGGAA TGGAATGGAA TGGTGAATGA ATGTCAGCTA | 400 |
| AGATTGTGCA ACTGCATTCC AGTCTGGGTG ACAAAGTGAG ATCCAGTCGA | 450 |
| AGTAAAGGAA TGGAATGGAA TAGAGTAAAA TGGAATGGAA TGGTGTGGAG | 500 |
| TGGAATGGAA TGGAGAGGAA TGGAGTGGAG TGGAGTGGAG TGGAGTGGAA | 550 |
| TGGAGTGGAG TGGAATGGAG AGTGATGGAG AGGAATGGAA TGGAATGGAA | 600 |
| TGGAATGGAA TGGAATGGAA TGGAATGGAG TGGAATGGAA TGGAATGTAG | 650 |
| AGGAGTGGAG TGGATTGGAG TGGAGTGGAA TGGAGTGGAA TAGAGTGAAA | 700 |
| TTTAGTGGAG TGTAATGGAG TGGAGTGGAG TGGCAGTTGA GTGGCATGGA | 750 |
| TCAGGTGCAG TGGAATGGAA TGGAATGGAG TGGAGTGGAG AGGAGTGGAG | 800 |
| TGGAATCGAA TGGAATGGCA TGGAGTGGAG TGGAATGGAG TGGATTGGAA | 850 |
| TTGAATGCAG TGGAATGGAA TGCAATGGAG TGGAGTGGAG TGCAGTGGAG | 900 |
| TGGAGTGGAG GGGAATGGAA TGGAGTGGAG TAAAATGGTT TGGAATGGAG | 950 |
| TGGGGTGGAA TGGAGTGGGT TGGAATGGAG TGGAGTGGAG TAGAACGGAG | 1000 |
| TGATTGGGGT GGAATGGAAT AGAGTGGAAT GGAATGGAGT GGAGTGGAGT | 1050 |
| AGAACGGAGT GATTGGAGTG GAATGGAATA CAGTAGAGTG GAATGCAGTG | 1100 |
| GAGTGGAATG GAATGGAGTG GAGTGGCATG GAAAGGAATG GAGAGGAATG | 1150 |
| GAATGGAATG GAATGGAATG GAATGGAATG GAATGGAATG GAACGGTGAA | 1200 |
| ATAAAATGTG AGTTAAGATT GTGCCACTGC ATTGCAGTCT GGGGGACAGA | 1250 |
| GTGAGATACA GTCGAAATAA AGGAATGGAA GGGACTGGAG TAGAATGGAA | 1300 |
| TGGAATTGAG TGGAGTGGAA TGGAATGAAG TGGAGAGGAA TGGAATGGAG | 1350 |
| TGGAATGCAA TGGAGG | 1366 |

(2) INFORMATION FOR SEQ ID NO: 44

(i) SEQUENCE CHARACTERISTICS:
        (A) LENGTH: 19
        (B) TYPE: Nucleic Acid
        (C) STRANDEDNESS: Single
        (D) TOPOLOGY: Linear (xi) SEQUENCE DESCRIPTION: SEQ ID NO: 44

TGGCTCAGAC ACCTCATTG                                                    19

(2) INFORMATION FOR SEQ ID NO: 45

(i) SEQUENCE CHARACTERISTICS:
        (A) LENGTH: 21
        (B) TYPE: Nucleic Acid
        (C) STRANDEDNESS: Single
        (D) TOPOLOGY: Linear (xi) SEQUENCE DESCRIPTION: SEQ ID NO: 45

CACCACTGTA TTCCCAGTTT G     21

(2) INFORMATION FOR SEQ ID NO: 46

(i) SEQUENCE CHARACTERISTICS:
        (A) LENGTH: 22
        (B) TYPE: Nucleic Acid
        (C) STRANDEDNESS: Single
        (D) TOPOLOGY: Linear (xi) SEQUENCE DESCRIPTION: SEQ ID NO: 46

CACTTGCCAT CCCTGCCACA CA     22

(2) INFORMATION FOR SEQ ID NO: 47

(i) SEQUENCE CHARACTERISTICS:
        (A) LENGTH: 23
        (B) TYPE: Nucleic Acid
        (C) STRANDEDNESS: Single
        (D) TOPOLOGY: Linear (xi) SEQUENCE DESCRIPTION: SEQ ID NO: 47

AGCGCACCCC CAATTTCCGG TAT     23

(2) INFORMATION FOR SEQ ID NO: 48

(i) SEQUENCE CHARACTERISTICS:
        (A) LENGTH: 22
        (B) TYPE: Nucleic Acid
        (C) STRANDEDNESS: Single
        (D) TOPOLOGY: Linear (xi) SEQUENCE DESCRIPTION: SEQ ID NO: 48

TGGGGACATG AACACACTTT GC     22

(2) INFORMATION FOR SEQ ID NO: 49

(i) SEQUENCE CHARACTERISTICS:
        (A) LENGTH: 22
        (B) TYPE: Nucleic Acid
        (C) STRANDEDNESS: Single
        (D) TOPOLOGY: Linear (xi) SEQUENCE DESCRIPTION: SEQ ID NO: 49

GAGGCCCAGG ACCAGATGAA AT     22

(2) INFORMATION FOR SEQ ID NO: 50

(i) SEQUENCE CHARACTERISTICS:
        (A) LENGTH: 23
        (B) TYPE: Nucleic Acid
        (C) STRANDEDNESS: Single
        (D) TOPOLOGY: Linear (xi) SEQUENCE DESCRIPTION: SEQ ID NO: 50

CACCTGTCAG GCAAGGCTTA AAC     23

(2) INFORMATION FOR SEQ ID NO: 51

(i) SEQUENCE CHARACTERISTICS:
            (A) LENGTH: 24
            (B) TYPE: Nucleic Acid
            (C) STRANDEDNESS: Single
            (D) TOPOLOGY: Linear (xi) SEQUENCE DESCRIPTION: SEQ ID NO: 51

CAACACTGAG CGCTTTTAGG GACT                                              24

(2) INFORMATION FOR SEQ ID NO: 52

(i) SEQUENCE CHARACTERISTICS:
            (A) LENGTH: 24
            (B) TYPE: Nucleic Acid
            (C) STRANDEDNESS: Single
            (D) TOPOLOGY: Linear (xi) SEQUENCE DESCRIPTION: SEQ ID NO: 52

TCAGGCAAGG CTTAAACAGG GATA                                              24

(2) INFORMATION FOR SEQ ID NO: 53

(i) SEQUENCE CHARACTERISTICS:
            (A) LENGTH: 24
            (B) TYPE: Nucleic Acid
            (C) STRANDEDNESS: Single
            (D) TOPOLOGY: Linear (xi) SEQUENCE DESCRIPTION: SEQ ID NO: 53

ACACTGAGCG CTTCTAGGGA CTTC                                              24

(2) INFORMATION FOR SEQ ID NO: 54

(i) SEQUENCE CHARACTERISTICS:
            (A) LENGTH: 24
            (B) TYPE: Nucleic Acid
            (C) STRANDEDNESS: Single
            (D) TOPOLOGY: Linear (xi) SEQUENCE DESCRIPTION: SEQ ID NO: 54

TGAGCGCTTC TAGGGACTTC TTCA                                              24

(2) INFORMATION FOR SEQ ID NO: 55

(i) SEQUENCE CHARACTERISTICS:
            (A) LENGTH: 18
            (B) TYPE: Nucleic Acid
            (C) STRANDEDNESS: Single
            (D) TOPOLOGY: Linear (xi) SEQUENCE DESCRIPTION: SEQ ID NO: 55

CCCTGCCCTA CCCACTTG                                                     18

(2) INFORMATION FOR SEQ ID NO: 56

(i) SEQUENCE CHARACTERISTICS:
            (A) LENGTH: 18
            (B) TYPE: Nucleic Acid
            (C) STRANDEDNESS: Single
            (D) TOPOLOGY: Linear (xi) SEQUENCE DESCRIPTION: SEQ ID NO: 56

AGGCCCAGGA CCAGATGA                                                     18

(2) INFORMATION FOR SEQ ID NO: 57

(i) SEQUENCE CHARACTERISTICS:
    (A) LENGTH: 24
    (B) TYPE: Nucleic Acid
    (C) STRANDEDNESS: Single
    (D) TOPOLOGY: Linear (xi) SEQUENCE DESCRIPTION: SEQ ID NO: 57

GCACCTGTCA GGCAAGGCTT AAAC    24

(2) INFORMATION FOR SEQ ID NO: 58

(i) SEQUENCE CHARACTERISTICS:
        (A) LENGTH: 22
        (B) TYPE: Nucleic Acid
        (C) STRANDEDNESS: Single
        (D) TOPOLOGY: Linear (xi) SEQUENCE DESCRIPTION: SEQ ID NO: 58

CCAGCCATGA AGTGGCTGTG AG    22

(2) INFORMATION FOR SEQ ID NO: 59

(i) SEQUENCE CHARACTERISTICS:
        (A) LENGTH: 22
        (B) TYPE: Nucleic Acid
        (C) STRANDEDNESS: Single
        (D) TOPOLOGY: Linear (xi) SEQUENCE DESCRIPTION: SEQ ID NO: 59

CCCGCTTCAA AGTTCCCAGT TC    22

(2) INFORMATION FOR SEQ ID NO: 60

(i) SEQUENCE CHARACTERISTICS:
        (A) LENGTH: 21
        (B) TYPE: Nucleic Acid
        (C) STRANDEDNESS: Single
        (D) TOPOLOGY: Linear (xi) SEQUENCE DESCRIPTION: SEQ ID NO: 60

CCTCCCATTT CAGCCTCCTG A    21

(2) INFORMATION FOR SEQ ID NO: 61

(i) SEQUENCE CHARACTERISTICS:
        (A) LENGTH: 24
        (B) TYPE: Nucleic Acid
        (C) STRANDEDNESS: Single
        (D) TOPOLOGY: Linear (xi) SEQUENCE DESCRIPTION: SEQ ID NO: 61

GTCTGCCACA GTGCTGGAAA CTAA    24

(2) INFORMATION FOR SEQ ID NO: 62

(i) SEQUENCE CHARACTERISTICS:
        (A) LENGTH: 21
        (B) TYPE: Nucleic Acid
        (C) STRANDEDNESS: Single
        (D) TOPOLOGY: Linear (xi) SEQUENCE DESCRIPTION: SEQ ID NO: 62

GCACCCCAGC CTAAGGCAAT A    21

(2) INFORMATION FOR SEQ ID NO: 63

-continued (i) SEQUENCE CHARACTERISTICS:
        (A) LENGTH: 18
        (B) TYPE: Nucleic Acid
        (C) STRANDEDNESS: Single
        (D) TOPOLOGY: Linear (xi) SEQUENCE DESCRIPTION: SEQ ID NO: 63

GCATGGCGGA AGAAACAA                                                18

(2) INFORMATION FOR SEQ ID NO: 64

(i) SEQUENCE CHARACTERISTICS:
        (A) LENGTH: 19
        (B) TYPE: Nucleic Acid
        (C) STRANDEDNESS: Single
        (D) TOPOLOGY: Linear (xi) SEQUENCE DESCRIPTION: SEQ ID NO: 64

TGGCAACAGA GCGAGACTC                                               19

(2) INFORMATION FOR SEQ ID NO: 65

(i) SEQUENCE CHARACTERISTICS:
        (A) LENGTH: 21
        (B) TYPE: Nucleic Acid
        (C) STRANDEDNESS: Single
        (D) TOPOLOGY: Linear (xi) SEQUENCE DESCRIPTION: SEQ ID NO: 65

CCTGGGTGAC AGCGAGAATC T                                            21

(2) INFORMATION FOR SEQ ID NO: 66

(i) SEQUENCE CHARACTERISTICS:
        (A) LENGTH: 24
        (B) TYPE: Nucleic Acid
        (C) STRANDEDNESS: Single
        (D) TOPOLOGY: Linear (xi) SEQUENCE DESCRIPTION: SEQ ID NO: 66

TGTCCCTTGC CTTGTCTCAC TAAA                                         24

(2) INFORMATION FOR SEQ ID NO: 67

(i) SEQUENCE CHARACTERISTICS:
        (A) LENGTH: 21
        (B) TYPE: Nucleic Acid
        (C) STRANDEDNESS: Single
        (D) TOPOLOGY: Linear (xi) SEQUENCE DESCRIPTION: SEQ ID NO: 67

CAGCCTTGGT GACAGAGCAA A                                            21

(2) INFORMATION FOR SEQ ID NO: 68

(i) SEQUENCE CHARACTERISTICS:
        (A) LENGTH: 21
        (B) TYPE: Nucleic Acid
        (C) STRANDEDNESS: Single
        (D) TOPOLOGY: Linear (xi) SEQUENCE DESCRIPTION: SEQ ID NO: 68

TGTGTTGAGG GTGGGGTACA T                                            21

(2) INFORMATION FOR SEQ ID NO: 69

(i) SEQUENCE CHARACTERISTICS:

(A) LENGTH: 18
    (B) TYPE: Nucleic Acid
    (C) STRANDEDNESS: Single
    (D) TOPOLOGY: Linear (xi) SEQUENCE DESCRIPTION: SEQ ID NO: 69

CCTGGGCAAG AGAGCAAG                                                18

(2) INFORMATION FOR SEQ ID NO: 70

(i) SEQUENCE CHARACTERISTICS:
    (A) LENGTH: 21
    (B) TYPE: Nucleic Acid
    (C) STRANDEDNESS: Single
    (D) TOPOLOGY: Linear (xi) SEQUENCE DESCRIPTION: SEQ ID NO: 70

CACATCCCAA AACCACCCTA C                                            21

(2) INFORMATION FOR SEQ ID NO: 71

(i) SEQUENCE CHARACTERISTICS:
    (A) LENGTH: 20
    (B) TYPE: Nucleic Acid
    (C) STRANDEDNESS: Single
    (D) TOPOLOGY: Linear (xi) SEQUENCE DESCRIPTION: SEQ ID NO: 71

GCATTTCCCC TGCTTGTACT                                              20

(2) INFORMATION FOR SEQ ID NO: 72

(i) SEQUENCE CHARACTERISTICS:
    (A) LENGTH: 24
    (B) TYPE: Nucleic Acid
    (C) STRANDEDNESS: Single
    (D) TOPOLOGY: Linear (xi) SEQUENCE DESCRIPTION: SEQ ID NO: 72

GATCACATTT GCTAACCACT TCTC                                         24

(2) INFORMATION FOR SEQ ID NO: 73

(i) SEQUENCE CHARACTERISTICS:
    (A) LENGTH: 26
    (B) TYPE: Nucleic Acid
    (C) STRANDEDNESS: Single
    (D) TOPOLOGY: Linear (xi) SEQUENCE DESCRIPTION: SEQ ID NO: 73

GGCAACATAT CAAGACCCCC ATCTCT                                       26

(2) INFORMATION FOR SEQ ID NO: 74

(i) SEQUENCE CHARACTERISTICS:
    (A) LENGTH: 26
    (B) TYPE: Nucleic Acid
    (C) STRANDEDNESS: Single
    (D) TOPOLOGY: Linear (xi) SEQUENCE DESCRIPTION: SEQ ID NO: 74

GAAGCTGCCC CTCACCACTA CATTTT                                       26

(2) INFORMATION FOR SEQ ID NO: 75

(i) SEQUENCE CHARACTERISTICS:
    (A) LENGTH: 24

```
        (B) TYPE: Nucleic Acid
        (C) STRANDEDNESS: Single
        (D) TOPOLOGY: Linear (xi) SEQUENCE DESCRIPTION: SEQ ID NO: 75

GATCACATTT GCTAACCACT TCTC                                                  24

(2) INFORMATION FOR SEQ ID NO: 76

(i) SEQUENCE CHARACTERISTICS:
        (A) LENGTH: 24
        (B) TYPE: Nucleic Acid
        (C) STRANDEDNESS: Single
        (D) TOPOLOGY: Linear (xi) SEQUENCE DESCRIPTION: SEQ ID NO: 76

TATAAATTAC CCAGTCTCAG GAAG                                                  24

(2) INFORMATION FOR SEQ ID NO: 77

(i) SEQUENCE CHARACTERISTICS:
        (A) LENGTH: 20
        (B) TYPE: Nucleic Acid
        (C) STRANDEDNESS: Single
        (D) TOPOLOGY: Linear (xi) SEQUENCE DESCRIPTION: SEQ ID NO: 77

GTGATACAGC AAGCCTCATC                                                       20

(2) INFORMATION FOR SEQ ID NO: 78

(i) SEQUENCE CHARACTERISTICS:
        (A) LENGTH: 24
        (B) TYPE: Nucleic Acid
        (C) STRANDEDNESS: Single
        (D) TOPOLOGY: Linear (xi) SEQUENCE DESCRIPTION: SEQ ID NO: 78

AGAGACTCCT GGAAAGATAA AAGT                                                  24

(2) INFORMATION FOR SEQ ID NO: 79

(i) SEQUENCE CHARACTERISTICS:
        (A) LENGTH: 23
        (B) TYPE: Nucleic Acid
        (C) STRANDEDNESS: Single
        (D) TOPOLOGY: Linear (xi) SEQUENCE DESCRIPTION: SEQ ID NO: 79

GTCTGGAGAA CAGTGGCCCT TGT                                                   23

(2) INFORMATION FOR SEQ ID NO: 80

(i) SEQUENCE CHARACTERISTICS:
        (A) LENGTH: 24
        (B) TYPE: Nucleic Acid
        (C) STRANDEDNESS: Single
        (D) TOPOLOGY: Linear (xi) SEQUENCE DESCRIPTION: SEQ ID NO: 80

CAGGAAGCTG AGGCAGGAGA ATCT                                                  24

(2) INFORMATION FOR SEQ ID NO: 81

(i) SEQUENCE CHARACTERISTICS:
        (A) LENGTH: 18
        (B) TYPE: Nucleic Acid
```

```
        (C) STRANDEDNESS: Single
        (D) TOPOLOGY: Linear (xi) SEQUENCE DESCRIPTION: SEQ ID NO: 81

AAGGCTCCAG TGGGGTAT                                              18

(2) INFORMATION FOR SEQ ID NO: 82

(i) SEQUENCE CHARACTERISTICS:
        (A) LENGTH: 24
        (B) TYPE: Nucleic Acid
        (C) STRANDEDNESS: Single
        (D) TOPOLOGY: Linear (xi) SEQUENCE DESCRIPTION: SEQ ID NO: 82

AAAACAAGGC AGTAGTCAAT AAAG                                       24

(2) INFORMATION FOR SEQ ID NO: 83

(i) SEQUENCE CHARACTERISTICS:
        (A) LENGTH: 23
        (B) TYPE: Nucleic Acid
        (C) STRANDEDNESS: Single
        (D) TOPOLOGY: Linear (xi) SEQUENCE DESCRIPTION: SEQ ID NO: 83

GGCATGAGAA TCGCTTGAAC CTG                                        23

(2) INFORMATION FOR SEQ ID NO: 84

(i) SEQUENCE CHARACTERISTICS:
        (A) LENGTH: 24
        (B) TYPE: Nucleic Acid
        (C) STRANDEDNESS: Single
        (D) TOPOLOGY: Linear (xi) SEQUENCE DESCRIPTION: SEQ ID NO: 84

GGCCTCCATG ATGTTTCCAA TGAT                                       24

(2) INFORMATION FOR SEQ ID NO: 85

(i) SEQUENCE CHARACTERISTICS:
        (A) LENGTH: 24
        (B) TYPE: Nucleic Acid
        (C) STRANDEDNESS: Single
        (D) TOPOLOGY: Linear (xi) SEQUENCE DESCRIPTION: SEQ ID NO: 85

TCAGGAGGCA TGAGAATCGC TTGA                                       24

(2) INFORMATION FOR SEQ ID NO: 86

(i) SEQUENCE CHARACTERISTICS:
        (A) LENGTH: 24
        (B) TYPE: Nucleic Acid
        (C) STRANDEDNESS: Single
        (D) TOPOLOGY: Linear (xi) SEQUENCE DESCRIPTION: SEQ ID NO: 86

GGCCTCCATG ATGTTTCCCA ATGA                                       24

(2) INFORMATION FOR SEQ ID NO: 87

(i) SEQUENCE CHARACTERISTICS:
        (A) LENGTH: 24
        (B) TYPE: Nucleic Acid
        (C) STRANDEDNESS: Single
```

-continued (D) TOPOLOGY: Linear (xi) SEQUENCE DESCRIPTION: SEQ ID NO: 87

CTCGCCCTCT CCTATAAGCA GTTT                                                  24

(2) INFORMATION FOR SEQ ID NO: 88

(i) SEQUENCE CHARACTERISTICS:
        (A) LENGTH: 24
        (B) TYPE: Nucleic Acid
        (C) STRANDEDNESS: Single
        (D) TOPOLOGY: Linear (xi) SEQUENCE DESCRIPTION: SEQ ID NO: 88

GCAGAGATAA TTTGGAGTGG GATG                                                 24

(2) INFORMATION FOR SEQ ID NO: 89

(i) SEQUENCE CHARACTERISTICS:
        (A) LENGTH: 18
        (B) TYPE: Nucleic Acid
        (C) STRANDEDNESS: Single
        (D) TOPOLOGY: Linear (xi) SEQUENCE DESCRIPTION: SEQ ID NO: 89

CTTGGGTGCC TGTAATCC                                                           18

(2) INFORMATION FOR SEQ ID NO: 90

(i) SEQUENCE CHARACTERISTICS:
        (A) LENGTH: 18
        (B) TYPE: Nucleic Acid
        (C) STRANDEDNESS: Single
        (D) TOPOLOGY: Linear (xi) SEQUENCE DESCRIPTION: SEQ ID NO: 90

GGTAGAGCTC CCCCATCT                                                           18

(2) INFORMATION FOR SEQ ID NO: 91

(i) SEQUENCE CHARACTERISTICS:
        (A) LENGTH: 22
        (B) TYPE: Nucleic Acid
        (C) STRANDEDNESS: Single
        (D) TOPOLOGY: Linear (xi) SEQUENCE DESCRIPTION: SEQ ID NO: 91

GCAGAATATT GGGGCTCATC AC                                                   22

(2) INFORMATION FOR SEQ ID NO: 92

(i) SEQUENCE CHARACTERISTICS:
        (A) LENGTH: 24
        (B) TYPE: Nucleic Acid
        (C) STRANDEDNESS: Single
        (D) TOPOLOGY: Linear (xi) SEQUENCE DESCRIPTION: SEQ ID NO: 92

AAACAAGGAA AGGAGAGGAG AGGA                                               24

(2) INFORMATION FOR SEQ ID NO: 93

(i) SEQUENCE CHARACTERISTICS:
        (A) LENGTH: 23
        (B) TYPE: Nucleic Acid
        (C) STRANDEDNESS: Single
        (D) TOPOLOGY: Linear (xi) SEQUENCE DESCRIPTION: SEQ ID NO: 93

AAGGTTGTGG GATGACTACT ACA                                                   23

(2) INFORMATION FOR SEQ ID NO: 94

(i) SEQUENCE CHARACTERISTICS:
        (A) LENGTH: 21
        (B) TYPE: Nucleic Acid
        (C) STRANDEDNESS: Single
        (D) TOPOLOGY: Linear (xi) SEQUENCE DESCRIPTION: SEQ ID NO: 94

TGGTCAACAC AGCAAGACAT T                                                     21

(2) INFORMATION FOR SEQ ID NO: 95

(i) SEQUENCE CHARACTERISTICS:
        (A) LENGTH: 22
        (B) TYPE: Nucleic Acid
        (C) STRANDEDNESS: Single
        (D) TOPOLOGY: Linear (xi) SEQUENCE DESCRIPTION: SEQ ID NO: 95

TCCTGCCACC TGCTTGCTTT CT                                                    22

(2) INFORMATION FOR SEQ ID NO: 96

(i) SEQUENCE CHARACTERISTICS:
        (A) LENGTH: 24
        (B) TYPE: Nucleic Acid
        (C) STRANDEDNESS: Single
        (D) TOPOLOGY: Linear (xi) SEQUENCE DESCRIPTION: SEQ ID NO: 96

ATTGCACTCC AGCCTGGGTG ATAC                                                  24

(2) INFORMATION FOR SEQ ID NO: 97

(i) SEQUENCE CHARACTERISTICS:
        (A) LENGTH: 20
        (B) TYPE: Nucleic Acid
        (C) STRANDEDNESS: Single
        (D) TOPOLOGY: Linear (xi) SEQUENCE DESCRIPTION: SEQ ID NO: 97

CGCTTGAGCC TTGGAGATTG                                                       20

(2) INFORMATION FOR SEQ ID NO: 98

(i) SEQUENCE CHARACTERISTICS:
        (A) LENGTH: 24
        (B) TYPE: Nucleic Acid
        (C) STRANDEDNESS: Single
        (D) TOPOLOGY: Linear (xi) SEQUENCE DESCRIPTION: SEQ ID NO: 98

GAGCAGTCAG AATTCAGGAG TTGT                                                  24

(2) INFORMATION FOR SEQ ID NO: 99

(i) SEQUENCE CHARACTERISTICS:
        (A) LENGTH: 24
        (B) TYPE: Nucleic Acid
        (C) STRANDEDNESS: Single
        (D) TOPOLOGY: Linear

```
        (xi) SEQUENCE DESCRIPTION: SEQ ID NO: 99

TGGGCAACAA GAGCAAAACT CCAT                                           24

(2) INFORMATION FOR SEQ ID NO: 100

(i) SEQUENCE CHARACTERISTICS:
          (A) LENGTH: 23
          (B) TYPE: Nucleic Acid
          (C) STRANDEDNESS: Single
          (D) TOPOLOGY: Linear (xi) SEQUENCE DESCRIPTION: SEQ ID NO: 100

GGGACTTGGG CTGAGGGCTT TAC                                            23

(2) INFORMATION FOR SEQ ID NO: 101

(i) SEQUENCE CHARACTERISTICS:
          (A) LENGTH: 24
          (B) TYPE: Nucleic Acid
          (C) STRANDEDNESS: Single
          (D) TOPOLOGY: Linear (xi) SEQUENCE DESCRIPTION: SEQ ID NO: 101

ATATCAATAT CAGGCAGCCA CAGG                                           24

(2) INFORMATION FOR SEQ ID NO: 102

(i) SEQUENCE CHARACTERISTICS:
          (A) LENGTH: 23
          (B) TYPE: Nucleic Acid
          (C) STRANDEDNESS: Single
          (D) TOPOLOGY: Linear (xi) SEQUENCE DESCRIPTION: SEQ ID NO: 102

CCGTTTCAGA GCAGAGGTTT AGC                                            23

(2) INFORMATION FOR SEQ ID NO: 103

(i) SEQUENCE CHARACTERISTICS:
          (A) LENGTH: 23
          (B) TYPE: Nucleic Acid
          (C) STRANDEDNESS: Single
          (D) TOPOLOGY: Linear (xi) SEQUENCE DESCRIPTION: SEQ ID NO: 103

TCTCATTGGT TTCAAAGAAC TTA                                            23

(2) INFORMATION FOR SEQ ID NO: 104

(i) SEQUENCE CHARACTERISTICS:
          (A) LENGTH: 22
          (B) TYPE: Nucleic Acid
          (C) STRANDEDNESS: Single
          (D) TOPOLOGY: Linear (xi) SEQUENCE DESCRIPTION: SEQ ID NO: 104

AGACTCCATC TCAAACAAAA GA                                             22

(2) INFORMATION FOR SEQ ID NO: 105

(i) SEQUENCE CHARACTERISTICS:
          (A) LENGTH: 24
          (B) TYPE: Nucleic Acid
          (C) STRANDEDNESS: Single
          (D) TOPOLOGY: Linear (xi) SEQUENCE DESCRIPTION: SEQ ID NO: 105
```

```
TCATGTGCAT GGAGCCTGGT TCAT                                          24

(2) INFORMATION FOR SEQ ID NO: 106

(i) SEQUENCE CHARACTERISTICS:
        (A) LENGTH: 23
        (B) TYPE: Nucleic Acid
        (C) STRANDEDNESS: Single
        (D) TOPOLOGY: Linear (xi) SEQUENCE DESCRIPTION: SEQ ID NO: 106

CCCAGCCTTG GCAAGAGTGA GGT                                           23

(2) INFORMATION FOR SEQ ID NO: 107

(i) SEQUENCE CHARACTERISTICS:
        (A) LENGTH: 18
        (B) TYPE: Nucleic Acid
        (C) STRANDEDNESS: Single
        (D) TOPOLOGY: Linear (xi) SEQUENCE DESCRIPTION: SEQ ID NO: 107

GGCGACTGAG CAAGACTC                                                 18

(2) INFORMATION FOR SEQ ID NO: 108

(i) SEQUENCE CHARACTERISTICS:
        (A) LENGTH: 22
        (B) TYPE: Nucleic Acid
        (C) STRANDEDNESS: Single
        (D) TOPOLOGY: Linear (xi) SEQUENCE DESCRIPTION: SEQ ID NO: 108

TTAAGCAAAG TAGCCTCAAA CA                                            22

(2) INFORMATION FOR SEQ ID NO: 109

(i) SEQUENCE CHARACTERISTICS:
        (A) LENGTH: 19
        (B) TYPE: Nucleic Acid
        (C) STRANDEDNESS: Single
        (D) TOPOLOGY: Linear (xi) SEQUENCE DESCRIPTION: SEQ ID NO: 109

GGGCGACTGA GCAAGACTC                                                19

(2) INFORMATION FOR SEQ ID NO: 110

(i) SEQUENCE CHARACTERISTICS:
        (A) LENGTH: 24
        (B) TYPE: Nucleic Acid
        (C) STRANDEDNESS: Single
        (D) TOPOLOGY: Linear (xi) SEQUENCE DESCRIPTION: SEQ ID NO: 110

ACTCATTACC TTGCATGCAT GATA                                          24

(2) INFORMATION FOR SEQ ID NO: 111

(i) SEQUENCE CHARACTERISTICS:
        (A) LENGTH: 21
        (B) TYPE: Nucleic Acid
        (C) STRANDEDNESS: Single
        (D) TOPOLOGY: Linear (xi) SEQUENCE DESCRIPTION: SEQ ID NO: 111
```

```
CATTACCTTG CATGCATGAT A                                               21

(2) INFORMATION FOR SEQ ID NO: 112

(i) SEQUENCE CHARACTERISTICS:
        (A) LENGTH: 21
        (B) TYPE: Nucleic Acid
        (C) STRANDEDNESS: Single
        (D) TOPOLOGY: Linear (xi) SEQUENCE DESCRIPTION: SEQ ID NO: 112

TGGGCAACAG AGTAAGACTC A                                               21

(2) INFORMATION FOR SEQ ID NO: 113

(i) SEQUENCE CHARACTERISTICS:
        (A) LENGTH: 23
        (B) TYPE: Nucleic Acid
        (C) STRANDEDNESS: Single
        (D) TOPOLOGY: Linear (xi) SEQUENCE DESCRIPTION: SEQ ID NO: 113

GTTCAGTACC GTTCACCTCT TTA                                             23

(2) INFORMATION FOR SEQ ID NO: 114

(i) SEQUENCE CHARACTERISTICS:
        (A) LENGTH: 30
        (B) TYPE: Nucleic Acid
        (C) STRANDEDNESS: Single
        (D) TOPOLOGY: Linear (xi) SEQUENCE DESCRIPTION: SEQ ID NO: 114

GTAAGACTCA GTCTCCAAAA AAAAAAAAAG                                      30

(2) INFORMATION FOR SEQ ID NO: 115

(i) SEQUENCE CHARACTERISTICS:
        (A) LENGTH: 28
        (B) TYPE: Nucleic Acid
        (C) STRANDEDNESS: Single
        (D) TOPOLOGY: Linear (xi) SEQUENCE DESCRIPTION: SEQ ID NO: 115

AGGAATGGTT TCTCTGTTAG TAAATGGT                                        28

(2) INFORMATION FOR SEQ ID NO: 116

(i) SEQUENCE CHARACTERISTICS:
        (A) LENGTH: 24
        (B) TYPE: Nucleic Acid
        (C) STRANDEDNESS: Single
        (D) TOPOLOGY: Linear (xi) SEQUENCE DESCRIPTION: SEQ ID NO: 116

CAGCCTGGGC AACAAGAATG AAAC                                            24

(2) INFORMATION FOR SEQ ID NO: 117

(i) SEQUENCE CHARACTERISTICS:
        (A) LENGTH: 19
        (B) TYPE: Nucleic Acid
        (C) STRANDEDNESS: Single
        (D) TOPOLOGY: Linear (xi) SEQUENCE DESCRIPTION: SEQ ID NO: 117

TGGCCCCTGC AGCGGAGTC                                                  19
```

(2) INFORMATION FOR SEQ ID NO: 118

(i) SEQUENCE CHARACTERISTICS:
        (A) LENGTH: 21
        (B) TYPE: Nucleic Acid
        (C) STRANDEDNESS: Single
        (D) TOPOLOGY: Linear (xi) SEQUENCE DESCRIPTION: SEQ ID NO: 118

GAATTCATTT GCGGAAAGAT T                                      21

(2) INFORMATION FOR SEQ ID NO: 119

(i) SEQUENCE CHARACTERISTICS:
        (A) LENGTH: 21
        (B) TYPE: Nucleic Acid
        (C) STRANDEDNESS: Single
        (D) TOPOLOGY: Linear (xi) SEQUENCE DESCRIPTION: SEQ ID NO: 119

CTAGGGAGGC TGGAGTATTC A                                      21

(2) INFORMATION FOR SEQ ID NO: 120

(i) SEQUENCE CHARACTERISTICS:
        (A) LENGTH: 20
        (B) TYPE: Nucleic Acid
        (C) STRANDEDNESS: Single
        (D) TOPOLOGY: Linear (xi) SEQUENCE DESCRIPTION: SEQ ID NO: 120

AGAGCAAGAC CCCGTCTCAT                                        20

(2) INFORMATION FOR SEQ ID NO: 121

(i) SEQUENCE CHARACTERISTICS:
        (A) LENGTH: 20
        (B) TYPE: Nucleic Acid
        (C) STRANDEDNESS: Single
        (D) TOPOLOGY: Linear (xi) SEQUENCE DESCRIPTION: SEQ ID NO: 121

AGTCCATGGG CCTTTTAACA                                        20

(2) INFORMATION FOR SEQ ID NO: 122

(i) SEQUENCE CHARACTERISTICS:
        (A) LENGTH: 23
        (B) TYPE: Nucleic Acid
        (C) STRANDEDNESS: Single
        (D) TOPOLOGY: Linear (ii) MOLECULE TYPE: Oligonucleotide ssDNA (iii) HYPOTHETICAL: no (vii) IMMEDIATE SOURCE:
        (B) CLONE: S125

(xi) SEQUENCE DESCRIPTION: SEQ ID NO: 122

GAGAATCACT TGAACCCAGG AAG                                    23

(2) INFORMATION FOR SEQ ID NO: 123

(i) SEQUENCE CHARACTERISTICS:
        (A) LENGTH: 24
        (B) TYPE: Nucleic Acid

```
            (C) STRANDEDNESS: Single
            (D) TOPOLOGY: Linear (xi) SEQUENCE DESCRIPTION: SEQ ID NO: 123

AGAACCAGCT GTTAGTTTCG TTGA                                              24

(2) INFORMATION FOR SEQ ID NO: 124

(i) SEQUENCE CHARACTERISTICS:
            (A) LENGTH: 25
            (B) TYPE: Nucleic Acid
            (C) STRANDEDNESS: Single
            (D) TOPOLOGY: Linear (xi) SEQUENCE DESCRIPTION: SEQ ID NO: 124

GGTTGCAGTG AGCCGAGATA AGAGT                                             25

(2) INFORMATION FOR SEQ ID NO: 125

(i) SEQUENCE CHARACTERISTICS:
            (A) LENGTH: 25
            (B) TYPE: Nucleic Acid
            (C) STRANDEDNESS: Single
            (D) TOPOLOGY: Linear (xi) SEQUENCE DESCRIPTION: SEQ ID NO: 125

TGTGCCAGGA ACCAGAAATT TACAG                                             25

(2) INFORMATION FOR SEQ ID NO: 126

(i) SEQUENCE CHARACTERISTICS:
            (A) LENGTH: 20
            (B) TYPE: Nucleic Acid
            (C) STRANDEDNESS: Single
            (D) TOPOLOGY: Linear (xi) SEQUENCE DESCRIPTION: SEQ ID NO: 126

GGCCCAAGGT TACTTTTCAC                                                   20

(2) INFORMATION FOR SEQ ID NO: 127

(i) SEQUENCE CHARACTERISTICS:
            (A) LENGTH: 16
            (B) TYPE: Nucleic Acid
            (C) STRANDEDNESS: Single
            (D) TOPOLOGY: Linear (xi) SEQUENCE DESCRIPTION: SEQ ID NO: 127

GGGCCACTGC ACTCCT                                                       16

(2) INFORMATION FOR SEQ ID NO: 128

(i) SEQUENCE CHARACTERISTICS:
            (A) LENGTH: 22
            (B) TYPE: Nucleic Acid
            (C) STRANDEDNESS: Single
            (D) TOPOLOGY: Linear (xi) SEQUENCE DESCRIPTION: SEQ ID NO: 128

CATGGTGAGG CTGAAGTAGG AT                                                22

(2) INFORMATION FOR SEQ ID NO: 129

(i) SEQUENCE CHARACTERISTICS:
            (A) LENGTH: 25
            (B) TYPE: Nucleic Acid
            (C) STRANDEDNESS: Single
```

-continued (D) TOPOLOGY: Linear (xi) SEQUENCE DESCRIPTION: SEQ ID NO: 129

GTGGCGTGTC TTTTTACTTT CTTTA                                                 25

(2) INFORMATION FOR SEQ ID NO: 130

(i) SEQUENCE CHARACTERISTICS:
        (A) LENGTH: 18
        (B) TYPE: Nucleic Acid
        (C) STRANDEDNESS: Single
        (D) TOPOLOGY: Linear (xi) SEQUENCE DESCRIPTION: SEQ ID NO: 130

AGGCAGCCCA GGAACAAT                                                           18

(2) INFORMATION FOR SEQ ID NO: 131

(i) SEQUENCE CHARACTERISTICS:
        (A) LENGTH: 22
        (B) TYPE: Nucleic Acid
        (C) STRANDEDNESS: Single
        (D) TOPOLOGY: Linear (xi) SEQUENCE DESCRIPTION: SEQ ID NO: 131

CCAAGATAGC GGCCAAGATA GT                                                 22

(2) INFORMATION FOR SEQ ID NO: 132

(i) SEQUENCE CHARACTERISTICS:
        (A) LENGTH: 24
        (B) TYPE: Nucleic Acid
        (C) STRANDEDNESS: Single
        (D) TOPOLOGY: Linear (xi) SEQUENCE DESCRIPTION: SEQ ID NO: 132

GAGGGCAGCT GGGATGTTAC TCTT                                           24

(2) INFORMATION FOR SEQ ID NO: 133

(i) SEQUENCE CHARACTERISTICS:
        (A) LENGTH: 24
        (B) TYPE: Nucleic Acid
        (C) STRANDEDNESS: Single
        (D) TOPOLOGY: Linear (xi) SEQUENCE DESCRIPTION: SEQ ID NO: 133

TGCCCTGTTT GGAGAACTGT AGGT                                           24

(2) INFORMATION FOR SEQ ID NO: 134

(i) SEQUENCE CHARACTERISTICS:
        (A) LENGTH: 19
        (B) TYPE: Nucleic Acid
        (C) STRANDEDNESS: Single
        (D) TOPOLOGY: Linear (xi) SEQUENCE DESCRIPTION: SEQ ID NO: 134

CTCCCCAGAA ACAGATGTA                                                       19

(2) INFORMATION FOR SEQ ID NO: 135

(i) SEQUENCE CHARACTERISTICS:
        (A) LENGTH: 20
        (B) TYPE: Nucleic Acid
        (C) STRANDEDNESS: Single
        (D) TOPOLOGY: Linear (xi) SEQUENCE DESCRIPTION: SEQ ID NO: 135

GTGAGCCGAG ATTGTATCAT                                          20

(2) INFORMATION FOR SEQ ID NO: 136

(i) SEQUENCE CHARACTERISTICS:
        (A) LENGTH: 19
        (B) TYPE: Nucleic Acid
        (C) STRANDEDNESS: Single
        (D) TOPOLOGY: Linear (xi) SEQUENCE DESCRIPTION: SEQ ID NO: 136

TCGGGGACAG GGCTTACTC                                           19

(2) INFORMATION FOR SEQ ID NO: 137

(i) SEQUENCE CHARACTERISTICS:
        (A) LENGTH: 24
        (B) TYPE: Nucleic Acid
        (C) STRANDEDNESS: Single
        (D) TOPOLOGY: Linear (xi) SEQUENCE DESCRIPTION: SEQ ID NO: 137

ATCATTGTCG CTGCTACTTT ATCG                                     24

(2) INFORMATION FOR SEQ ID NO: 138

(i) SEQUENCE CHARACTERISTICS:
        (A) LENGTH: 21
        (B) TYPE: Nucleic Acid
        (C) STRANDEDNESS: Single
        (D) TOPOLOGY: Linear (xi) SEQUENCE DESCRIPTION: SEQ ID NO: 138

CTACTCTACC CCATTTCATT C                                        21

(2) INFORMATION FOR SEQ ID NO: 139

(i) SEQUENCE CHARACTERISTICS:
        (A) LENGTH: 20
        (B) TYPE: Nucleic Acid
        (C) STRANDEDNESS: Single
        (D) TOPOLOGY: Linear (xi) SEQUENCE DESCRIPTION: SEQ ID NO: 139

GTAGAGTGGA GTGGATGAGA                                          20

(2) INFORMATION FOR SEQ ID NO: 140

(i) SEQUENCE CHARACTERISTICS:
        (A) LENGTH: 21
        (B) TYPE: Nucleic Acid
        (C) STRANDEDNESS: Single
        (D) TOPOLOGY: Linear (xi) SEQUENCE DESCRIPTION: SEQ ID NO: 140

ATCAGGCAAA AACGAACAAA C                                        21

(2) INFORMATION FOR SEQ ID NO: 141

(i) SEQUENCE CHARACTERISTICS:
        (A) LENGTH: 17
        (B) TYPE: Nucleic Acid
        (C) STRANDEDNESS: Single
        (D) TOPOLOGY: Linear (xi) SEQUENCE DESCRIPTION: SEQ ID NO: 141

CGGCATCCCA AAGTGAC                                                    17

(2) INFORMATION FOR SEQ ID NO: 142

(i) SEQUENCE CHARACTERISTICS:
         (A) LENGTH: 24
         (B) TYPE: Nucleic Acid
         (C) STRANDEDNESS: Single
         (D) TOPOLOGY: Linear (xi) SEQUENCE DESCRIPTION: SEQ ID NO: 142

CAGAGAGGGC AGCACCTTGG ACAG                                            24

(2) INFORMATION FOR SEQ ID NO: 143

(i) SEQUENCE CHARACTERISTICS:
         (A) LENGTH: 23
         (B) TYPE: Nucleic Acid
         (C) STRANDEDNESS: Single
         (D) TOPOLOGY: Linear (xi) SEQUENCE DESCRIPTION: SEQ ID NO: 143

GGCTTCACCT GCTCCCGTTT CAG                                             23

(2) INFORMATION FOR SEQ ID NO: 144

(i) SEQUENCE CHARACTERISTICS:
         (A) LENGTH: 22
         (B) TYPE: Nucleic Acid
         (C) STRANDEDNESS: Single
         (D) TOPOLOGY: Linear (xi) SEQUENCE DESCRIPTION: SEQ ID NO: 144

TCTGCCCATT CCCCAGCCTC TC                                              22

(2) INFORMATION FOR SEQ ID NO: 145

(i) SEQUENCE CHARACTERISTICS:
         (A) LENGTH: 24
         (B) TYPE: Nucleic Acid
         (C) STRANDEDNESS: Single
         (D) TOPOLOGY: Linear (xi) SEQUENCE DESCRIPTION: SEQ ID NO: 145

TACCGCGTGG CATTCAAGCA TAGC                                            24

(2) INFORMATION FOR SEQ ID NO: 146

(i) SEQUENCE CHARACTERISTICS:
         (A) LENGTH: 18
         (B) TYPE: Nucleic Acid
         (C) STRANDEDNESS: Single
         (D) TOPOLOGY: Linear (xi) SEQUENCE DESCRIPTION: SEQ ID NO: 146

TCCAGTCTGG GTGACAAA                                                   18

(2) INFORMATION FOR SEQ ID NO: 147

(i) SEQUENCE CHARACTERISTICS:
         (A) LENGTH: 20
         (B) TYPE: Nucleic Acid

```
    (C) STRANDEDNESS: Single
    (D) TOPOLOGY: Linear (xi) SEQUENCE DESCRIPTION: SEQ ID NO: 147

CAATCCACTC CACTCCTCTA                                              20
```

MATERIALS AND METHODS FOR IDENTIFYING AND ANALYZING INTERMEDIATE TANDEM REPEAT DNA MARKERS

CROSS-REFERENCE TO RELATED APPLICATIONS

This application is a divisional application of U.S. patent application Ser. No. 09/018,584, filed Feb. 4, 1998, now U.S. Pat. No. 6,238,863, issued May 29, 2001.

STATEMENT REGARDING FEDERALLY SPONSORED RESEARCH OR DEVELOPMENT

This invention was made with support from the United States Government, under Small Business Innovation Research Grant Numbers 1-43-MH5294-01 and 1-43-MH5294-02, awarded by the National Institutes of Health. The United States Government has certain rights in the invention.

FIELD OF THE INVENTION

The present invention is generally directed to the identification and analysis of genetic markers in a genomic system. The present invention is more specifically directed to the identification of loci in DNA, particularly in genomic DNA, containing length polymorphisms due to variations in the number of intermediate (5 to 7 base) sequence repeats. The present invention is also directed to the detection of such polymorphic loci. The invention is directed, furthermore, to methods of identifying and distinguishing individuals based primarily on differences in size of the products of amplifying genomic DNA at such a locus, wherein the number of intermediate tandem repeat sequences vary from one individual to another.

BACKGROUND OF THE INVENTION

DNA typing is commonly used to identify the parentage of human children, and to confirm the lineage of horses, dogs, and other prize animals. DNA typing is also commonly employed to identify the source of blood, saliva, semen, and other tissue found at a crime scene. DNA typing methods in use today are designed to detect and analyze differences in the length and/or sequence of one or more regions of DNA known to appear in at least two different forms in a population. DNA typing is also employed in clinical settings to determine success or failure of bone marrow transplantation and presence of particular cancerous tissues. Such length and/or sequence variation is referred to as "polymorphism." Any region (i.e. "locus") of DNA in which such a variation occurs is referred to as a "polymorphic locus." Most DNA typing techniques employ at least one "marker" containing the at least one such polymorphic locus. Each individual marker contains a single allele of genomic DNA ultimately derived from a single individual in a population. The methods and materials of the present invention are all designed for use in the detection of a particular class of polymorphisms in DNA characterized primarily by variation in length.

Genetic markers which are sufficiently polymorphic with respect to length or sequence have long been sought for use in identity applications, such as paternity testing and identification of tissue samples collected for forensic analysis. The discovery and development of such markers and methods for analyzing such markers have gone through several phases of development over the last several years. In recent years, the discovery and development of polymorphic short tandem repeats (STRs) as genetic markers has stimulated progress in the development of linkage maps, the identification and characterization of diseased genes, and the simplification and precision of DNA typing. The term "short tandem repeat" or "STR" as used herein refers to all sequences between two and seven nucleotides long which are repeated perfectly, or nearly perfectly in tandem within the genomic DNA of any organism. See, for example, the definition of "short tandem repeat" applied to human genomic DNA in U.S. Pat. No. 5,364,759, column 4, line 58 et seq.

The first identified DNA variant markers were simple base substitutions, i.e. simple sequence polymorphisms, which were most often detected by Southern hybridization assays. For examples of references describing the identification of such markers, designed to be used to analyze restriction endonuclease-digested DNA with radioactive probes, see: Southern, E. M. (1975), J. Mol. Biol. 98(3):503–507; Schumm, et al. (1988), *American Journal of Human Genetics* 42:143–159; and Wyman, A. and White, R. (1980) *Proc. Natl. Acad. Sci, U.S.A.* 77:6754–6758.

The next generation of markers were size variants, i.e. length polymorphisms, specifically "variable number of tandem repeat" (VNTR) markers (Nakamura Y., et al. (1987), *Science* 235:1616–1622; and U.S. Pat. No. 4,963,663 issued to White et al. (1990); U.S. Pat. No. 5,411,859 continuation of U.S. Pat. No. 4,963,663 issued to White et al. (1995)) and "minisatellite" markers (Jeffreys et al. (1985a), *Nature* 314:67–73; Jeffreys et al. (1985b) *Nature* 316:76–79., U.S. Pat. No. 5,175,082 for an invention by Jeffreys). Both VNTR and minisatellite markers, contain regions of nearly identical sequences repeated in tandem fashion. The core repeat sequence is 10 to 70 bases in length, with shorter core repeat sequences referred to as "minisatellite" repeats and longer repeats referred to as VNTRs. Different individuals in a human population contain different numbers of these repeats. These markers are more highly polymorphic than base substitution polymorphisms, sometimes displaying up to forty or more alleles at a single genetic locus. However, the tedious process of restriction enzyme digestion and subsequent Southern hybridization analysis are still required to detect and analyze most such markers.

The next advance involved the joining of the polymerase chain reaction (PCR) (U.S. Pat. No. 4,683,202 by Mullis, K. B.) technology with the analysis of VNTR loci (Kasai K, et al. (1990) Journal Forensic Science 35(5):1196–1200). Amplifiable VNTR loci were discovered, which could be detected without the need for Southern transfer. The amplified products are separated through agarose or polyacrylamide gels and detected by incorporation of radioactivity during the amplification or by post-staining with silver or ethidium bromide. However, PCR can only be used to amplify relatively small DNA segments reliably, i.e. only reliably amplifying DNA segments under 3,000 bases in length Ponce, M & Micol, L. (1992) NAR 20(3):623; Decorte R, et al. (1990) DNA Cell Biol. 9(6):461–469). Consequently, very few amplifiable VNTRs have been developed, making them, as a class, impractical for linkage mapping.

With the recent development of polymorphic markers with polymorphic dinucleotide repeats (Litt and Luty (1989) *Am J. Hum Genet* 3(4):599–605; Tautz, D (1989) NAR 17:6463–6471; Weber and May (1989) *Am J Hum Genet* 44:388–396; German Pat. No. DE 38 34 636 C2, inventor Tautz, D; U.S. Pat. No. 5,582,979 filed by Weber, L.) and with polymorphic short tandem repeats (STR) (Edwards, A., et al. (1991) *Am. J. Hum. Genet.* 49:746–756.; Hammond, H. A., et al. (1994) *Am. J. Hum. Genet.* 55:175–189; Fregeau, C. J.; and Fourney, R. M. (1993) *BioTechniques* 15(1):100–119.; Schumm, J. W. et al. (1994) in *The Fourth International Symposium on Human Identification* 1993, pp. 177–187; and U.S. Pat. No. 5,364,759 by Caskey et al.; German Pat. No. DE 38 34 636 C2 by Tautz, D.) many of the deficiencies of previous methods have been overcome. The two types of markers, those containing dinucleotide or STR repeats (which by definition include 2–7 bp repeats), are generally referred to as "microsatellite" markers. Often considered to be the best available markers, the microsatellite loci are similar to amplifiable VNTRs, in that their alleles may be differentiated based on length variation. However, unlike VNTRs, these loci contain perfect or imperfect repeat sequences two, three, four, or rarely, five bases long. They display from just a few alleles to more than forty at a single locus. Amplification protocols can be designed to produce small products, generally from 60 to 400 base pairs long, and alleles from each locus are often contained within a range of less than 50 bp. This allows simultaneous electrophoretic analysis of several systems on the same gel by careful design of PCR primers such that all potential amplification products from an individual system do not overlap the range of alleles of other systems in the same gel.

Three significant drawbacks relate to the use of microsatellite loci. First, the presence of stutter artifacts, that is, one or more minor fragments in additional to the major fragment representing each allele, is often seen following amplification. This deficiency is much more severely displayed with dinucleotide repeat loci than with tri- or tetra-nucleotide repeat markers (Edwards et al., 1991. Am J Hum Genet 49;746–756; Edwards et al., 1992. Genomics 12:241–253; Weber & May, 1989. Am J Hum Genet 44:388–396). The presence of these artifacts, presumed to result from a DNA polymerase-related phenomenon called repeat slippage (Levinson & Gutman, 1987. Mol. Biol. Evol. 4(3):203–221; Schlotterer & Tautz, 1992. NAR 20:211–215), complicates the interpretation of allelic content of the loci. While complicating all interpretations, the presence of major and minor fragments to represent each allele especially limits the usefulness of these markers in forensic analysis which often require determination of whether more than one source of DNA sample is present. Many of the markers described in this work represent a new class of markers which produce significantly less stutter artifact than known markers.

A second drawback to current STR and microsatellite marker systems relates to the difficulty in separating multiple loci in a single gel. This occurs because there is spacial compression of fragments of different size in the upper regions of the gels most commonly used for separation of DNA fragments by those skilled in the art. Development of the markers described in this work, based on larger repeat units, extends the useful range within these gels, allowing simultaneous analysis of more loci.

A third drawback is that, prior to the invention disclosed herein, only a few DNA loci of human genomic DNA had been described in the literature, with length polymorphisms based on variations in a number of five to seven base repeats at each such locus. See, e.g. Edwards et al. (1991) *Nucleic Acids Res.* 19:4791; Chen et al. (1993) *Genomics* 15(3): 621–5; Harada et al. (1994) *Am. J. Hum. Genet.* 55:175–189; Comings et al. (1995), *Genomics* 29(2):390–6; and Utah Marker Development Group (1995), *Am. J. Genet* 57:619–628. In 1995, Jurka and Pethiyagoda published an article describing a study in which they had used the GenBank database to determine the relative abundance and variability of pentameric and hexameric tandem repeats in the primate genome (Jurka and Pethiyagoda (1995) *J. Mol. Evol.* 40:120–126). However, variability was only indirectly estimated, and polymorphism levels at individual loci were not demonstrated. Id. We have developed materials and methods for identifying and analyzing DNA loci which contain highly polymorphic repeats of five to seven base repeats.

The materials and methods of the present method are designed for use in identifying and analyzing particular polymorphic loci of DNA of various types, including single-stranded and double-stranded DNA from a variety of different sources. The present invention represents a significant improvement over existing technology, bringing increased power and precision to DNA profiling for linkage analysis, criminal justice, paternity testing, and other forensic and medical uses.

BRIEF SUMMARY OF THE INVENTION

It is, therefore, an object of the present invention to provide materials and methods for the identification and analysis of DNA loci with intermediate tandem repeat sequences, wherein an "intermediate tandem repeat sequence" is a region of DNA which contains at least one repeat unit consisting of a sequence of five (5), six (6), or seven (7) bases repeated in tandem at least two (2) times.

Another object of the present invention is to provide materials and methods for identifying intermediate tandem repeat DNA markers, which produce fewer artifacts when used to analyze or detect one or more loci of a DNA sample containing an intermediate tandem repeat. The methods and materials of the present invention are preferably used to identify and analyze loci of genomic DNA, each of which contains a polymorphic intermediate tandem repeat sequence. The materials of this invention include oligonucleotide primers and DNA markers to such loci of human genomic DNA. Intermediate tandem repeat loci detected using methods of the present invention exhibit fewer artifacts than do many known loci detected using similar methods, including short STR's (i.e. tandem repeats of a two, three or four base DNA sequence).

A particular object of the present invention is to provide a method and materials for the analysis of individual polymorphic genetic loci based primarily on length variation due primarily to differences in the number of nucleic acid repeat units in a region of intermediate nucleic acid tandem repeats. It is also a specific object of the present invention to provide a method, a kit, and primers for the detection and analysis of a polymorphic loci of genomic DNA, containing intermediate tandem repeat polymorphisms, including pentanucleotide tandem repeat polymorphisms.

One embodiment of the present invention consists of a method of isolating a fragment of DNA containing an intermediate tandem repeat sequence from genomic DNA, comprising: (a) providing a plurality of fragments of DNA, wherein at least one fragment contains an intermediate tandem repeat sequence; (b) providing a support means, e.g. a stationary support means, having associated therewith at least one oligonucleotide comprising a sequence of nucleotides which is complementary to a portion of the intermediate tandem repeat sequence; and (c) combining the plurality of fragments of DNA with the support means under conditions wherein the DNA fragment containing the intermediate repeat sequence and at least one other DNA fragment hybridizes to the support means.

An alternative embodiment of the invention is a method for detecting a polymorphic intermediate tandem repeat sequence having a low incidence of stutter artifacts in genomic DNA, comprising: (a) providing a sample of DNA having at least one target intermediate tandem repeat sequence, and (b) detecting the target intermediate tandem repeat sequence in the sample of DNA, wherein an average stutter artifact of no more than 1.1% is observed.

An additional embodiment of the invention is a method for detecting a target intermediate tandem repeat sequence in a DNA sample using at least one oligonucleotide primer to amplify an intermediate tandem repeat sequence of interest (hereinafter, the "target intermediate tandem repeat sequence) in the sample DNA, wherein the oligonucleotide primer comprises a sequence which is complementary to and flanks a region of a DNA marker containing an intermediate tandem repeat sequence (hereinafter, the "template intermediate tandem repeat sequence") in the DNA marker sequence, wherein the DNA marker has a sequence selected from the group of sequences consisting of SEQ ID NO's: 1 through 43.

In another embodiment, the invention is a kit for the detection of at least one target intermediate tandem repeat sequence in a sample of DNA, the kit comprising a container which has at least one oligonucleotide primer for amplifying the at least one target intermediate tandem repeat sequence, wherein the oligonucleotide primer comprises a sequence of nucleotides which is complementary to and flanks a portion of a region of a double-stranded DNA marker containing a template intermediate tandem repeat sequence, wherein the DNA marker has a sequence selected from the group consisting of SEQ ID NO:'s 1 through 43.

In yet another embodiment, the invention is an oligonucleotide primer comprising a sequence complementary to a strand of a double-stranded DNA marker in a region of the marker flanking a template intermediate tandem repeat sequence, wherein the DNA marker has a sequence selected from the group consisting of: SEQ ID NO:'s 1 through 6, and SEQ ID NO:'s 28 through 33.

Each of the various embodiments of the present invention have specific use in the fields of human and other organism identification, forensic analysis, paternity determination, monitoring of bone marrow transplantation, linkage mapping, and detection of genetic diseases and cancers. The need to distinguish accurately between small amounts of tissue of different individuals is particularly acute in forensics applications, where many convictions (and acquittals) depend on DNA typing analysis, including the analysis of STR loci.

Further objects, features, and advantages of the invention will be apparent from the following best mode for carrying out the invention and the illustrative drawings.

Figure 1:
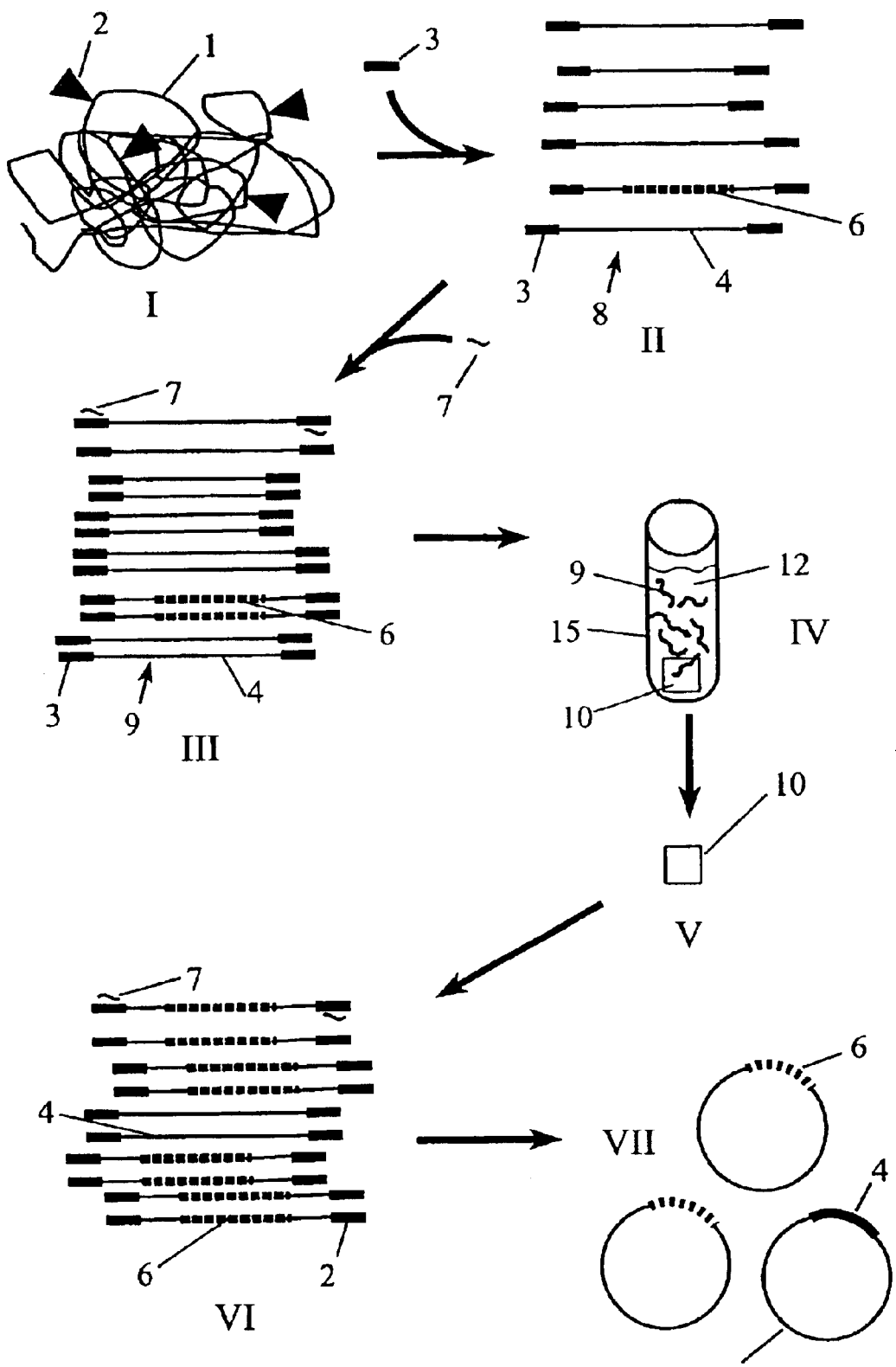
FIG. 1 is a flow diagram of a method of intermediate tandem repeat enrichment by filter hybridization.

The drawings and figures are not necessarily to scale and certain features of the invention may be exaggerated in scale or shown in schematic form in the interest of clarity and conciseness.

DETAILED DESCRIPTION OF THE INVENTION

It will be readily apparent to one skilled in the art that various substitutions and modifications may be made to the invention disclosed herein without departing from the scope and the spirit of the invention.

A. Definitions:

As used herein, the term "intermediate tandem repeat" or "ITR" refers to a region of a DNA sequence comprising a five to seven base sequence repeated in tandem at least two times. The term ITR also encompasses a region of DNA wherein more than a single five to seven base sequence is repeated in tandem or with intervening bases, provided that at least one of the sequences is repeated at least two times in tandem. Each sequence repeated at least once within an ITR is referred to herein as a "repeat unit."

An "ITR polymorphism" refers an ITR in genomic DNA which varies in length from one chromosome to another in a population of individuals, due primarily to differences in the number of repeat units in the same region of each chromosome.

The intermediate tandem repeat sequences identified and analyzed according to the present invention can be divided into two general categories, perfect and imperfect. The term "perfect" ITR, as used herein, refers to a region of double-stranded DNA containing a single five to seven base repeat unit repeated in tandem at least two times, e.g. $(AAAAT)_{12}$. The term "imperfect" ITR, as used herein, refers to a region of DNA containing at least two tandem repeats of a perfect repeat unit and at least one repeat of an imperfect repeat unit, wherein the imperfect repeat unit consists of a DNA sequence which could result from one, two, or three base insertions, deletions, or substitutions in the sequence of the perfect repeat unit, e.g. $(AAAAT)_{12}(AAAAAT)_5 AAT (AAATT)_4$. Every imperfect ITR sequence contains at least one perfect ITR sequence. Specifically, every ITR sequence, whether perfect or imperfect, includes at least one repeat unit sequence appearing at least two times in tandem, a repeat unit sequence which can be represented by formula (I):

$$A_w G_x T_y C_z)_n \tag{I}$$

wherein A, G, T, and C represent the nucleotides which can be in any order; w, x, y and z represent the number of each nucleotide in the sequence and range from 0 to 7 with the sum of w+x+y+z ranging between 5 and 7; and n represents the number of times the sequence is tandemly repeated and is at least 2.

"Pentanucleotide tandem repeat" refers to a subclass of the "intermediate tandem repeat" polymorphisms defined above. Unless specified otherwise, the term "pentanucleotide tandem repeat" encompasses perfect ITRs wherein the repeat unit is a five base sequence, and imperfect ITRs wherein at least one repeat unit is a five base repeat.

"DNA Marker" refers to a fragment of DNA which contains an ITR sequence such as a fragment of DNA containing an ITR sequence produced by amplifying a region of genomic DNA. Each individual marker contains a single allele of genomic DNA ultimately derived from a single individual in a population.

The term "locus" refers to a specific region of DNA. When used to describe a region of genomic DNA, "locus" refers to a particular position on a chromosome. The same genomic locus appears at identical sites on each pair of homologous chromosomes for any individual in a population. The sequence of DNA at the same locus on each such chromosome, or at the same locus of DNA originating from the same such chromosome, is referred to as an "allele."

The term "polymorphism", as used herein refers to variations in the alleles at a locus seen in at least two chromosomes found in the genomic DNA of a population of individual organisms of the same species. The term "polymorphism" includes variations in the sequence of DNA obtained from the same locus of fragments of chromosomes cloned into other vehicles, such as DNA vectors or the chromosomal DNA of another organism.

As used herein, "ITR flanking sequence" refers to the nucleotide sequence adjacent to an ITR on a strand of DNA sequence containing an ITR. Sequences which include the ITR flanking sequence as a portion of their entire sequence are themselves flanking sequences.

The term "oligonucleotide primer" as used herein defines a molecule comprised of more than three deoxyribonucleotides or ribonucleotides. Although each primer sequence need not reflect the exact sequence of the template, the more closely the sequence reflects the complementarity to a template, the better the binding to the template. Its exact length and sequence will depend on many factors relating to the ultimate function and use of the oligonucleotide primer, including temperature, sequence of the primer, and use of the method. Each oligonucleotide primer of the present invention comprises a sequence of nucleic acids which is complementary to the sequence of a DNA marker flanking an ITR sequence. The oligonucleotide primers of the present invention are capable of acting as an initiation point for synthesis when placed under conditions which induce synthesis of a primer extension product complementary to a nucleic acid strand. The conditions can include the presence of nucleotides and an inducing agent, such as a DNA polymerase at a suitable temperature and pH. In the preferred embodiment, the primer is a single-stranded oligodeoxyribonuclotide of sufficient length to prime the synthesis of an extension product from a specific sequence in the presence of an inducing agent. Sensitivity and specificity of the oligonucleotide primers are determined by the primer length and uniqueness of sequence within a given sample of template DNA. In the present invention the oligonucleotide primers are usually about greater than 15 bases and preferably about 20 to 40 bases in length.

The term "oligonucleotide primer pair" refers to a pair of primers, each comprising a sequence of deoxyribonucleotide or ribonucleotide bases complementary to opposite strands of double-stranded DNA flanking the same ITR. Each pair of oligonucleotide primers of the present invention is preferably selected to detect a single ITR. Although each primer sequence need not reflect the exact sequence of the template, the more closely the sequence reflects the complementarity to a template, the better the binding to the template.

The term "extension product" refers to the nucleotide sequence which is synthesized from the 3' end of the oligonucleotide primer and which is complementary to the strand to which the oligonucleotide is bound.

The term "oligonucleotide probe", as used herein, refers to a single-stranded molecule of DNA or RNA comprising a sequence which is complementary to a portion of a target sequence, such as the intermediate tandem repeat sequence of a DNA sample, wherein the portion of complementarity is of sufficient length to enable the probe to hybridize to the target sequence.

The term "stutter artifact", as used herein, refers to a particular type of artifact observed when detecting one or more molecules of target DNA, wherein the target DNA contains tandem repeats of the same repeat unit sequence, including the target intermediate tandem repeat sequences detected and analyzed according to the present invention. When a sample containing any such target DNA is detected after separation of all DNA in the sample by length, e.g. using gel electrophoresis, each molecule of target DNA produces a major signal (e.g. a major band on a gel); but, a minor signal can be detected proximate to each major signal. The minor signal is generally produced from the detection of DNA fragments which differ from the target DNA in length due to the addition or deletion of one or more repeat units from the target DNA sequence. Stutter artifacts have been attributed to slipped-strand mispairing during replication of DNA, both in vivo and in vitro. See, e.g. Levinson and Gutman (1987), *Mol. Biol. Evol,* 4(3):203–221; and Schlötterer and Tautz (1992), *Nucleic Acids Research* 20(2): 211–215. Such artifacts are particularly apparent when DNA containing any such repeat sequence is amplified in vitro, using a method of amplification such as the polymerase chain reaction (PCR), as any minor fragment present in a sample or produced during polymerization is amplified along with the major fragments.

The term "% stutter artifact" as used herein refers to a comparison of the amplitude of a minor (i.e. artifact) signal to the amplitude of a major (i.e. target) signal observed in a sample of DNA obtained from a single source, such as a single colony of bacteria or a single chromosome of genomic DNA. % stutter artifact can be determined on DNA which has not been amplified; but, is preferably determined after amplification of at least one target intermediate tandem repeat sequence. The term "average % stutter artifact" refers to an average of % stutter artifacts obtained from the measurements of % stutter artifact detected from a representative sample of at least twenty alleles in a population.

The term "genomic DNA" as used herein refers to any DNA ultimately derived from the DNA of a genome. The term includes, for example, cloned DNA in a heterologous organism, whole genomic DNA, and partial genomic DNA (e.g. the DNA of a single isolated chromosome).

The DNA detected or isolated according to the present invention can be single-stranded or double-stranded. For example, single-stranded DNA suitable for use in the present invention can be obtained from bacteriophage, bacteria, or fragments of genomic DNA. Double-stranded DNA suitable for use in the present invention can be obtained from any one of a number of different sources containing DNA with intermediate tandem repeat sequences, including phage libraries, cosmid libraries, and bacterial genomic or plasmid DNA, and DNA isolated from any eukaryotic organism, including human genomic DNA. The DNA is preferably obtained from human genomic DNA. Any one of a number of different sources of human genomic DNA can be used, including medical or forensic samples, such as blood, semen, vaginal swabs, tissue, hair, saliva, urine, and mixtures of bodily fluids. Such samples can be fresh, old, dried, and/or partially degraded. The samples can be collected from evidence at the scene of a crime.

B. Method of Isolating Polymorphic DNA Markers Containing an ITR:

One embodiment of the present invention is a method for isolating a fragment of DNA containing an ITR, using hybridization selection. The method comprises the steps of: (a) providing a plurality of fragments of DNA, wherein at least one DNA fragment contains an ITR; (b) providing a support means having at least one oligonucleotide associated therewith, wherein the oligonucleotide includes a sequence of nucleotides which is complementary to a portion of the intermediate tandem repeat sequence; and (c) combining the plurality of fragments of DNA with the support means under conditions wherein DNA fragments, including any DNA fragments containing the ITR sequence, hybridize to the support means.

The plurality of fragments of DNA provided in step (a) of the method can be obtained by fragmenting any sample of DNA containing an ITR, but are preferably obtained by fragmenting genomic DNA. See, e.g. Current Protocols in Human Genetics (1994), Chapter 2: Development of Genetic Markers, Construction of Small-Insert Libraries from Genomic DNA, p. 2.2.1 et seq., which is incorporated herein by reference. The most preferred method for preparing a plurality of fragments of DNA for use in step (a) is according to the steps comprising: fragmenting a sample of DNA, thereby producing a population DNA fragments wherein at least one DNA fragment contains the ITR; ligating a linker containing a priming sequence to at least one end of each DNA fragment in the population DNA fragments; and amplifying each linker ligated fragment using an oligonucleotide primer comprising a sequence which is complementary to the priming sequence. A different linker can be ligated to each end of each fragment. However, a single linker is preferably ligated to each end to enable amplification using a single oligonucleotide primer having a sequence which is complementary to the priming sequence of the linker. Linker ligation is preferably conducted in the presence of a ligase enzyme, such as T4 DNA ligase.

Any one of a number of different means can be used to produce the plurality of DNA fragments provided in step (a) of the method, including sonication or fragmentation with at least one restriction enzyme, although only double-stranded DNA can be fragmented with a restriction enzyme. When a restriction enzyme is used to fragment a sample of double-stranded DNA, it is preferably a restriction enzyme with a four base pair recognition sequence, which leaves single-stranded overhangs, and which does not cut the DNA sample within the ITR region of interest. Preferred restriction enzymes for use in fragmenting a double-stranded DNA sample include Mbo I, Aci I, Bfa I, Dpn II, Hha I, Hin P1I, Hpa II, Mse I, Msp I, Nla III, Sau 3AI, Taq I, Csp 6I, and Tai I.

Linker-ligated DNA fragments produced as described above are subsequently amplified, using an amplification reaction, such as a polymerase chain reaction, (U.S. Pat. No. 4,683,202 by Mullis, K. B), nucleic acid sequence based amplification (NASBA) Kievits et al. (1991) J Virol Methods 35(3):273–286, ligation-mediated amplification (Volloch et al. (1994) Nucleic Acids Res 22(13):2507–2511, strand displacement amplification (SDA) (Walker et al. (1992) PNAC 89(1):392–396, sequence-independent single primer amplification (SISPA) (Reyes (1991) Mol Cell Probes 5(6):473–481, or ligase chain reaction (U.S. Pat. No. 5,686,272 issued to Marshall et al.

The support means provided in step (b) of the present method comprises a stationary support with at least one target oligonucleotide associated therewith. The stationary support preferably comprises a material capable of coupling with the oligonucleotide directly or indirectly. Suitable material capable of coupling directly with the oligonucleotide includes nitrocellulose, nylon, glass, silica, and latex. Examples of suitable stationary supports for use in this preferred embodiment of the present method include a nylon membrane, a filter embedded with silica particles, glass beads, silica magnetic particles, or a resin containing silica. Suitable material capable of coupling indirectly to the oligonucleotide through a first coupling agent bound to the oligonucleotide and a second coupling agent bound to the surface of the stationary support include avidin and streptavidin, or an antigen and antibody thereto.

The at least one target oligonucleotide associated with the stationary support includes a sequence of nucleotides which is complementary to a portion of the intermediate tandem repeat sequence of the DNA fragment. The term "portion" as used herein refers to a sequence of nucleotides within the ITR region of the DNA fragment of sufficient length that an oligonucleotide having a sequence complementary to the sequence would hybridize thereto when it comes into contact therewith. The "portion" is preferably a sequence of at least 20 bases in length, and more preferably a sequence of at least 40 bases. The target oligonucleotide more preferably has a sequence characterized by the formula $(A_w G_x T_y C_z)_n$, wherein A, G, T, and C represent the nucleotides which can be in any order; w, x, y and z represent the number of each nucleotide in the sequence and range from 0 to 7 with the sum of w+x+y+z ranging between 5 and 7; and n represents the number of times the sequence is tandemly repeated and is at least about 4 times, more preferably at least about 8 times, and most preferably at least about 15 times.

In step (c) of the method, the plurality of fragments of DNA is combined with the support means under conditions wherein the DNA fragment containing the ITR hybridizes to the support means. When the plurality of fragments is a plurality of fragments of double-stranded DNA, the DNA is denatured prior to hybridization to the support means. Suitable means for denaturing double-stranded DNA fragments prior to hybridization to the support means include exposing the DNA to a temperature which is sufficiently high to denature double-stranded DNA, or suspension of the DNA in a denaturing solution. The DNA is preferably denatured using a denaturing solution containing a denaturing agent, such as a base (e.g. sodium hydroxide or potassium hydroxide). When a base is used to denature the DNA fragments, the pH of the resulting mixture is preferably adjusted to about a neutral pH, preferably by adding a buffer at a pH of about 4.8 to the mixture.

Once fragments of DNA have hybridized to the support means, the support means is preferably washed to remove DNA fragments and any other material present in any solution in which the support means is contained or on the surface of the support means which are not hybridized thereto. Any wash solution used is preferably configured to remove such materials without releasing the DNA fragments hybridized to the support means.

The DNA fragments hybridized to the support means can be released, from the support means using heat or an appropriate release solution, depending upon the nature of the association between the support means and the DNA fragments. For example, water or an aqueous low salt solution such as a TE buffer (e.g. 10 mM Tris-HCl, pH 7.5, 1 mM EDTA) can be used to release DNA fragments hybridized to a support means comprised of a silica material. Once released from the support means, the DNA fragments can be processed to further isolate DNA containing the ITR sequence from other fragments of DNA present in the resulting mixture of released DNA fragments. Additional processing steps could include rehybridization and screening according to the method described above, or cloning into a DNA vector and screening the transformants of the clones.

FIG. 1 illustrates a preferred embodiment of the method of isolating a fragment of DNA containing an ITR, wherein a population of DNA fragments is prepared, hybridized to a support means, amplified, cloned, and screened for transformants containing the ITR. Each of the steps illustrated in FIG. 1 is labeled with a roman numeral. Step I shows a molecule of double-stranded DNA (1) being digested with a restriction enzyme (2), producing a population of DNA fragments (not shown) varying in size, at least one of which includes the target ITR. The arrow between Steps I and II illustrate a linker (3) being added to the population of DNA fragments to produce a population of linker-ligated fragments (8) with a linker (3) at the end of each of two different classes of DNA fragments, fragments with the target ITR sequence (6) and fragments without the target sequence (4). An oligonucleotide primer (7) having a sequence complementary to a priming sequence of each linker (3) is added to the population of DNA fragments (8) in Step III, and the population is amplified through a PCR reaction, thereby producing a population of amplified DNA fragments (9). In Step IV the population of amplified DNA fragments (9) is placed in a container (15) with a hybridization solution (12) and a filter (10) with at least one oligonucleotide having a sequence complementary to a portion of the target ITR sequence associated therewith. The hybridization solution promotes the hybridization of the DNA fragments containing the ITR sequence to the filter. In Step V, the filter (10) is removed from the container (15), and DNA fragments hybridized thereto are released therefrom. The resulting enriched population of released fragments are re-amplified in Step VI, using the same oligonucleotide primer (7) used in the amplification reaction in Step III. Finally, each fragment of the enriched amplified population of DNA fragments is cloned into a plasmid vector (18) in Step VII. The vectors are shown in Step VII cloned with fragments with the target ITR sequence (6) and cloned with fragments without the ITR sequence (4).

C. Method for Detecting a Polymorphic ITR Having Low Stutter:

Minimal stutter artifact is observed when a target ITR sequence of a DNA sample having such a sequence is detected according to this particular embodiment of the method of the present invention. The average stutter artifact observed is preferably no more than 1.1%, more preferably no more than 0.9%. The target ITR sequence can be either a perfect ITR or an imperfect ITR sequence. The DNA sample detected is preferably genomic DNA.

The average stutter artifact is preferably observed after amplification of the ITR sequence in the DNA sample.

D. Primers, Probes, and Markers

The present invention also comprises DNA markers identified in the Sequence Listing below as SEQ ID NO:'s 1–43, primers wherein each primer has a sequence which is complementary to a sequence flanking an ITR region of one of the DNA markers identified by one of those 43 sequences, and probes which have a sequence which is complementary to a sequence contained within the ITR region of one of the 43 markers. Specific preferred primers identified in experiments illustrated in the Examples, below are listed in Table 1.

TABLE I

| Marker SEQ ID NO | Clone Number | Primers SEQ ID NO | Upper Primer & Lower Primer |
|---|---|---|---|
| 1 | C074 | 44 | TGGCTCAGACACCTCATTG |
|   |   | 45 | CACCACTGTATTCCCAGTTTG |
| 2 | C221 | 46 | CACTTGCCATCCCTGCCACACA |
|   |   | 47 | AGCGCACCCCCAATTTCCGGTAT |
|   | C221 | 48 | TGGGGACATGAACACACTTTGC |
|   |   | 49 | GAGGCCCAGGACCAGATGAAAT |
|   | C221 | 50 | CACCTGTCAGGCAAGGCTTAAAC |
|   |   | 51 | CAACACTGAGCGCTTTTAGGGACT |
|   | C221 | 52 | TCAGGCAAGGCTTAAACAGGGATA |
|   |   | 53 | ACACTGAGCGGTTCTAGGGACTTC |
|   | C221 | 52 | TCAGGCAAGGCTTAAACAGGGATA |
|   |   | 54 | TGAGCGCTTCTAGGGACTTCTTCA |
|   | C221 | 55 | CCCTGCCCTACCCACTTG |
|   |   | 56 | AGGCCCAGGACCAGATGA |
|   | C221 | 57 | GGACCTGTCAGGCAAGGCTTAAAC |
|   |   | 58 | CCAGCCATGAAGTGGCTGTGAG |
| 3 | C240 | 59 | CCCGCTTCAAAGTTCCCAGTTC |
|   |   | 60 | CCTCCCATTTCAGCCTCCTGA |
| 4 | C331 | 61 | GTCTGCCACAGTGCTGGAAACTAA |
|   |   | 62 | GCACCCCAGCCTAAGGCAATA |
| 5 | C362 | 63 | GCATGGCGGAAGAAACAA |
|   |   | 64 | TGGCAACAGAGCGAGACTC |
| 6 | C390 | 65 | CCTGGGTGACAGCGAGAATCT |
|   |   | 66 | TGTCCCTTGCCTTGTCTCACTAAA |
| 7 | G022 | 67 | CAGCCTTGGTGACAGAGCAAA |
|   |   | 68 | TGTGTTGAGGGTGGGGTACAT |

TABLE I-continued

| Marker SEQ ID NO | Clone Number | Primers SEQ ID NO | Upper Primer & Lower Primer |
|---|---|---|---|
| 8 | G023 | 69 | CCTGGGCAAGAGAGCAAG |
|  |  | 70 | CACATCCCAAAACCACCCTAC |
| 9 | G025 | 71 | GCATTTCCCCTGCTTGTACT |
|  |  | 72 | GATCACATTTGCTAACGACTTCTC |
| 10 | G047 | 73 | GGCAACATATCAAGACCCCCATCTCT |
|  |  | 74 | GAAGCTGCCCCTCACCACTACATTTT |
| 11 | G065 | 75 | GATCACATTTGCTAACCACTTCTC |
|  |  | 76 | TATAAATTACCCAGTCTCAGGAAG |
| 12 | G085 | 77 | GTGATACAGCAAGCCTCATC |
|  |  | 78 | AGAGACTCCTGGAAAGATAAAAGT |
| 13 | G132 | 79 | GTCTGGAGAACAGTGGCCCTTGT |
|  |  | 80 | CAGGAAGCTGAGGCAGGAGAATCT |
| 14 | G145 | 81 | AAGGCTCCAGTGGGGTAT |
|  |  | 82 | AAAACAAGGCAGTAGTCAATAAAG |
| 15 | G152 | 83 | GGCATGAGAATCGCTTGAACCTG |
|  |  | 84 | GGCCTCCATGATGTTTCCAATGAT |
| 16 | G153 | 85 | TCAGGAGGCATGAGAATCGCTTGA |
|  |  | 86 | GGCCTCCATGATGTTTGCCAATGA |
| 17 | G158 | 87 | CTCGCCCTCTCCTATAAGCAGTTT |
|  |  | 88 | GCAGAGATAATTTG GAGTGGGATG |
| 18 | G181 | 89 | CTTGGGTGCCTGTAATCC |
|  |  | 90 | GGTAGAGCTCCCCCATCT |
| 19 | G210 | 91 | GCAGAATATTGGGGCTCATCAC |
|  |  | 92 | AAACAAGGAAAGGAGAGGAGGA |
|  | G210 | 93 | AAGGTTGTGGGATGACTACTACA |
|  |  | 94 | TGGTCAACACAGCAAGACATT |
| 20 | G212 | 95 | TCCTGCCACCTGCTTGCTTTCT |
|  |  | 96 | ATTGCACTCCAGCCTGGGTGATAC |
| 21 | G233 | 97 | CGCTTGAGCCTTGGAGATTG |
|  |  | 98 | GAGCAGTCAGAATTCAGGAGTTGT |
| 22 | G234 | 99 | TGGGCAACAAGAGCAAAACTCCAT |
|  |  | 100 | GGGACTTGGGCTGAGGGCTTTAC |
| 23 | G235 | 101 | ATATCAATATCAGGCAGCCACAGG |
|  |  | 102 | CCGTTTCAGAGCAGAGGTTTAGC |
| 24 | G331 | 103 | TCTCATTGGTTTCAAAGAACTTA |
|  |  | 104 | AGACTCCATCTCAAACAAAAGA |
| 25 | G405 | 105 | TCATGTGCATGGAGCCTGGTTCAT |
|  |  | 106 | CCCAGCCTTGGCAAGAGTGAGGT |
| 26 | G475 | 107 | GGCGACTGAGCAAGACTC |
|  |  | 108 | TTAAGCAAAGTAGCCTCAAACA |
|  | G475 | 109 | GGGCGACTGAGCAAGACTC |
|  |  | 110 | ACTCATTACCTTGCATGCATGATA |
|  | G475 | 107 | GGCGACTGAGCAAGACTC |
|  |  | 111 | CATTACCTTGCATGCATGATA |
| 27 | G539 | 112 | TGGGCAACAGAGTAAGACTCA |
|  |  | 113 | GTTCAGTACCGTTCACCTCTTTA |
|  | G539 | 114 | GTAAGACTCAGTCTCCAAAAAAAAAAAAAG |
|  |  | 115 | AGGAATGGTTTCTCTGTTAGTAAATGGT |
| 28 | S023 | 116 | CAGCCTGGGCAACAAGAATGAAAC |
|  |  | 117 | TGGCCCCTGCAGCGGAGTC |
| 29 | S071 | 118 | GAATTCATTTGCGGAAAGATT |
|  |  | 119 | GTAGGGAGGGTGGAGTATTCA |
| 30 | S085 | 120 | AGAGCAAGACCCCGTCTCAT |
|  |  | 121 | AGTCGATGGGCCTTTTAACA |
| 31 | S125 | 122 | GAGAATCACTTGAACCCAGGAAG |
|  |  | 123 | AGAACCAGCTGTTAGTTTCGTTGA |
| 32 | S132 | 124 | GGTTGCAGTGAGGGGAGATAAGAGT |
|  |  | 125 | TGTGCCAGGAACCAGAAATTTACAG |
| 33 | S136 | 126 | GGCCCAAGGTTACTTTTCAC |
|  |  | 127 | GGGCCACTGCACTCCT |
| 34 | S159 | 128 | CATGGTGAGGCTGAAGTAGGAT |
|  |  | 129 | GTGGCGTGTCTTTTTACTTTCTTTA |
| 35 | S176 | 130 | AGGCAGCCCAGGAACAAT |
|  |  | 131 | CCAAGATAGCGGCCAAGATAGT |
| 36 | S189 | 132 | GAGGGCAGCTGGGATGTTACTCTT |
|  |  | 133 | TGCCCTGTTTGGAGAACTGTAGGT |
| 37 | S199 | 134 | GTCCCCAGAAACAGATGTA |
|  |  | 135 | GTGAGCCGAGATTGTATCAT |
| 38 | S040 | 136 | TCGGGGACAGGGCTTACTC |
|  |  | 137 | ATCATTGTCGCTGCTACTTTATCG |
| 39 | S066 | 138 | CTACTCTACCCCATTTCATTC |
|  |  | 139 | GTAGAGTGGAGTGGATGAGA |
| 40 | S077 | 140 | ATCAGGCAAAAACGAACAAAC |
|  |  | 141 | CGGCATCCCAAAGTGAC |
| 41 | S097 | 142 | CAGAGAGGGCAGCACCTTGGACAG |
|  |  | 143 | GGCTTCACCTGCTCCCGTTTCAG |

TABLE I-continued

| Marker SEQ ID NO | Clone Number | Primers SEQ ID NO | Upper Primer & Lower Primer |
|---|---|---|---|
| 42 | S103 | 144 | TCTGCCCATTCCCCAGCCTCTC |
|  |  | 145 | TACCGCGTGGCATTCAAGCATAGC |
| 43 | S110 | 146 | TCGAGTCTGGGTGACAAA |
|  |  | 147 | CAATCCACTCCACTCGTCTA |

The following examples are offered by way of illustration, and are not intended to limit the invention in any manner. In the examples, all percentages are by weight if for solids and by volume if for liquids, and all temperatures are in degrees Celsius unless otherwise noted.

EXAMPLE 1

Construction of Whole Genome PCR Library

The particular amplification and hybridization selection techniques used in this Example, and in Example 2, below, are modified forms of a selection method described in Armor, J. et al. (1994) *Hum Mol Genet* 3(4):599–605.

Human genomic DNA was purified from whole blood pooled from 15 individuals using standard phenol:chloroform extraction procedures (*Current Protocols in Human Genetics* (1994), Gilber, J. ed., Appendix).

Approximately 100 μg genomic DNA was cut with 5 units of Mbo I restriction enzyme per μg of DNA for 16 hrs at 37° C., followed by purification with by phenol:chloroform extraction, ethanol precipitation and resuspended in 100 μl of TE Buffer (10 mM Tris-HCl, 1 mM EDTA, pH 8.0) for a final concentration of about 1 μg/μl of DNA.

DNA fragments ranging in size from 250–600 bp were isolated by gel electrophoresis on a 1% SeaKem GTG (FMC Bio Products, Rockland, Me.) preparative agarose gel (15× 20 cm) for 1.25 hours at 100 volts and recovered by electroelution (reference). The DNA was quantified by measuring absorbance at $A_{260}$ and diluted to 500 ng/μl in sterile nanopure water and stored at −20° C.

Linkers were prepared by annealing equimolar amounts of oligo A (5'-GCG GTA CCC GGG AAG CTT GG-3') and 5' phosphorylated oligo B (5'-GAT CCC AAG CTT CCC GGG TAC CGC-3') for a final concentration of 1,000 pmol/μl. One μg of size selected insert DNA (3.5 pmols with an average size of 425 bp) was ligated to 13 μg (875 pmols) of linkers (250:1 linker:insert molar ratio), using 1–3 units of T4 DNA ligase for 16 hr at 15° C. Excess linkers and linker dimers were separated from the primary fragments by gel electrophoresis (1% SeaKem GTG agarose, 1.5 hrs at 100 volts). The linker-ligated DNA fragments were recovered from the gel by electroelution, and resuspend in 50 μl sterile water.

DNA (50 ng) with ligated linkers were amplified using a PCR in 100 μl reaction volume containing 10 μl of a 10×STR buffer (500 mM KCl, 100 mM Tris-HCl, pH 9.0, 15 mM $MgCl_2$, 1% Trition X-100, and 2 mM of each dNTP), 1 μl Taq polymerase (5U/μl), and 1 μM oligo A primer (10 μl of a 10 pmol/μl stock). The "oligo A" used as a primer in this reaction is the same "oligo A" used to assemble the Mbo I linker, as described above. Cycling conditions were 95° C. 1 min, 67° C. 1 min, 70° C. 2 min; for 30 cycles. The dNTPs, primers and primer dimers were removed by microfiltration with Centricon-100s (add 2 ml sterile water to sample and load Centricon-100, spin 20 min at 2,000 RPM, invert Centricon filter and spin for 2 min at 2,000 RPM to recover DNA, resuspend in 100 μl sterile $dH_2O$). A 5 μl aliquot of the resulting PCR library was checked on 1% agarose gel (1 hr at 100 volts) to confirm that the size range was between 250 and 600 bp.

EXAMPLE 2

Enrichment for Pentanucleotide Repeats by Hybridization Selection

DNA fragments from the whole genome PCR library produced according to Example 1 containing various different repeats were enriched by hybridization using different oligonucleotide mixtures associated with a solid support. Fragments containing $(AAAAX)_n$ pentanucleotide repeats were enriched by hybridization selection. This process was accomplished by first constructing oligonucleotides for use in hybridization selection that consisted of tandem arrays of $(AAAAC)_n$, $(AAAAG)_n$ and $(AAAAT)_n$ around 1000 bp in length. These oligonucleotides were fixed to membranes and hybridized to the whole genome PCR library to select those fragments containing $(AAAAX)_n$ repeats.

The array of oligonucleotides was constructed as follows: (a) 5'-phosphorylated 30 mer oligonucleotides of [AAAAC]$_6$, [AAAAG]$_6$ and [AAAAT]$_6$ and their complements [GTTTT]$_6$, [CTTTT]$_6$ and [ATTTT]$_6$ were synthesized and suspended in nanopure water at a concentration of 1,000 pmol/μl, (b) equal molar concentration (used 10 μl or 10 nmol or 198 μg each) of oligonucleotides having complementary sequences were combined, heated to 65° C. for 15 minutes and left at 4° C. for a few hours to anneal to one another, (c) the annealed oligonucleotides were then ligated to one another using 1 Weiss Unit of T4 DNA ligase per μg DNA at 15° C. overnight, (d) concantomers ≧200 bp were size-selected on 1% SeaKem GTG agarose, (e) the ligated DNA was subjected to primer-free PCR to lengthen the tandem arrays, (f) fragments of apparent size over 1000 bp were recovered from 1% agarose gels and purified by microfiltration. The absorbance at $A_{260}$ was determined and a one μg/μl stock was made in sterile nanopure water.

A total of one μg of $(AAAAC)_{200}$, $(AAAAG)_{200}$, or $(AAAAT)_{200}$ oligonucleotide was then spotted onto 4 mm×4 mm pieces of nylon Hybond-Nfp membrane (Amersham Life Sciences, Inc.) filter, washed twice in pre-hybridization buffer for 30 minutes with agitation to remove weakly bounded oligos, allowed to air dry, UV cross-linked at 1200 μJoules to bind DNA, then stored at −20° C.

Hybridization selection of the whole genome PCR library to the resulting support medium of oligonucleotides associated with the nylon filter described above was accomplished as follows: (a) the filters were prehybridized in 1 ml Prehybridization Buffer [1% BSA (Sigma B-4287), 1 mM EDTA, pH 8.0, 7% (w/v) SDS, 0.5 M $Na_2HPO_4$] at 40° C. for filters containing oligonucleotides having sequences of $(AAAAC)_n$ and $(AAAAG)_n$ and at 37° C. for those containing $(AAAAT)_n$ sequences. After 20 minutes the buffer is removed and 100 μl of fresh Prehybridization Buffer is added, (b) whole Genome PCR Library DNA (20 μg) was denatured with alkali (KOH, final concentration 150 mM) and neutralized by adding 0.25 volumes of 1M Tris-HCl pH 4.8 and added to the buffer containing the filters. The resulting reaction mixture was incubated overnight at prehybridization temperatures of 37° C. or 40° C., (c) the $(AAAAC)_{200}$ and $(AAAAG)_{200}$ filters are washed 2× with 1 ml Wash Buffer #1 (40 mM Na2HPO4, pH 7.2, 0.1% SDS) at 40° C. and 1× at room temperature for 15 minutes with agitation. The $(AAAAT)_{200}$ filters are washed 1× with 1 ml Wash Buffer #1 at 37° C. and 1× at room temperature, (d) DNA bound to each filter was released by heating to 95° C. for 5 minutes in 100 μl sterile nanopure water. The sample was removed while at 95° C. to prevent re-annealing. Filters were stripped and reused by incubating in 0.4 M NaOH for 30 minutes at 45° C., then transferring to 0.1×SSC, 0.1% SDS, 0.2 M Tris pH 7.5 and incubating another 15 minutes. The membranes were blotted dry and stored in sealed tubes at −20° C.

EXAMPLE 3

Cloning Pentanucleotide Repeat Enriched Library of DNA Fragments

The population of DNA fragments enriched for pentanucleotide repeats according to Example 2 was re-amplified by PCR. The reamplified fragments were then cloned into plasmid vector pGEM-3Zf(+), as described below. This process was accomplished by ligating selected inserts to the pGEM vector then transforming circularized plasmid into a JM109 E. coli host.

The insert-vector ligations were accomplished as follows: (a) 5 μl of the hybridization selected DNA was reamplified in a 100 μl reaction volume, using a 1×STR buffer (50 mM KCl, 10 mM Tris-HCl, pH 9.0, 1.5 mM $MgCl_2$, 0.1% Triton X-100, and 0.2 mM each dNTP), 1 μl Taq polymerase (5U/μl), and 1 μM oligo A primer (1 μl of 100 pmol/μl stock). Cycling conditions were 95° C. 1 min, 67° C. 1 min, 70° C. 2 min; for 30 cycles. (b) The reamplified DNA was digested with Mbo I by adding 11 μl Promega restriction enzyme 10× Buffer C and 2 μl (8U/μl) Mbo I to the 100 μl PCR reaction, by incubating the resulting reaction mixture overnight at 37° C., and by heat inactivating the restriction enzyme by incubating the mixture at 65° C. for 20 minutes. (c) The pGEM-3Zf(+) vector (~20 μg or 10.6 pmol) was prepared for fragment insertion by digesting with BamH I (5U/μg) for 16 hours at 37° C., followed by the addition of appropriate amounts of Calf Intestinal Alkaline Phosphate 10× buffer (Promega) and 1 μl CIAP (Units/μl) and incubation for 1 hour at 37° C. This reaction was stopped by adding 0.5 M EDTA to 0.02 M final concentration then phenol extracted, ethanol precipitated and resuspend in TE buffer at 1 μg/μl. (d) Finally, 20 μl insert-vector ligations were performed by incubating 1 μl of DNA cut with MboI (see step b) along with 1 μl or 200 ng of dephosphorylated pGEM 3Zf(+) (see step c) and 1 μl T4 DNA ligase (1 to 3 U/μl) for 2 hours at room temperature.

Finally, 10 μl of the insert-vector ligation reaction were transformed into 100 μl of JM109 competent cells using the Promega transformation protocol described in Technical Bulletin #095.

EXAMPLE 4

Selection of Small Insert Genomic Library Clones Containing $(AAAAX)_n$ Pentanucleotide Repeats by Colony Hybridization Clones containing $(AAAAX)_n$ pentanucleotide repeats were selected by colony hybridization screening using Lightsmith II reagents and protocols (see Promega Technical Bulletin #TM227), and visualized by hybridization to alkaline phosphatase conjugated probes.

Colony DNA was transferred to membranes by placing MagnaGraph nylon membranes (Micron Separations, Inc. Westboro, Mass.) on plates containing bacterial colonies, allowed to sit for 3 minutes, then blotting on dry filter paper. Next, the membranes were transferred to a series of trays containing 10% SDS for 3 minutes, then denaturing solution consisting of 5 ml NaOH+30 ml 5 M NaCl+65 ml $dH_2O$ for 5 minutes, then Neutralizing solution consisting of 30 ml 5 M NaCl+25 ml M Tris-HCl, pH 7.4+45 ml $dH_2O$ for 5 minutes, and finally 2×SSC for 5 minutes. The membranes were then dried at room temperature for 30 minutes followed by UV crosslinking with 1200 μjoules, using a Statalinker® (Stratagene, La Jolla, Calif.).

Detection of colonies containing clones with $(AAAAX)_n$ repeats was accomplished with the aid of AP conjugated probes and chemiluminescence. Exposure of filters hybridized to AP conjugated probes to X-ray film indicated colonies contain desired clones. A second hybridization was performed to confirm initial results.

The detection procedure utilized Lightsmith II kit from Promega (see Promega Bulletin #TM227 for detailed description of the procedure). Briefly, the detection procedure used consisted of the steps of: (a) Incubating of the filters in a Quantum Yield® Blocking Solution (Promega Cat NO F1021) for 45 minutes at 56° C. with vigorous shaking, (b) pouring off the Blocking Solution and adding 0.05 ml of Quantum Yield® High Stringency Hybridization Solution (Promega Cat No. F1231) per $cm^2$ of membrane containing the AP probe and incubating 45 minutes at 56° C. with vigorous shaking, (c) pouring off the hybridization/ probe solution from the filters and wash filters twice with 150–200 ml of preheated Wash Solution #1 (2×SSC, 0.1% SDS) for 10 minutes at 56° C., (e) combining all filters and wash once with Wash Solution #2 (1×SSC) for 10 minutes at room temperature, (f) equilibrating the blots for 5 minutes in 200 ml of 100 mM diethanolamine, 1 mM $MgCl_2$, (f) adding sufficient 0.25 mM CDP-Star substrate (Tropix, Bedford, Mass.) to saturate filters then incubate for at least 5 minutes at room temperature, (g) placing the substrate-saturated filters on a polystyrene plastic sheet protector in a hybridization folder and closing the folder, (h) placing the hybridization folder containing the filters in a film cassette and exposing the filters contained therein to X-ray film, and (I) developing the film after at least a 1 hour period of exposure to the film.

EXAMPLE 5

DNA Sequencing and Analysis

A simplified method of preparing sequencing templates utilizing cell lysates was developed to sequence the large number of clones identified in Example 4 as possibly containing inserts with at least one $(AAAAX)_n$ sequence. This procedure consisted of transferring positive clones from colony hybridization assays to sterile 96 well microtiter plates (Falcon cat. #3072) containing 200 μl of LB/Amp (100 μg/ml) and incubating overnight at 37° C. at 250 rpm. Next, the overnight culture was divided and used in three different procedures involving either setting up of the cell lysates, making replica filters for second hybridizations to confirm initial findings or making glycerol stocks for long term storage of clones.

Cell lysates were made by taking 2 μl of overnight culture and adding this to 100 μl sterile nanopure water in 96 well reaction plates (Perkin Elmer cat. #N801-0560) and heating to 100° C. for 4 minutes in 9600 thermocycler. This was allow to cool, iced, and stored at −20° C. until ready to use.

Replicate filters were made for second hybridization assays by flame sterilizing the 96-pin replicator, dipping the replicator into a 96 well plate containing overnight culture and stamping a 137 mm circular nylon membrane (MagnaGraph, MSI) on a LB/Amp (100 μg/ml) plate and incubating the membrane overnight at 37° C.

The remaining overnight culture was converted to glycerol stocks by the addition of 46 μl 80% glycerol to each well and placing plates on in shaker-incubator set on 250 rpm for a few minutes to mix, then stored at −70° C.

All clones that were positive in two colony hybridization assays were selected and corresponding clones from the cell lysate plates were used for PCR amplification. The PCR reaction products were purified with Qiagen QIAquick 96 PCR Purification plates (Cat. #28180) and used a templates for sequencing. Two microliters of the cell lysate were used in a 50 μl PCR reaction containing M13-47 forward primer at 2 μM (Promega cat. #Q560A), M13 reverse primer (Promega cat. #Q542A) at 2 μM, 1×STR buffer and 2.5 units of AmpliTaq (Perkin Elmer). The following cycle profile was used on a PE 480 thermocycler: 1 cycle at 96° C./2 min, 10 cycles at 94° C./1 min, 56° C./1 min, 70° C./1.5 min; 20 cycles at 90° C./1 min, 56° C./1 min, 70° C./1.5 min; 4° C. hold. PCR reaction products were clean-up with Qiagen QIAquick 96 PCR Purification plates (Cat. #28180) following manufacturers protocol and recovered in 70 μl Tris-HCl 10 mM pH 8.5 at a final concentration of about 35 ng/μl and stored at −20° C.

DNA sequencing was performed using ABI Dye Terminator Sequencing Chemistry and ABI 377 sequencer. The sequencing templates were prepared using ABI Dye Terminator Kit and manufactures protocol (Protocol P/N 402078). Two μl or approximately 30 to 90 ng of purified PCR product (described above) was used as a template DNA for sequencing reaction. The sequencing reaction consisted of 8 μl Dye terminator mix, 2 μl template DNA (35 ng/μl), 4 μl of M13-21 Forward primer at 0.8 μM, and 6 μl of sterile nanopure water. Cycle sequencing on the GeneAmp PCR System 9600 cycling profile was: 25 cycles at 96° C./10 sec, 50° C./5 sec, 60° C./4 minutes; hold 4° C. The extension products were purified by adding 50 μl 95% ethanol and 2 μl 3M Sodium acetate, pH 4.6 to each tube, mixed using a vortexer, placed on ice for 10 minutes, then centrifuged for 30 minutes at maximum speed. The pellet was rinsed with 250 μl 70% ethanol, dried in vacuum centrifuge for about 3 minutes and stored dry at −20° C. until ready for use. The dried pellet was resuspended in 6–9 μl loading buffer then denatured for 2 minutes at 95° C. and stored on ice until loaded on gel.

Five percent Long Ranger gels (FMC BioProducts, Rockland, Me.) were prepared according to manufacturer protocol and polymerized for 2 hours. The gel was pre-run for 45 minutes at 1000 volts. 1.5 μl template in loading buffer was loaded on gel and run under 2× or 4× conditions for 3.5 hrs or 7 hrs, respectively.

DNA sequence data generated from the ABI 377 sequencer was edited to remove any pGEM vector sequences then placed in local database created using Genetics Computer Group Wisconsin Package Software version 9.0 (Madison, Wis.) containing sequence information for all clones being evaluated. Next, clones were examined for the presence, length and sequence patterns of pentamer repeats. Those containing 5 or more repeats were then compared with the BLAST sequence comparison program (Altschul et. al., 1990) to identify duplicated clones and those that already existed in GenBank database at the National Center for Biotechnology Information in Besthesda, Md., USA. Once unique clones were identified, primers were designed for PCR with the aid of OLIGO Primer Analysis Software version 5.0 (National Biosciences, Inc., Plymouth, Minn.).

EXAMPLE 6

Screening Clones for Polymorphism Levels and Determining Chromosomal Location

The Initial screen for polymorphisms was performed on two pooled DNA samples, one containing human genomic DNA 15 random individuals and the other containing 54 CEPH individuals from the NIGMS Human Genetic Mutant Cell Repository (CEPH Collection DNA Pool, cat. #NA13421, Coriell Cell Repositories, Camden, N.J.). Fluorescently labeled PCR primers were used for PCR amplification of target locus from genomic DNA and the PCR products were separated on polyacrylamide gels and visualized on a fluorescent scanner. Those loci with 4 alleles and 50% heterozygosity were subsequently tested with 16 individual CEPH DNAs (102-1, 102-2, 884-1, 884-2, 1331-1, 1331-2, 1332-1, 1332-2, 1347-1, 1347-2, 1362-1, 1362-2, 1413-1, 1413-2, 1416-1, 1416-2) to determine preliminary heterozygosity values. The data for the same loci was then further analyzed to determine number of alleles, allele frequencies and heterozygosity values (see TABLE 2).

Clones found to contain pentamer repeat sequences that met the selection criteria of ≧4 alleles and ≧50% heterozygosity were mapped to determine precise chromosomal location (see TABLE 2). Three different methods were used for mapping: (1) Somatic cell hybrid mapping using the NIGMS panel of 26 somatic cell hybrids (Coriell Cell Repositories, Camden, N.J.) representing single human chromosomes to identify chromosomal origin, (2) radiation hybrid mapping techniques utilizing the GeneBridge 4 RH Panel of 93 RH clones (Schuler et. al., 1996), and (3) standard meiotic linkage mapping techniques and eight families (K102, K884, K1347, 1362, 1331, 1332, 1413, 1416) from the CEPH kindred reference panel and mapped with CRI-MAP multipoint linkage program (Lander & Green, 1987).

Figure 10:
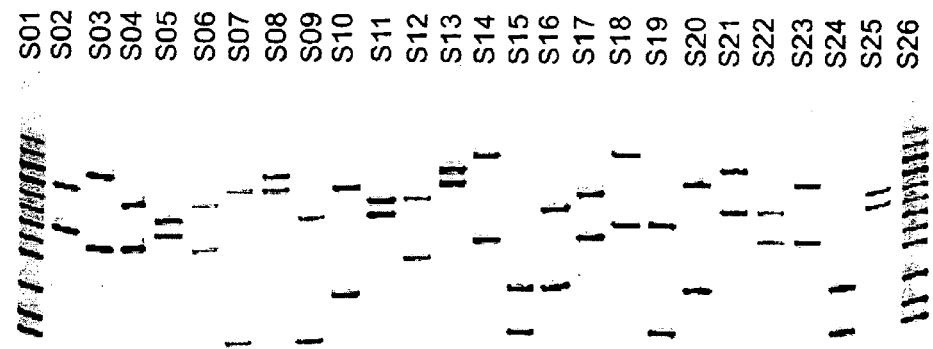
FIG. 10 is a laser printed image of the results of fluorimager scan of fluorescent labeled amplified fragments of a S159 pentanucleotide repeat, after separation by gel electrophoresis.
Figure 11:
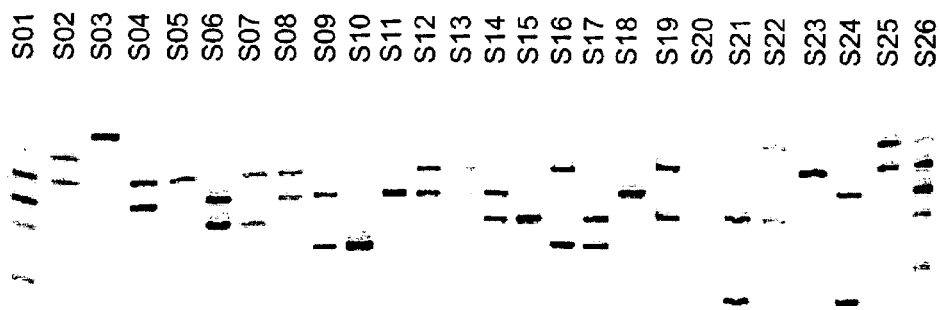
FIG. 11 is a laser printed image of the results of fluorimager scan of fluorescent labeled amplified fragments of a G210 pentanucleotide repeat, after separation by gel electrophoresis.

Clones with heterozygosity values exceeding 70% in the 16 CEPH individuals were evaluated for genotype and allele frequencies in larger population studies containing over 100 individuals from four major races, including, African Americans, Caucasians, Asians, and Hispanics. FIGS. 10 and 11 illustrate the wide variation in the migration of alleles amplified from two different polymorphic ITR loci in genomic DNA samples from 24 different individuals in a population (DNA samples S02 to S25). See Table 1, above, for the sequence of the primer pairs used in this analysis. The gel images were generated by amplifying each pentanucleotide repeat locus using fluorescein labeled primers, followed by separation on polyacrylamide gels and visualized by scanning of the FMBIO II Fluorescent Scanner (Hitachi Software Engineering America, Ltd., San Francisco, Calif.). An alleleic ladder containing most known alleles for each locus assayed was included in a lane at each end of the electrophoresis gel, in lanes S01 and S26. The primer pairs used to amplify each locus had sequences complementary to at least a portion of the sequence of a DNA marker isolated from clone S159 or from clone G210, as illustrated in the Examples above. The primer pair sequences were selected from the primer pairs listed for Clones S159 and G210 Table 1, above.

PCR conditions for polymorphism screens were as follows: 25 μl reactions containing approximately 200 ng for pooled DNA template or 25 ng for individual CEPH DNAs, 1×STR Buffer, 1 unit Taq DNA Polymerase, and 1 μM corresponding primer pair. The sequence of each primer pair used to amplify each of the clones listed in Table 2 is provided in Table 1. Note that each primer has been assigned the SEQ ID NO listed in Table 1. Cycling conditions for the Perkin-Elmer GeneAmp PCR System 9600 Thermal Cycler (Perkin-Elmer, Foster City, Calif.) were: 96° C. for 1 minute, then 10 cycles at 94° C. for 30 seconds, ramp 68 seconds to 60° C., hold 30 seconds, ramp 50 seconds to 70° C., hold for 45 seconds; followed by 20 cycles of 90° C. for 30 seconds, ramp 60 seconds to 60° C., hold for 30 seconds, ramp 50 seconds to 70° C., hold 45 seconds, 60° C. for 30 minutes. PCR Samples were prepared by mixing 2.5 μl of each sample with 2.5 μl 2× Bromophenol Blue Loading Solution, denatured by heating at 95° C. for 2 minutes, iced, then 3 μl of each sample was run on a 4% polyacrylamide gel for 50 minutes at 40 watts. The PCR products were visualized by scanning of a Hitachi FMBIO fluorescent scanner and analyzed with accompanying software (FMBIO Analysis Version 6.0, Hitachi Software Engineering, San Francisco, Calif.).

EXAMPLE 7

Identification of Short Tandem Repeats through GenBank Searches.

An alternate method of identifying tandemly repeated sequences was accomplished by searching GenBank at the National Center for Biotechnology Information (NCBI) for the presence of intermediate tandem repeats. Several methods were employed, including batch searching of GenBank entries on CD-ROM with the Lasergene software package from DNASTAR (Madison, Wis.), batch searching GenBank with the aid of Genetics Computer Group Wisconsin Package Software version 9.0 (Madison, Wis.).

There are $4^5=1024$ distinct five letter words which can be assembled from the four letter (A, C, G, and T) alphabet to make all the possible pentamer repeats, and $4^6=4096$ and $4^7=16,384$ distinct six and seven letter words for six and seven base repeats. However, the number of unique repeat motifs is considerable less due the equivalence of the two complementary strands (e.g., AAAAT is equivalent ATTTT), to and the equivalence of cyclic permutations (e.g., AATAA . . . is equivalent to ATAAA . . . ). In the case of five base repeats, this means that there exists 102 unique classes of pentamer repeats if one leaves out mononucleotide repeats $A_5/T_5$ and $C_5/G_5$.

TABLE 2

| SEQ ID NO. | Clone Number | GenBank Accession Number | Longest ITR Sequence Observed | Observed No. of Alleles | % Heterozygosity (Caucasians) | Chromosomal Location |
|---|---|---|---|---|---|---|
| 1 | C074 | none | $[TTTTG]_9$ | 6 | 75 | 1 |
| 2 | C221 | none | $[GTTTT]_{13}$ | 7 | 78 | 9p |
| 3 | C240 | none | $[CAAAA]_7$ | 4 | 42 | NA |
| 4 | C331 | none | $[GTTTT]_{10}$ | 5 | 43 | NA |
| 5 | C362 | none | $[GTTTT]_5$ | 4 | 62 | 4 |
| 6 | C390 | none | $[CAAAA]_7$ | 5 | 56 | NA |
| 7 | G022 | none | $[AAAAG]_6$ | 4 | 63 | 2p |
| 8 | G023 | none | $[AAAAG]_{10}$ | 12 | 71 | 16q |
| 9 | G025 | none | $[AAAAG]_6$ | 12 | 86 | 1 |
| 10 | G047 | none | $[AAAAG]_9$ | 5 | 86 | 2p |
| 11 | G065 | none | $[TTTTC]_6$ | 13 | 100 | 1q |
| 12 | G085 | none | $[AAAAG]_{11}$ | 8 | 93 | 10q |
| 13 | G132 | none | $[CTTTT]_{15}$ | 12 | 100 | 4 qter |
| 14 | G145 | none | $[AAAAG]_{13}$ | 8 | 33 | NA |
| 15 | G152 | none | $[AAAAG]_6$ | 5 | 87 | 8 qter |
| 16 | G153 | none | $[AAAAG]_6$ | 5 | 88 | 8 qter |
| 17 | G158 | none | $[AAAAG]_5$ | 8 | 75 | 5q |
| 18 | G181 | none | $[GAAAA]_{14}$ | 5 | 72 | NA |
| 19 | G210 | none | $[CTTTT]_6$ | 9 | 56 | 8p |
| 20 | G212 | none | $[CTTTT]_9$ | 6 | 100 | NA |
| 21 | G233 | none | $[AAAAG]_8$ | 12 | 50 | 10q |
| 22 | G234 | none | $[AAAAG]_{12}$ | 4 | 80 | 16 qter |
| 23 | G235 | none | $[TTTTC]_6$ | 4 | 56 | 2p |
| 24 | G331 | none | $[CTTTT]_8$ | 5 | 73 | NA |
| 25 | G405 | none | $[CTTTT]_6$ | 10 | 80 | NA |
| 26 | G475 | none | $[GAAAA]_{12}$ | 12 | 92 | 15q22.3 |
| 27 | G539 | none | $[GAAAA]_{12}$ | 13 | 100 | 15q26.2 |
| 28 | S023 | X05367 | $[AAAAT]_6$ | 4 | 50 | NA |
| 29 | S071 | M90078 | $[AAAAT]_8$ | 4 | 56 | 6q26–27 |
| 30 | S085 | U07000 | $[AAAAT]_5$ | 7 | 44 | 22q11 |
| 31 | S125 | Z73416 | $[AAAAT]_{13}$ | 5 | 64 | 22q11.2-qter |
| 32 | S132 | Z83847 | $[AAAAT]_{10}$ | 8 | 69 | 22 |
| 33 | S136 | Z82250 | $[AAAAT]_6$ | 11 | 94 | 22q12-qter |
| 34 | S159 | AC000014 | $[GAAAA]_9$ | 12 | 72 | 21q22-qter |
| 35 | S176 | AC000059 | $[GTTTT]_9$ | 4 | 56 | 7q21–7q22 |
| 36 | S189 | Z54073 | $[AAAAC]_8$ | 5 | 69 | 22q11.2-qter |
| 37 | S199 | Z84475 | $[GTTTT]_7$ | 4 | 75 | 6q21 |
| 38 | S040 | X06583 | $[AGCCTGG]_4$ | 2 | NA | NA |
| 39 | S066 | M68516 | $[ACTCC]_5$ | 3 | NA | NA |
| 40 | S077 | M25718 | $[AATAC]_{12}$ | 6 | NA | NA |
| 41 | S097 | Z21818 | $[CAGGCT]_3$ | 3 | NA | NA |
| 42 | S103 | X15949 | $[ATCCC]_8$ | 3 | NA | NA |
| 43 | S110 | X54108 | $[GGA(A/G)T]_{32}$ | 6 | NA | NA |

All unique combinations of 5, 6 and 7 base repeats with at least three consecutive copies were used to search the GenBank human genome database. All repeat regions containing three or more copies of a repeat, or copies with occasional base substitutions, were identified. Using existing sequence data, primers flanking the repeat region were designed and the target locus was PCR amplified and evaluated for polymorphic content as described in Example 6.

Each clone containing a sequence identified using primers assembled using information from the GenBank database was then screened for repeat sequence content as described in Example 7. The sequence of each clone found to contain an ITR sequence, i.e. an ITR marker, was assigned one of the SEQ ID NO's from 28 to 43. See Table 1 for the sequence of primers comprising sequences which flank the ITR region of each such marker. See Table 2 for a summary of results of analyzing the characteristics of the sequence of each such ITR marker.

EXAMPLE 8

Evaluation of Intermediate Tandem Repeat Loci for PCR Artifacts (i.e., % Stutter)

Many of the markers described in this work represent a new class of markers which produce less of a PCR artifacts known as "stutter" (see Definitions section of the Detailed Description of the Invention, above). The generation of these artifacts occurs during PCR amplification, presumably as a result of a DNA polymerase-related phenomenon called repeat slippage (Levinson & Gutman, 1987. Mol. Biol. Evol. 4(3):203–221; Schlotterer & Tautz, 1992. NAR 20:211–215). The end result of repeat slippage is the generation of PCR products that contain different numbers of repeat units than the authentic allele. If sufficient amount of slippage occurs during PCR, the amplified product will be visualized as a major and minor band, with the major band corresponding to the authentic allele and the minor band corresponding to the altered product containing more or less of the repeat units.

To quantify the amount of the stutter band present at different loci, PCR amplification products of 6 ITR loci (C221, GO23, G025, G210, S159 and an additional ITR not described in this patent, S117) and 17 tetranucleotide tandem repeat loci (F13A01, THO1, TPOX, F13B, FESFPS, D7S820, CSF1PO, D13S317, D8S1179, D16S539, LPL, FGA, D5S818, D3S1358, D18S51, vWA, and D21S11) were run on an ABI 377 Sequencer and analyzed using GenScan software (PE Applied Biosystems, Foster City, Calif.). The peak heights measured in relative fluorescence units (RFU) were determined for all major and minor peaks observed in the 25 to 40 individual samples investigated at each loci. The percentage of RFU observed in the minor peak (generally either 5 bp smaller than the authentic allele in the pentanucleotides or 4 bp smaller in tetranucleotide repeats) to the major authentic allele peak was calculated (see Table 3).

Figure 2:
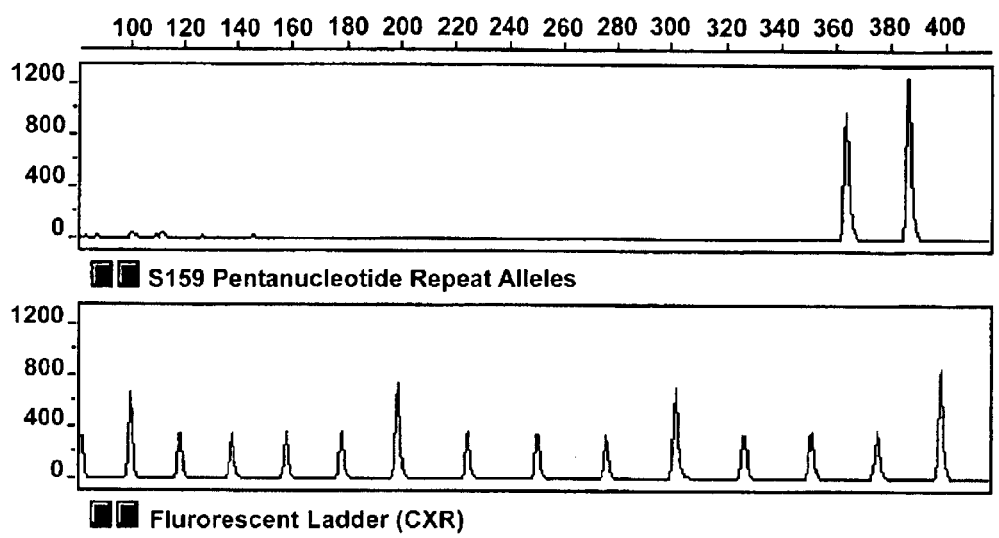
FIG. 2 is an electropherogram of an S159 pentanucleotide repeat.
Figure 3:
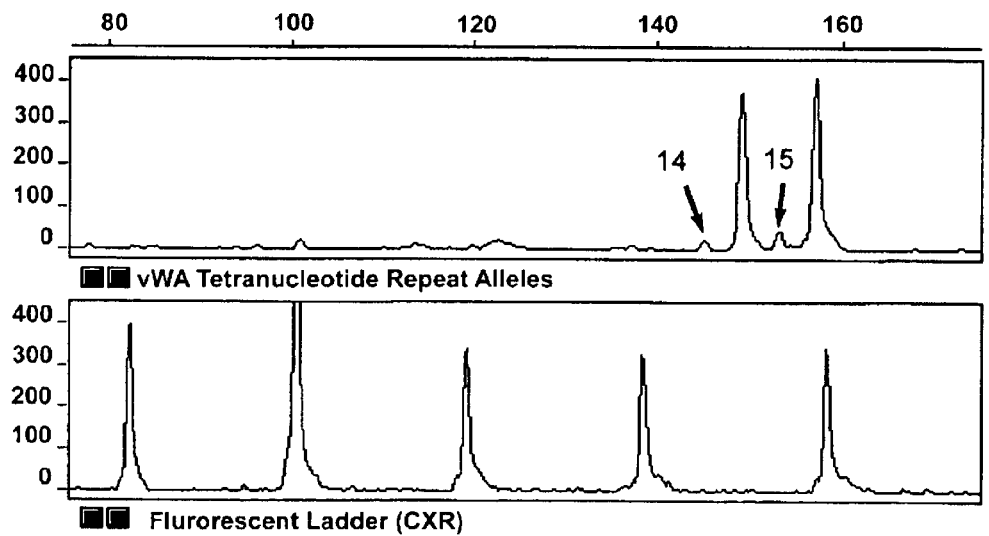
FIG. 3 is an electropherogram of a vWA tetranucleotide repeat.
Figure 4:
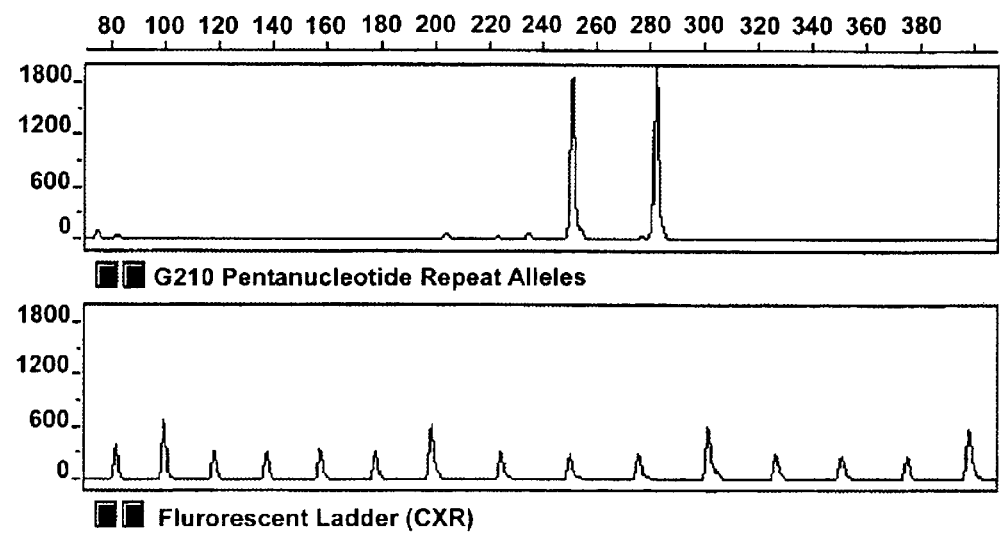
FIG. 4 is an electropherogram of a G210 pentanucleotide repeat.
Figure 5:
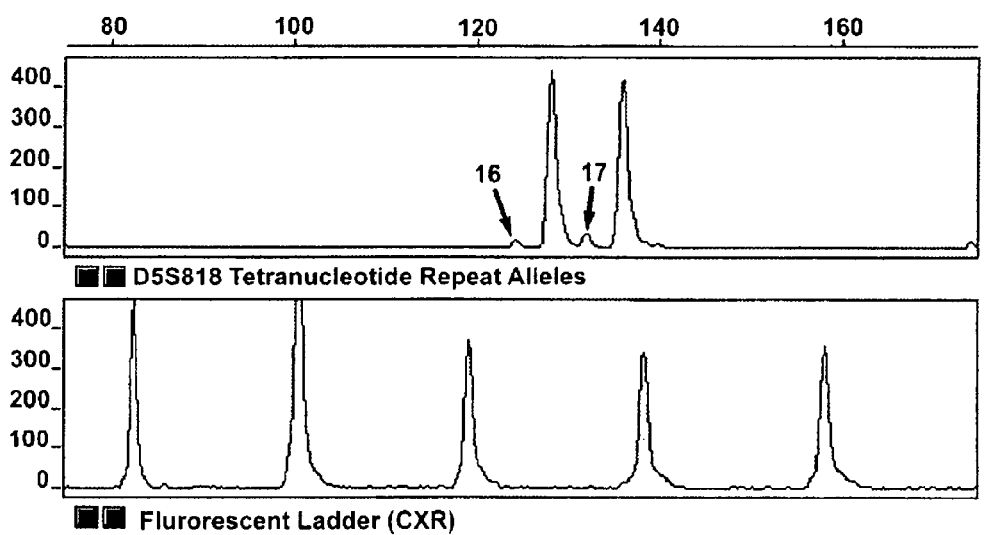
FIG. 5 is an electropherogram of a D5S818 tetranucleotide repeat.
Figure 6:
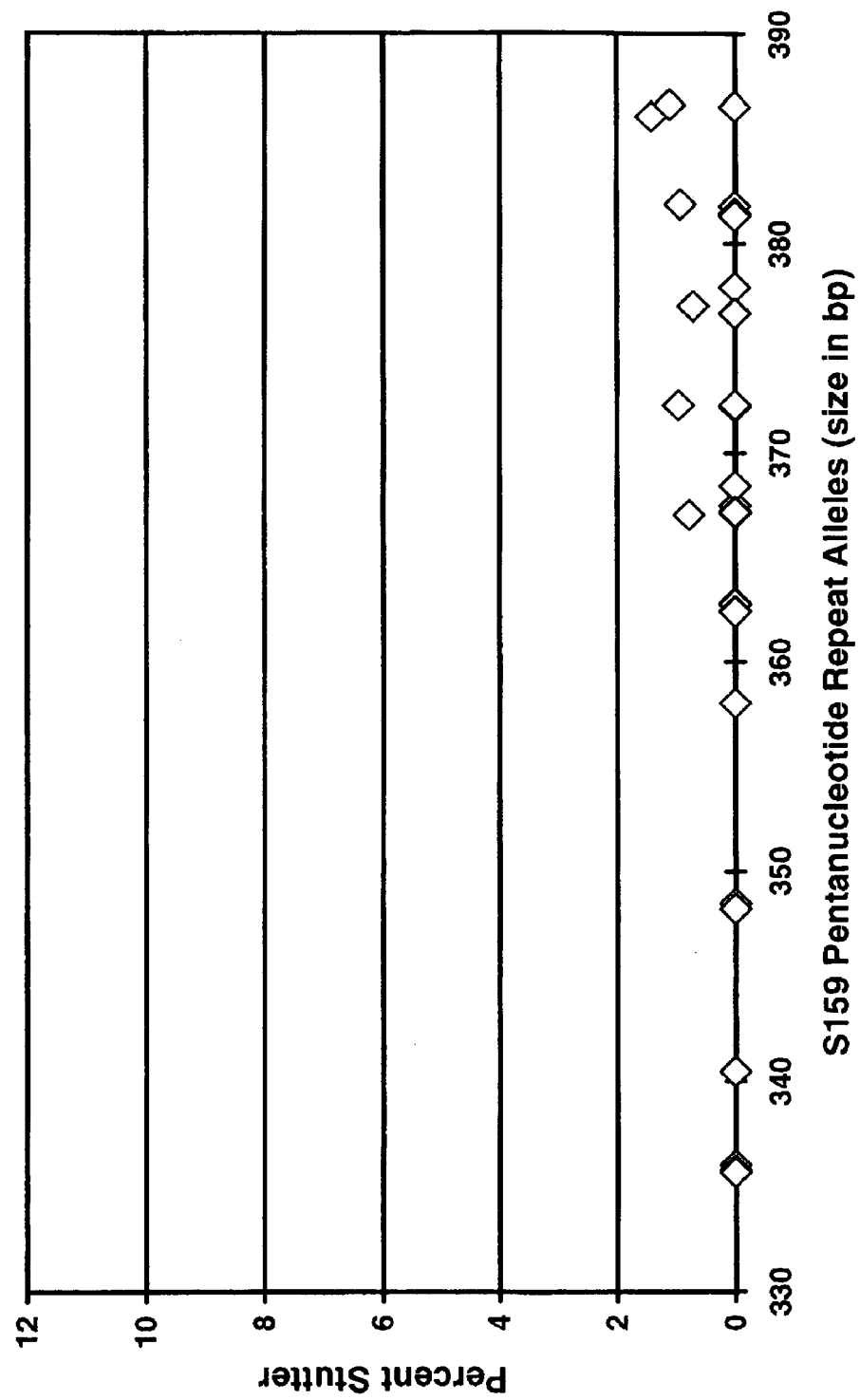
FIG. 6 is a scatter plot of % stutter of the S159 pentanucleotide repeat.
Figure 7:
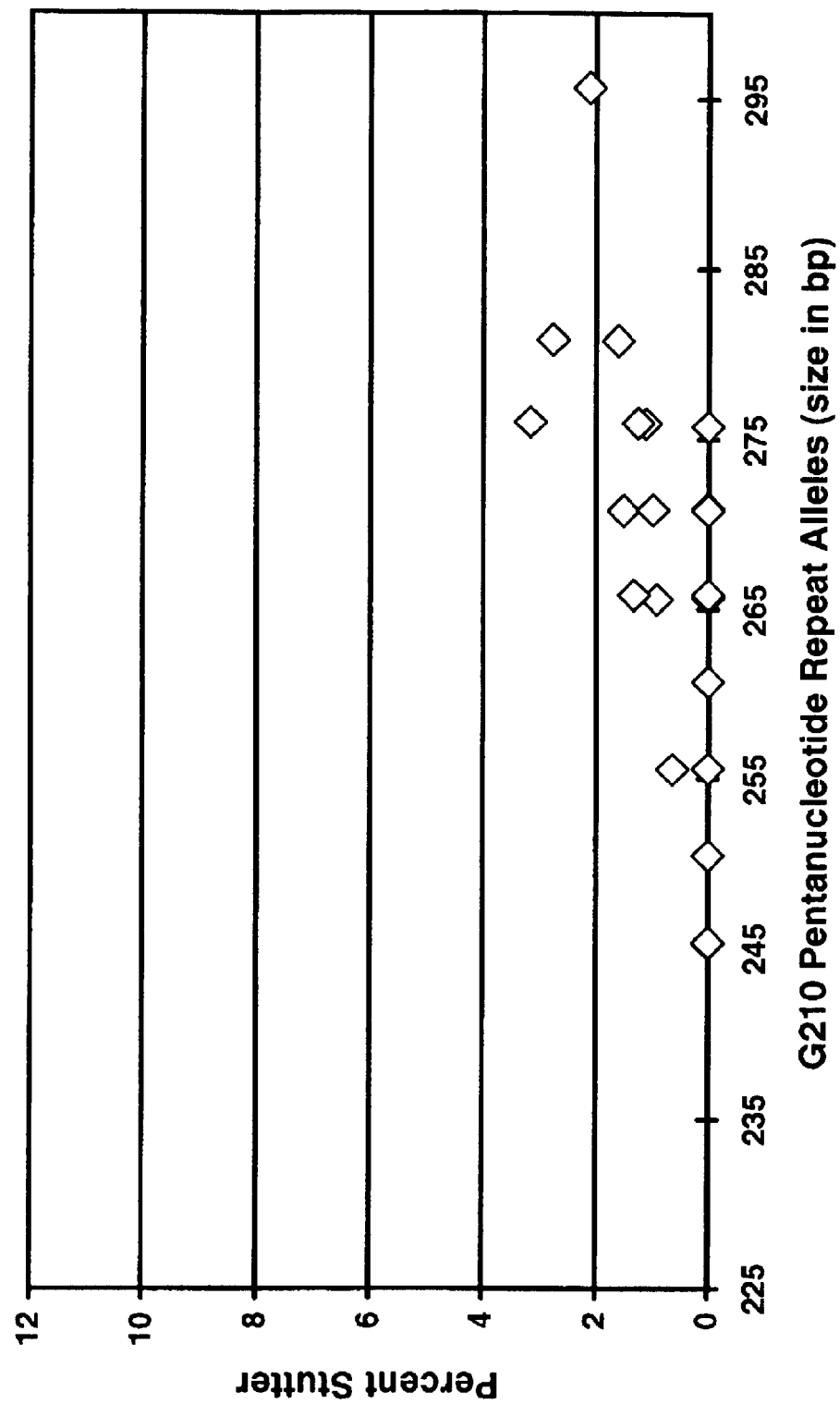
FIG. 7 is a scatter plot of % stutter of the G210 pentanucleotide repeat.
Figure 8:
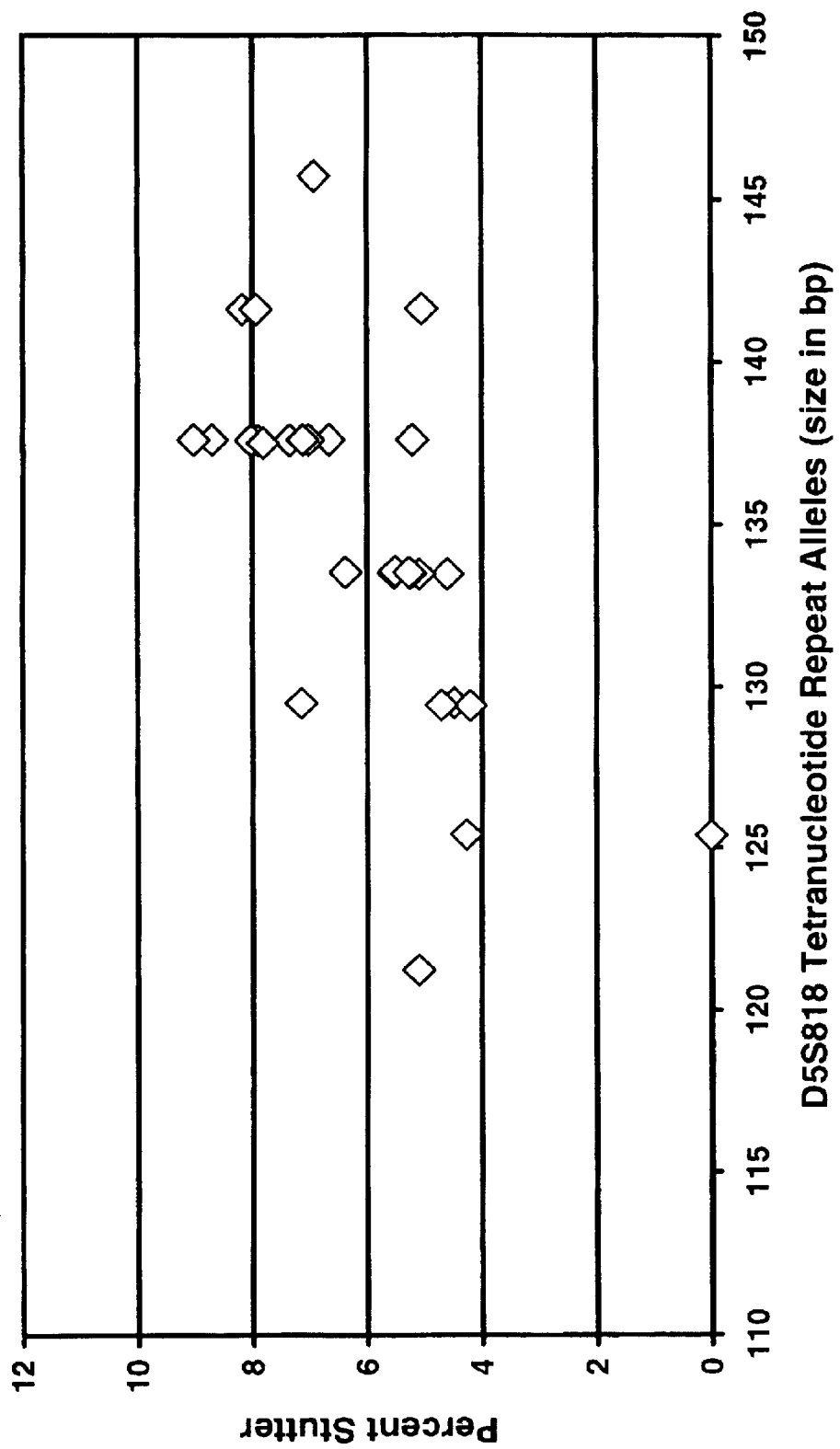
FIG. 8 is a scatter plot of % stutter of the D5S818 tetranucleotide repeat.
Figure 9:
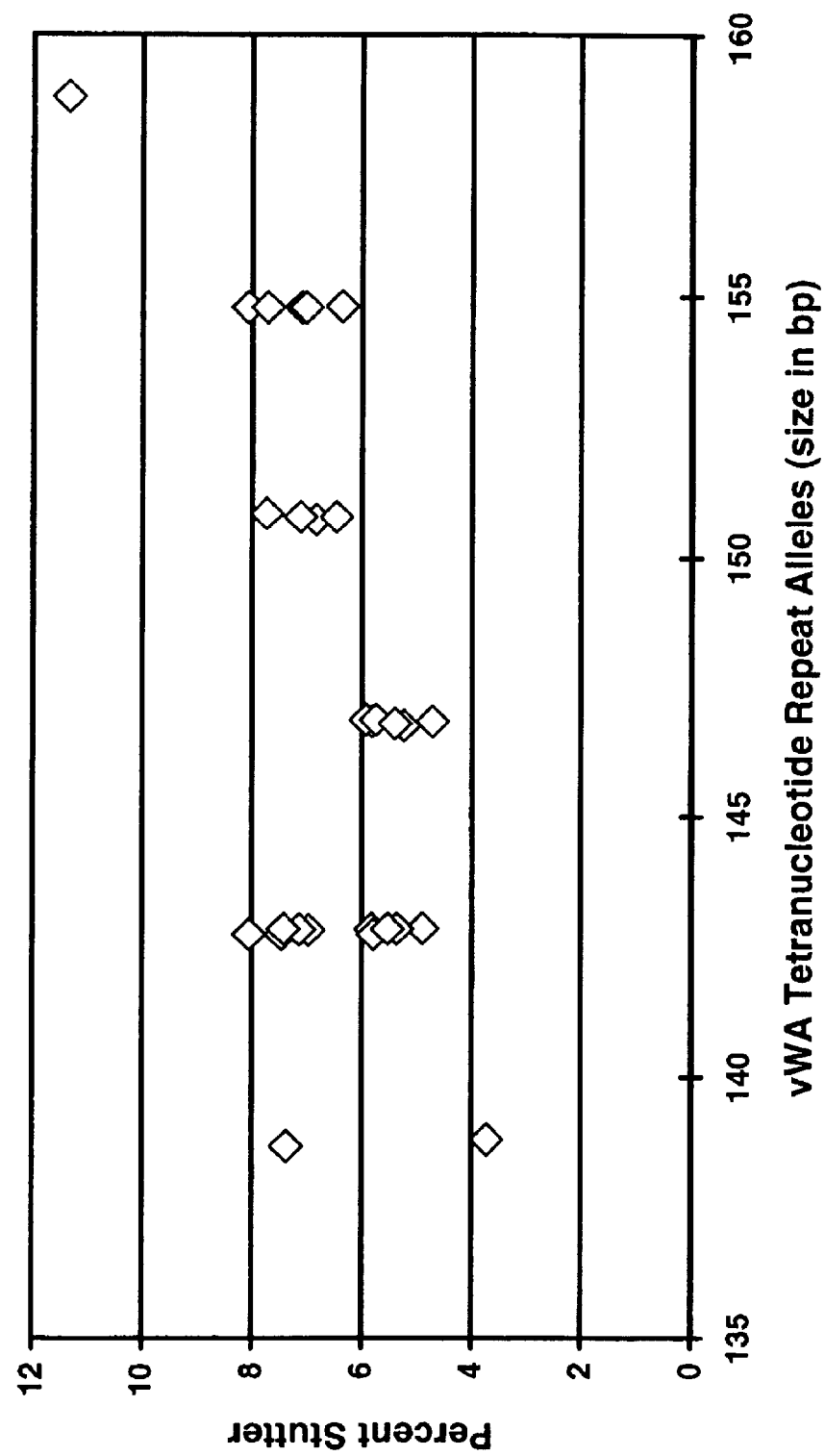
FIG. 9 is a scatter plot of % stutter of the vWA tetranucleotide repeat.

Examples of ABI 377 electropherograms for ITR loci S159 (FIG. 2) and G210 (FIG. 3) and tetranucleotide repeat loci vWA (FIG. 4) and D5S818 (FIG. 5) show minimal or absent stutter at ITR loci and clearly observable stutter for tetranucleotide repeat loci. Specifically, see the stutter artifacts indicated by arrows 14 and 15 in the electropherogram of the vWA tetranucleotide repeat locus reproduced in FIG. 3, and by arrows 16 and 17 in the electropherogram of the D5S818 tetranucleotide repeat locus reproduced in FIG. 5. Compare those distinct artifact peaks to the vanishingly small artifacts in electropherograms of the pentanucleotide repeats of the marker DNA isolated from Clone S159 (i.e. marker having the sequence identified by SEQ ID NO:34) as shown in FIG. 2, and of the marker DNA isolated from Clone G210 (i.e. marker having the sequence identified by SEQ ID NO:19) in FIG. 4. The specific electropherograms reproduced in FIGS. 2–5 are the highest incidences of stutter observed for each of the loci.

Some variability in the amount of stutter was observed for all loci. In general the trend was for alleles containing the highest number of repeats (as indicated by their size in base pairs) to exhibit the highest amount of stutter. Percent stutter values for each of the 25 to 40 individuals tested are shown is scatter plots (FIGS. 6, 7, 8 and 9).

In summary, the percentage of the "stutter" band to the authentic allele band was significantly lower in most of the ITR loci evaluated compared to the tetranucleotide tandem repeat loci. This was true even though the tetranucleotide loci used represent the best of this type of marker currently known. For example, 13 such tetranucleotide markers, including several of the tetranucleotide markers assayed as described reported in Table 3 below as having a high % stutter, have been selected by the U.S. Federal Bureau of Investigation for use in analyzing all DNA samples for the national Combined DNA Index System (CODIS). (Macivee, I. (1998) *Profiles* in DNA 1(3):2).

TABLE 3

| Locus Name or Clone Number | Tandem Repeat Unit Length | Average Percent Stutter | Highest Percent Stutter | Lowest Percent Stutter | Standard Deviation | Number of Alleles Analyzed |
|---|---|---|---|---|---|---|
| Clone S159 | 5 bp (ITR) | 0.1 | 1.4 | 0.0 | 0.4 | 40.0 |
| Clone G210 | 5 bp (ITR) | 0.6 | 3.2 | 0.0 | 0.9 | 30.0 |
| Clone C221 | 5 bp (ITR) | 0.9 | 3.3 | 0.0 | 0.9 | 27.0 |
| F13A01 | 4 bp | 1.2 | 9.7 | 0.0 | 2.5 | 34.0 |
| TH01 | 4 bp | 1.7 | 5.2 | 0.0 | 1.7 | 34.0 |
| Clone S117 | 5 bp (ITR) | 2.0 | 6.9 | 0.0 | 1.7 | 37.0 |
| Clone G023 | 5 bp (ITR) | 2.3 | 6.6 | 0.0 | 1.7 | 39.0 |
| TPOX | 4 bp | 2.4 | 5.6 | 0.0 | 1.8 | 34.0 |
| F13B | 4 bp | 2.6 | 7.7 | 0.0 | 1.7 | 31.0 |
| FESFPS | 4 bp | 3.6 | 10.0 | 0.0 | 2.3 | 34.0 |
| D7S820 | 4 bp | 3.8 | 8.2 | 1.6 | 1.6 | 28.0 |
| CSF1PO | 4 bp | 4.1 | 9.5 | 0.0 | 2.5 | 31.0 |
| Clone G025 | 5 bp (ITR) | 4.5 | 9.3 | 0.0 | 2.1 | 36.0 |
| D13S317 | 4 bp | 4.7 | 7.5 | 1.7 | 1.5 | 26.0 |
| D8S1179 | 4 bp | 5.0 | 8.3 | 2.4 | 1.6 | 27.0 |
| D16S539 | 4 bp | 5.1 | 8.6 | 1.7 | 2.0 | 28.0 |
| LPL | 4 bp | 5.4 | 15.0 | 1.7 | 3.1 | 29.0 |
| FGA | 4 bp | 5.5 | 11.6 | 3.0 | 1.7 | 36.0 |
| D5S818 | 4 bp | 6.1 | 9.0 | 0.0 | 1.9 | 28.0 |
| D3S1358 | 4 bp | 6.1 | 12.5 | 0.9 | 2.1 | 25.0 |
| D18S51 | 4 bp | 6.5 | 11.6 | 2.5 | 2.4 | 28.0 |
| vWA | 4 bp | 6.6 | 11.4 | 3.7 | 1.4 | 28.0 |
| D21S11 | 4 bp | 7.5 | 15.7 | 1.9 | 3.5 | 30.0 |

What is claimed is:

1. A method for detecting a target intermediate tandem repeat DNA sequence having a low incidence of stutter artifacts, comprising the steps of:
   (a) providing a sample of DNA having at least one target intermediate tandem repeat sequence, wherein the target intermediate tandem repeat sequence is a region of the DNA containing at least one repeat unit consisting of a sequence of five (5), six (6), or seven (7) base pairs repeated in tandem at least two (2) times; and
   (b) amplifying the target intermediate tandem repeat sequence using at least one oligonucleotide primer, comprising a sequence which is complementary to and flanks a region of a double-stranded DNA marker containing a template intermediate tandem repeat sequence, wherein the template intermediate tandem repeat sequence is a region of the DNA marker which contains the repeat unit sequence repeated in tandem at least two (2) times, provided that the DNA marker has a sequence of SEQ ID NO:32; and
   (c) detecting the target intermediate tandem repeat sequence in the sample of DNA, wherein an average stutter artifact of no more than 2.4% is observed.

2. The method of claim 1 wherein the oligonucleotide primer used in amplifying the target intermediate tandem repeat sequence has a fluorescent label covalently attached thereto.

3. The method of claim 1, wherein the stutter artifact is observed in step (b) by comparing the target intermediate tandem repeat sequence detected to fragments of known length in a DNA size marker.

4. The method of claim 3, wherein an average stutter of no more than 1.1% is observed.

5. A method for detecting at least one target intermediate tandem repeat sequence in a DNA sample, wherein the target intermediate tandem repeat sequence is a region of the DNA sample which contains at least one repeat unit consisting of a sequence of five (5), six (6), or seven (7) base pairs repeated in tandem at least two (2) times; the method comprising the steps of:
   (a) providing at least one oligonucleotide primer comprising a nucleic acid sequence which is complementary to and flanks a region of a DNA marker containing a template intermediate tandem repeat sequence, wherein the DNA marker has a sequence of SEQ ID NO:32;
   (b) providing a DNA sample comprising the target intermediate tandem repeat sequence;
   (c) using the at least one oligonucleotide primer to amplify the target intermediate repeat sequence of the DNA sample; and
   (d) detecting polymorphisms in the amplified target intermediate tandem repeat sequence.

6. The method of claim 5, wherein the sample of DNA provided in step (b) is a sample of human genomic DNA.

7. The method of claim 5, wherein the target intermediate tandem repeat sequence is a perfect intermediate tandem repeat.

8. The method of claim 5, wherein the target intermediate tandem repeat sequence is an imperfect intermediate tandem repeat.

9. The method of claim 5, wherein the oligonucleotide primer provided in step (a) comprises a sequence of SEQ ID NO:124 and SEQ ID NO:125, when the DNA marker sequence is SEQ ID NO:32.

10. A kit for the detection of at least one target intermediate tandem repeat sequence in a sample of DNA, wherein the target intermediate tandem repeat sequence is a region of the sample of DNA which contains at least one repeat unit consisting of a sequence of five (5), six (6), or seven (7) base pairs repeated in tandem at least two (2) times comprising:
   a container which has at least one oligonucleotide primer for amplifying the at least one target intermediate tandem repeat sequence, wherein the oligonucleotide primer comprises a sequence of nucleic acids which is complementary to and flanks a region of a double-stranded DNA marker containing a template intermediate tandem repeat sequence comprising the repeat unit repeated in tandem at least two (2) times; and wherein the DNA marker has a sequence of SEQ ID NO:32;
   a container which has at least one oligonucleotide primer for amplifying the at least one target intermediate tandem repeat sequence, wherein the oligonucleotide primer comprises a sequence of nucleic acids which is complementary to and flanks a region of a double-stranded DNA marker containing a template intermediate tandem repeat sequence comprising the repeat unit repeated in tandem at least two (2) times; and wherein the DNA marker has a sequence of SEQ ID NO:32.

11. The kit of claim 10, further comprising a DNA marker.

* * * * *